(12) United States Patent
Kamp et al.

(10) Patent No.: US 11,377,639 B2
(45) Date of Patent: Jul. 5, 2022

(54) LINEAGE REPROGRAMMING TO INDUCED CARDIAC PROGENITOR CELLS (ICPC) BY DEFINED FACTORS

(71) Applicant: WISCONSIN ALUMNI RESEARCH FOUNDATION, Madison, WI (US)

(72) Inventors: Timothy Joseph Kamp, Madison, WI (US); Pratik Arvind Lalit, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 169 days.

(21) Appl. No.: 14/542,280

(22) Filed: Nov. 14, 2014

(65) Prior Publication Data

US 2015/0140658 A1 May 21, 2015

Related U.S. Application Data

(60) Provisional application No. 61/904,881, filed on Nov. 15, 2013.

(51) Int. Cl.
   *C12N 5/071* (2010.01)
   *C12N 5/077* (2010.01)

(52) U.S. Cl.
   CPC ......... *C12N 5/0657* (2013.01); *C12N 5/0661* (2013.01); *C12N 2501/06* (2013.01); *C12N 2501/415* (2013.01); *C12N 2501/60* (2013.01); *C12N 2506/1307* (2013.01)

(58) Field of Classification Search
   CPC .......... C12N 5/0661; C12N 2506/1307; C12N 2501/60; C12N 2501/415
   See application file for complete search history.

(56) References Cited

U.S. PATENT DOCUMENTS

| | | | |
|---|---|---|---|
| 5,464,758 A | 11/1995 | Gossen et al. | |
| 8,268,620 B2 | 9/2012 | Thomson et al. | |
| 8,486,701 B2* | 7/2013 | Schwartz | C12N 5/0657 435/363 |
| 10,106,772 B2 | 10/2018 | Thomson et al. | |
| 10,563,176 B2* | 2/2020 | Ahlfors | C12N 5/0662 |
| 2011/0223670 A1* | 9/2011 | Schwartz | C12N 5/0657 435/467 |
| 2013/0216503 A1* | 8/2013 | Srivastava | C12N 5/0657 424/93.7 |

OTHER PUBLICATIONS

Yu et al Science, 2009, 324, 797-801.*
Kojima and Ieda, Cell. Mol. Life Sci. 2017, 1-13.*
Ieda et al, Cell. Aug. 6, 2010; 142(3): 375-386.*
Islas et al, (PNAS USA 109:13016-21, Aug. 7, 2012.*
Abu-Issa (Annu Rev. Cell Dev Biol. 2007, 23, 45-68.*
Cao et al Cell Research, 23, 1119-1132) and (Year: 2013).*
Foshay et al Stem Cells, 23,530-543 (Year: 2005).*
Qyang et al Cell Stem cell, 1, 165-179 (Year: 2007).*
Steinhauser et al Regeneration of the heart; EMBO Molecular Medicine, vol. 3, 701-712 (Year: 2011).*
Kitajima et al., Development. 127:3215-3226 (Year: 2000).*
Wamstad et al Cell, 151, 206-220 (Year: 2012).*
Dixon Molecular Therapy, 19(9), 1695-1703 (Year: 2011).*
Abu-Issa, Radwan, and Margaret L. Kirby. "Heart field: from mesoderm to heart tube." Annu. Rev. Cell Dev. Biol. 23 (2007): 45-68.
Cao, Nan, et al. "Highly efficient induction and long-term maintenance of multipotent cardiovascular progenitors from human pluripotent stem cells under defined conditions." Cell research 23.9 (2013): 1119-1132.
Foshay, Kara, et al. "JAK2/STAT3 directs cardiomyogenesis within murine embryonic stem cells in vitro." Stem Cells 23.4 (2005): 530-543.
Gossen, Manfred, and Hermann Bujard. "Tight control of gene expression in mammalian cells by tetracycline-responsive promoters." Proceedings of the National Academy of Sciences 89.12 (1992): 5547-5551.
Islas, Jose Francisco, et al. "Transcription factors ETS2 and MESP1 transdifferentiate human dermal fibroblasts into cardiac progenitors." Proceedings of the National Academy of Sciences 109.32 (2012): 13016-13021.
Kattman, Steven J., et al. "Stage-specific optimization of activin/nodal and BMP signaling promotes cardiac differentiation of mouse and human pluripotent stem cell lines." Cell stem cell 8.2 (2011): 228-240.
Kwon, Chulan, et al. "Canonical Wnt signaling is a positive regulator of mammalian cardiac progenitors." Proceedings of the National Academy of Sciences 104.26 (2007): 10894-10899.

(Continued)

*Primary Examiner* — Anoop K Singh
(74) *Attorney, Agent, or Firm* — McDonnell Boehnen Hulbert and Berghoff LLP

(57) ABSTRACT

Animal cells, notably adult fibroblasts, are advantageously reprogrammed in direct lineage reprogramming methods using defined factors to produce proliferative and multipotent induced cardiac progenitor cells (iCPC). The iCPC thus produced can be differentiated under suitable differentiation conditions to cardiac lineage cells including cardiomyocytes, smooth muscle cells, and endothelial cells, as evidenced by expression of lineage specific markers. Sets of factors effective in combination to reprogram the fibroblasts can include a set that includes some or all of 5 factors (Mesp1, Baf60c, Nkx2.5, Gata4, Tbx5), a set that includes some or all of 11 factors (Mesp1, Mesp2, Gata4, Gata6, Baf60c, SRF, Isl1, Nkx2.5, Irx4, Tbx5, Tbx20), a set that includes some or all of 18 factors (T, Mesp1, Mesp2, Tbx5, Tbx20, Isl1, Gata4, Gata6, Irx4, Nkx2.5, Hand1, Hand2, Tbx20, Tbx18, Tip60, Baf60c, SRF, Hey2), and a set that includes some or all of 22 factors (T, Mesp1, Mesp2, Tbx5, Tbx20, Isl1, Gata4, Gata6, Irx4, Nkx2.5, Hand1, Hand2, Tbx20, Tbx18, Tip60, Baf60c, SRF, Hey2, Oct4, Klf4, Sox2, L-myc).

7 Claims, 27 Drawing Sheets
(24 of 27 Drawing Sheet(s) Filed in Color)

Specification includes a Sequence Listing.

(56) References Cited

OTHER PUBLICATIONS

Lawson, Kristie A., et al. "Clonal analysis of epiblast fate during germ layer formation in the mouse embryo." Development 113.3(1991): 891-911.

Lu, Tung-Ying, et al. "Repopulation of decellularized mouse heart with human induced pluripotent stem cell-derived cardiovascular progenitor cells." Nature communications 4 (2013).

Mader, Sylvie, and John H. White. "A steroid-inducible promoter for the controlled overexpression of cloned genes in eukaryotic cells." Proceedings of the National Academy of Sciences 90.12 (1993): 5603-5607.

Madsen, Cort S., et al. "Smooth muscle-specific expression of the smooth muscle myosin heavy chain gene in transgenic mice requires 5'-flanking and first intronic DNA sequence." Circulation Research 82.8 (1998): 908-917.

Miano, Joseph M., et al. "Smooth muscle myosin heavy chain exclusively marks the smooth muscle lineage during mouse embryogenesis." Circulation research 75.5 (1994): 803-812.

Nelson, Daryl O., et al. "Irx4 identifies a chamber—specific cell population that contributes to ventricular myocardium development." Developmental Dynamics 243.3 (2014): 381-392.

Qyang, Yibing, et al. "The renewal and differentiation of Isl1+ cardiovascular progenitors are controlled by a Wnt/β-catenin pathway." Cell stem cell 1.2 (2007): 165-179.

Scott, Ian C. "1 Life Before Nkx2. 5: Cardiovascular Progenitor Cells: Embryonic Origins and Development." Current topics in developmental biology 100 (2012): 1. [abstract only].

Snyder, Marylynn, et al. "Stat3 directly controls the expression of Tbx5, Nkx2. 5, and GATA4 and is essential for cardiomyocyte differentiation of P19CL6 cells." Journal of Biological Chemistry 285.31 (2010): 23639-23646.

Tarui, Suguru, et al. "Direct Induction of Human Cardiac Progenitor Cells to Functional Cardiomyocytes by Defined Factors." Circulation 124.21 Supplement (2011): A11472. [abstract only].

Wada, Rie, et al. "Induction of human cardiomyocyte-like cells from fibroblasts by defined factors." Proceedings of the National Academy of Sciences 110.31 (2013): 12667-12672.

Wang, Yaolin et al. "A regulatory system for use in gene transfer." Proceedings of the National Academy of Sciences 91.17 (1994): 8180-8184.

Zhang, Jianhua, et al. "Extracellular matrix promotes highly efficient cardiac differentiation of human pluripotent stem cells the matrix sandwich method." Circulation research 111.9 (2012): 1125-1136.

Stadtfeld et al. A reprogrammable mouse strain from gene targeted embryonic stem cells, Net Methods. 2010 7(1):53-55.

Carey et al. A single-gene transgenic mouse strain for reprogramming adult somatic cells, Net Methods. 2010 7(1):56-59.

Lalit et al. "Lineage reprogramming of fibroblasts into proliferative induced cardiac progenitor cells by defined factors," Cell Stem Cell, 2016, 18, 354-367.

Kattman et al. "Multipotent Flk1+ cardiovascular progenitor cells give rise to the cardiomyocyte, endothelial, and vascular smooth muscle lineages," Developmental Cell, 2006, 11, 723-732.

* cited by examiner

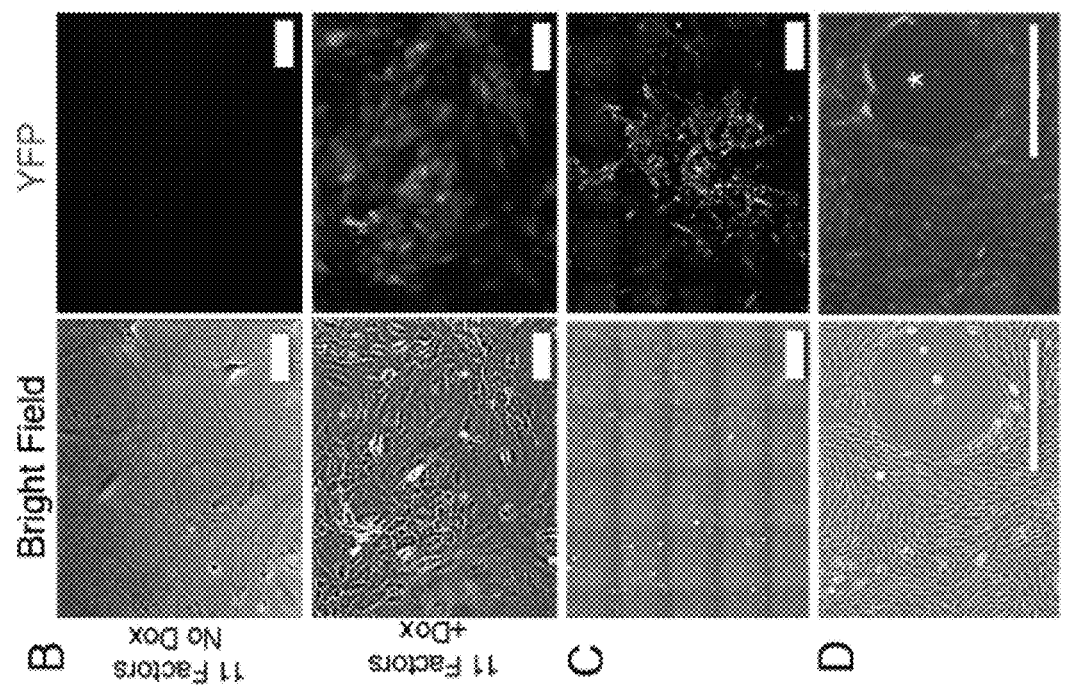
FIG. 1, CONTINUED

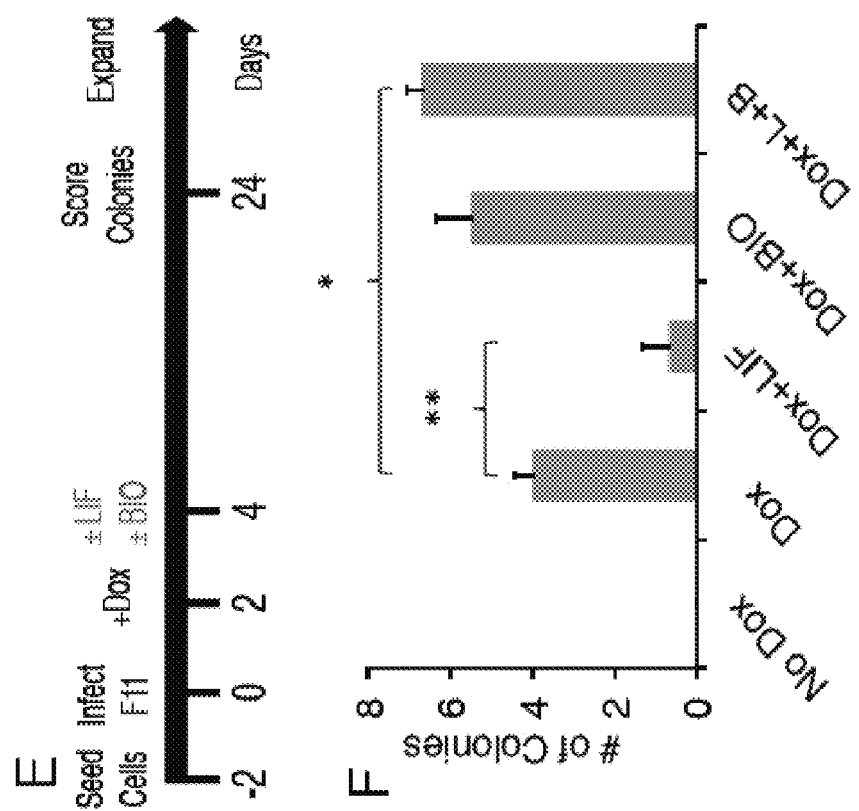
FIG. 1, CONTINUED

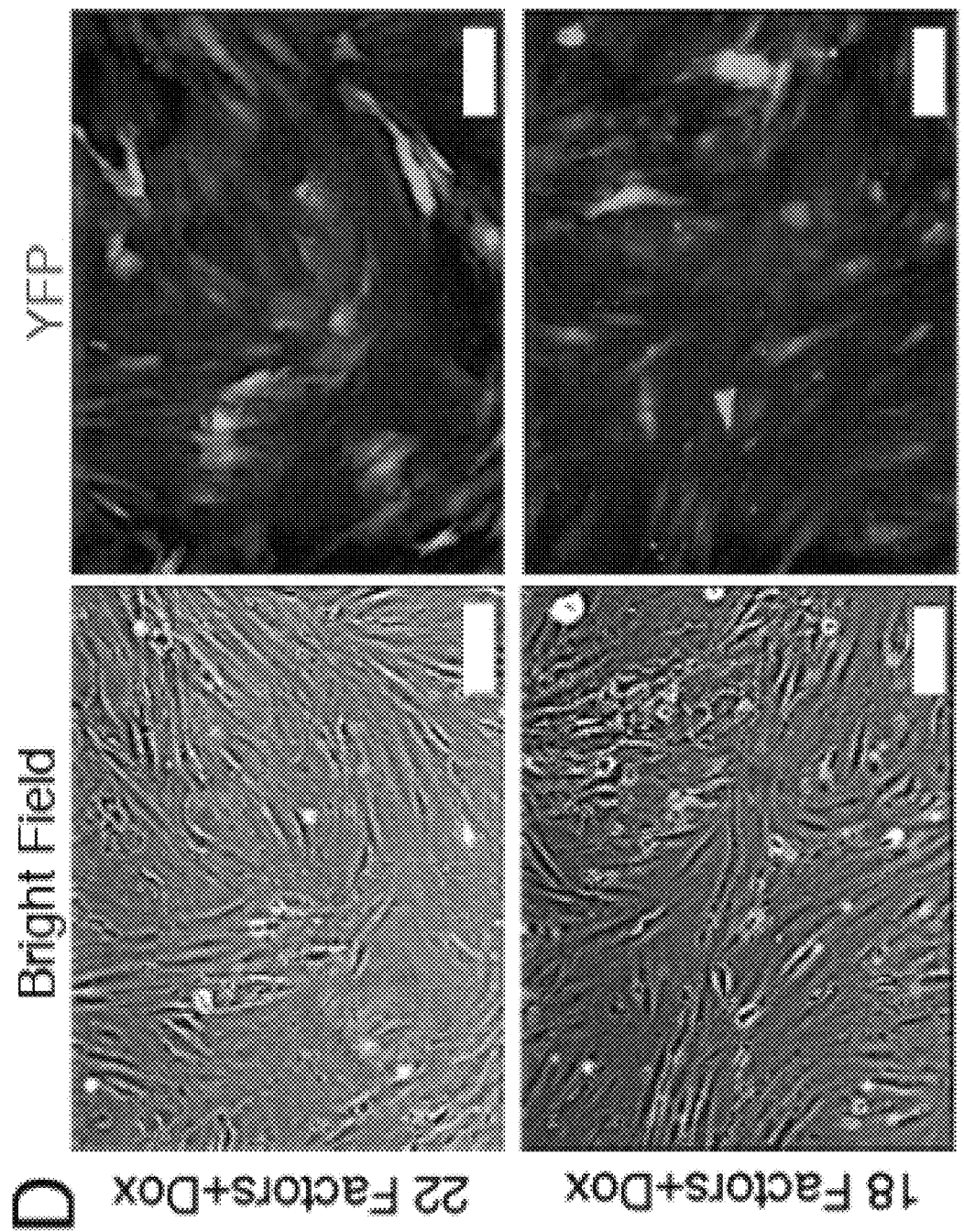
FIG. 3, CONTINUED

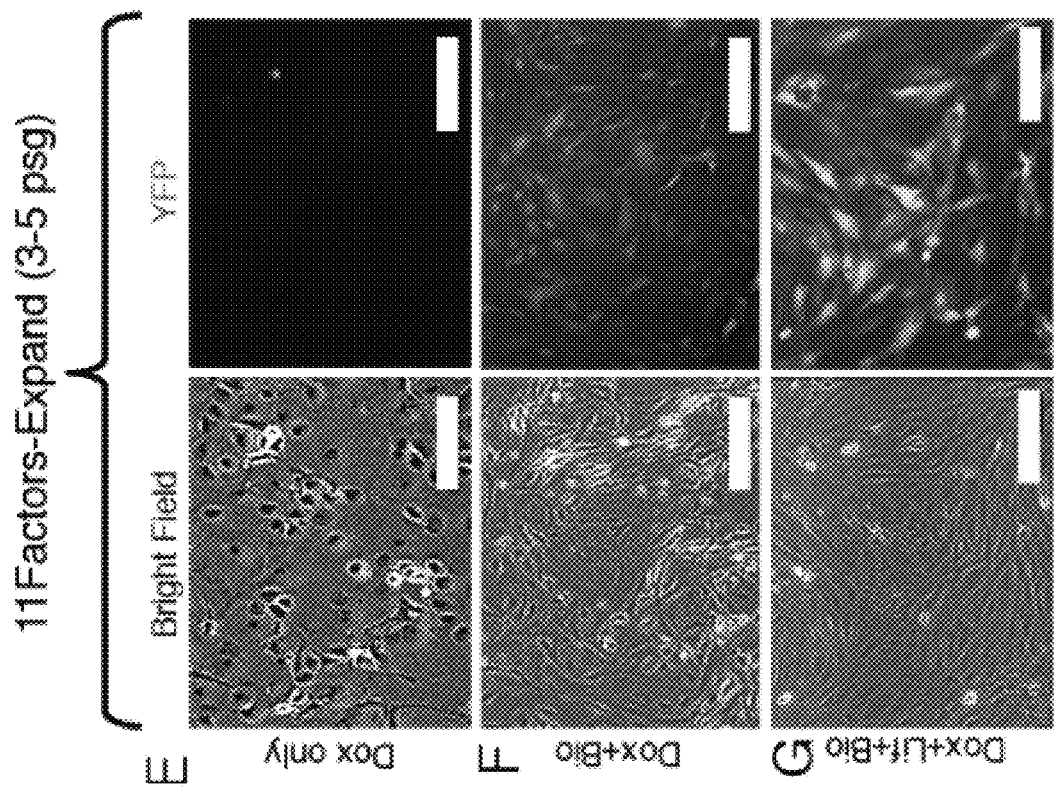
FIG. 3, CONTINUED

FIG. 4

| Upregulated - GO Term | Genes | P value |
|---|---|---|
| Regulation of cellular metabolic process | 226 | 1.08E-10 |
| Immune response | 49 | 8.16E-09 |
| Positive regulation of cell proliferation | 58 | 2.69E-08 |
| Negative regulation of cell differentiation | 42 | 8.07E-08 |
| Cardiovascular system development | 82 | 2.63E-07 |
| Anti apoptosis | 49 | 5.30E-07 |
| Notch signaling involved in heart development | 4 | 6.04E-05 |
| Jak/Stat signaling | 8 | 6.34E-03 |

| Downregulated - GO Term | Genes | P value |
|---|---|---|
| Cell communication | 189 | 3.33E-16 |
| Cell adhesion | 61 | 1.22E-14 |
| Cell differentiation | 158 | 1.02E-13 |
| Chemotaxis | 42 | 2.56E-13 |
| Programmed cell death | 88 | 1.02E-06 |

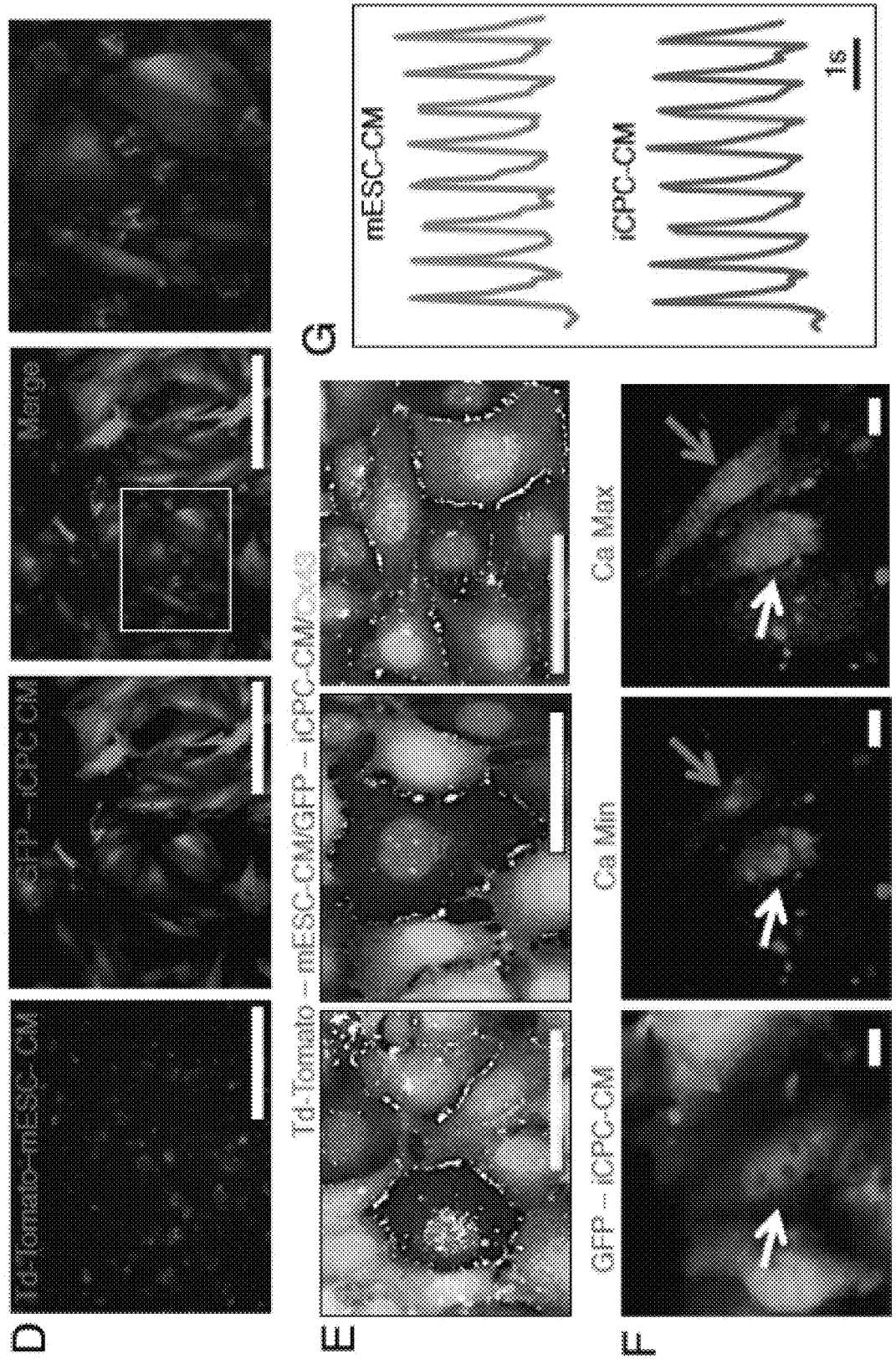
FIG. 6, CONTINUED

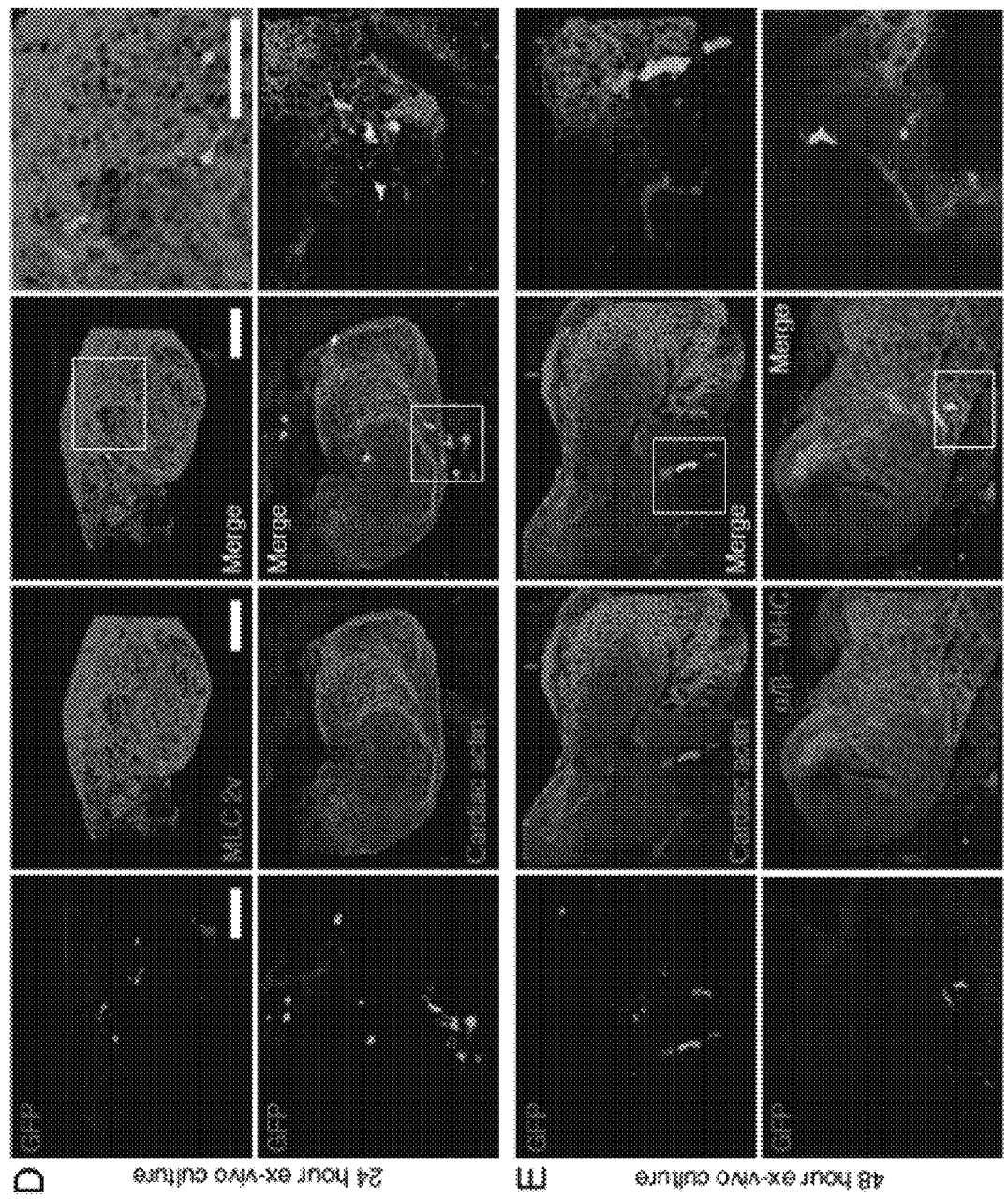
FIG. 7, CONTINUED

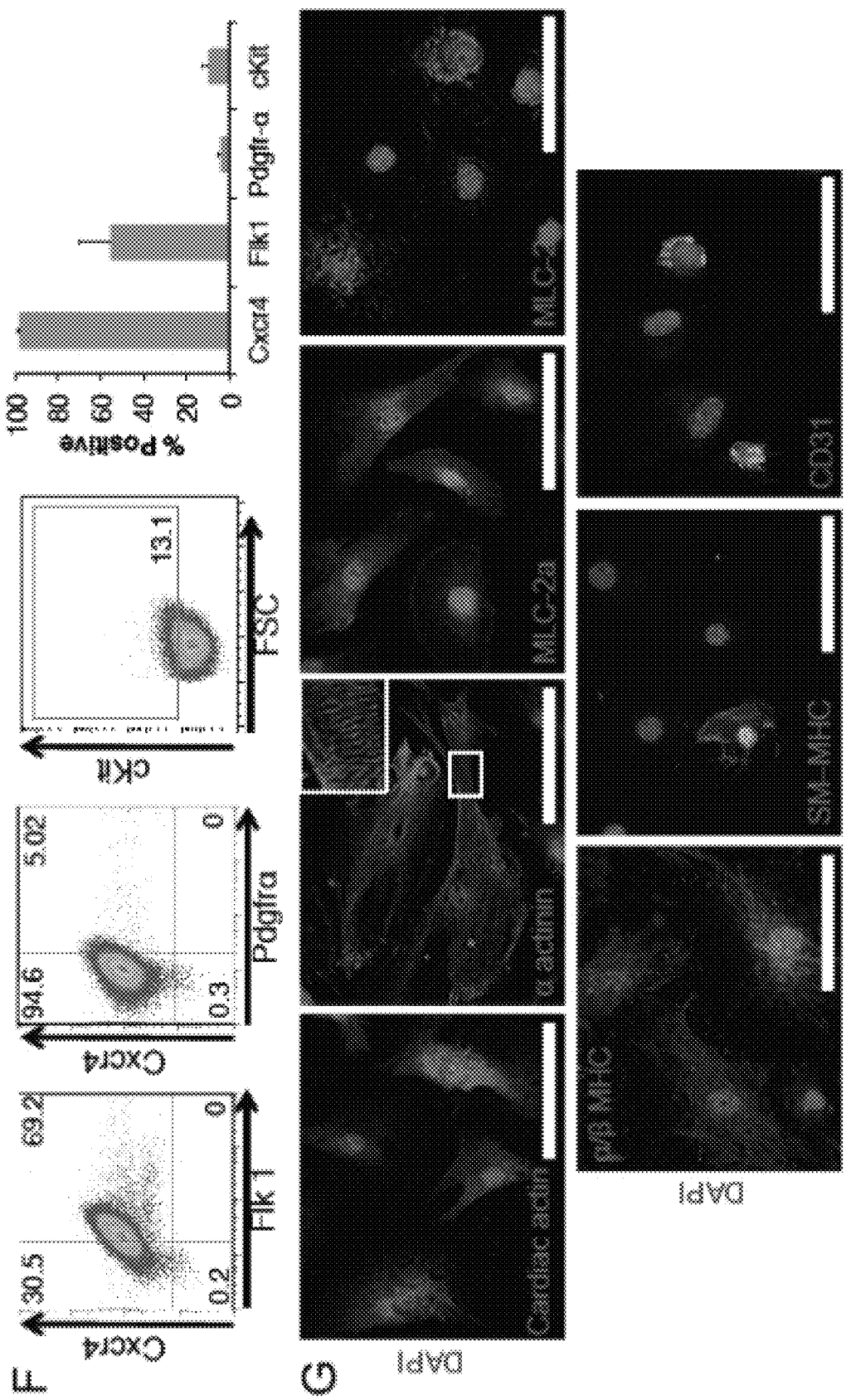
FIG. 8, CONTINUED

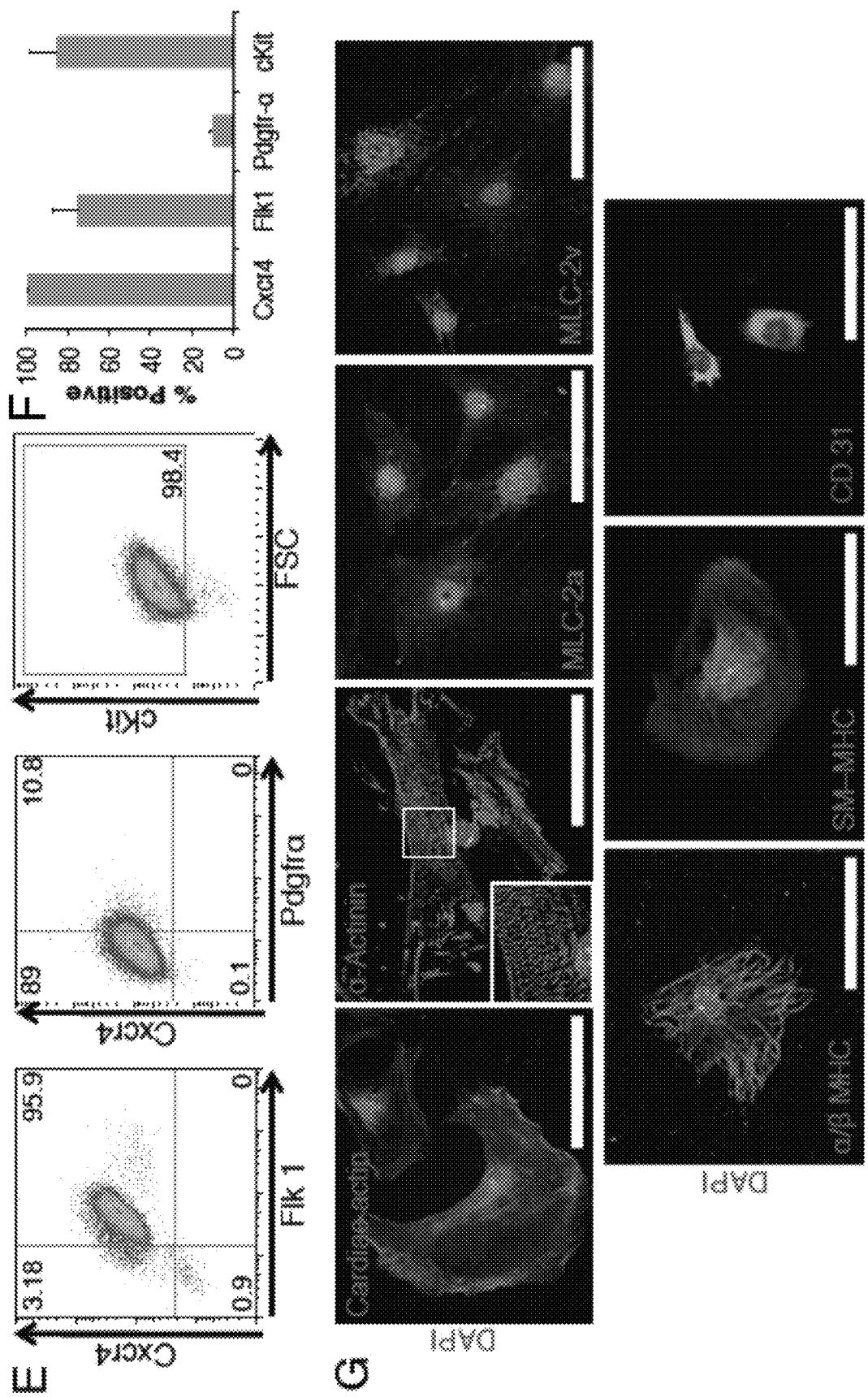
FIG. 9, CONTINUED

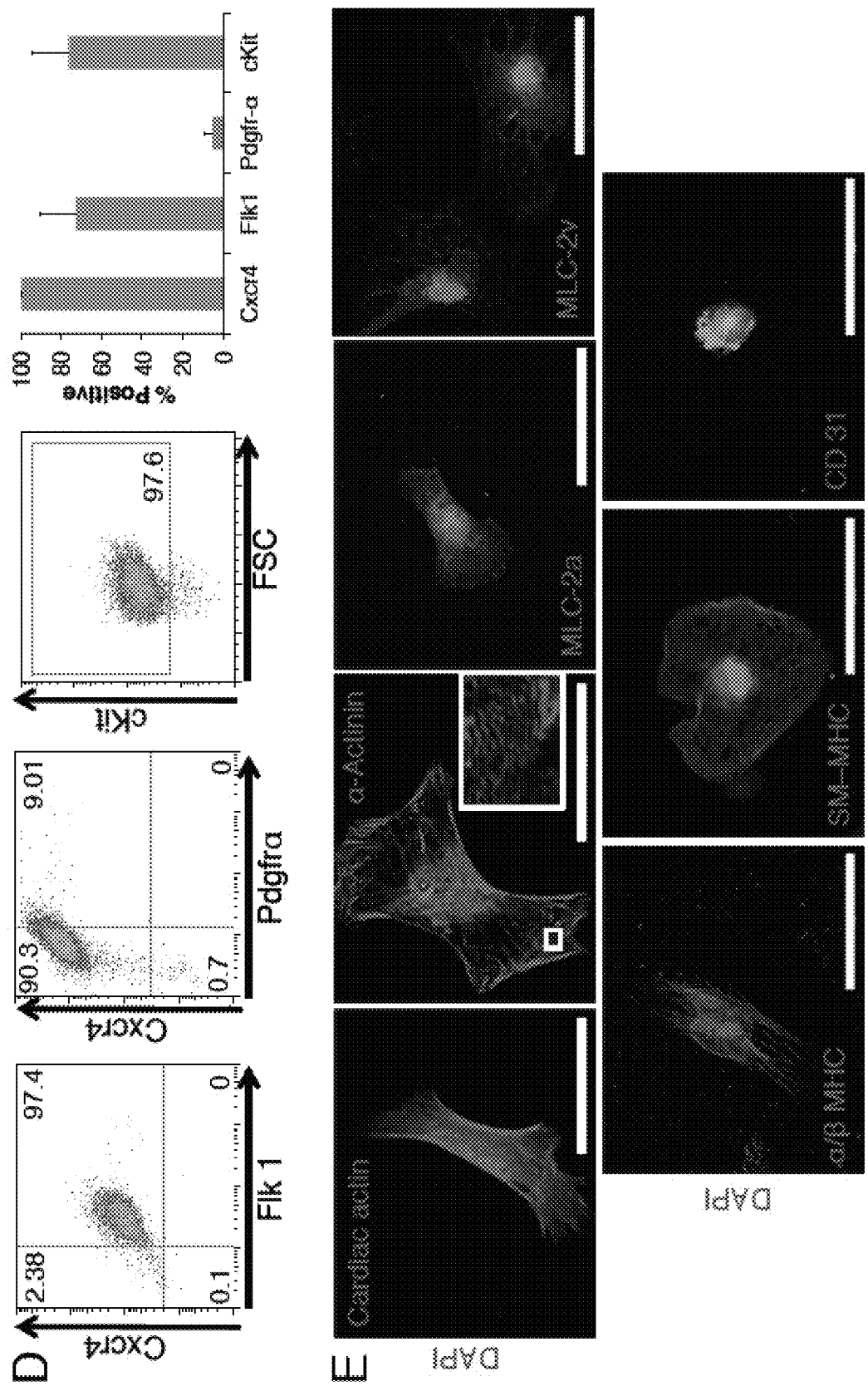
FIG. 10, CONTINUED

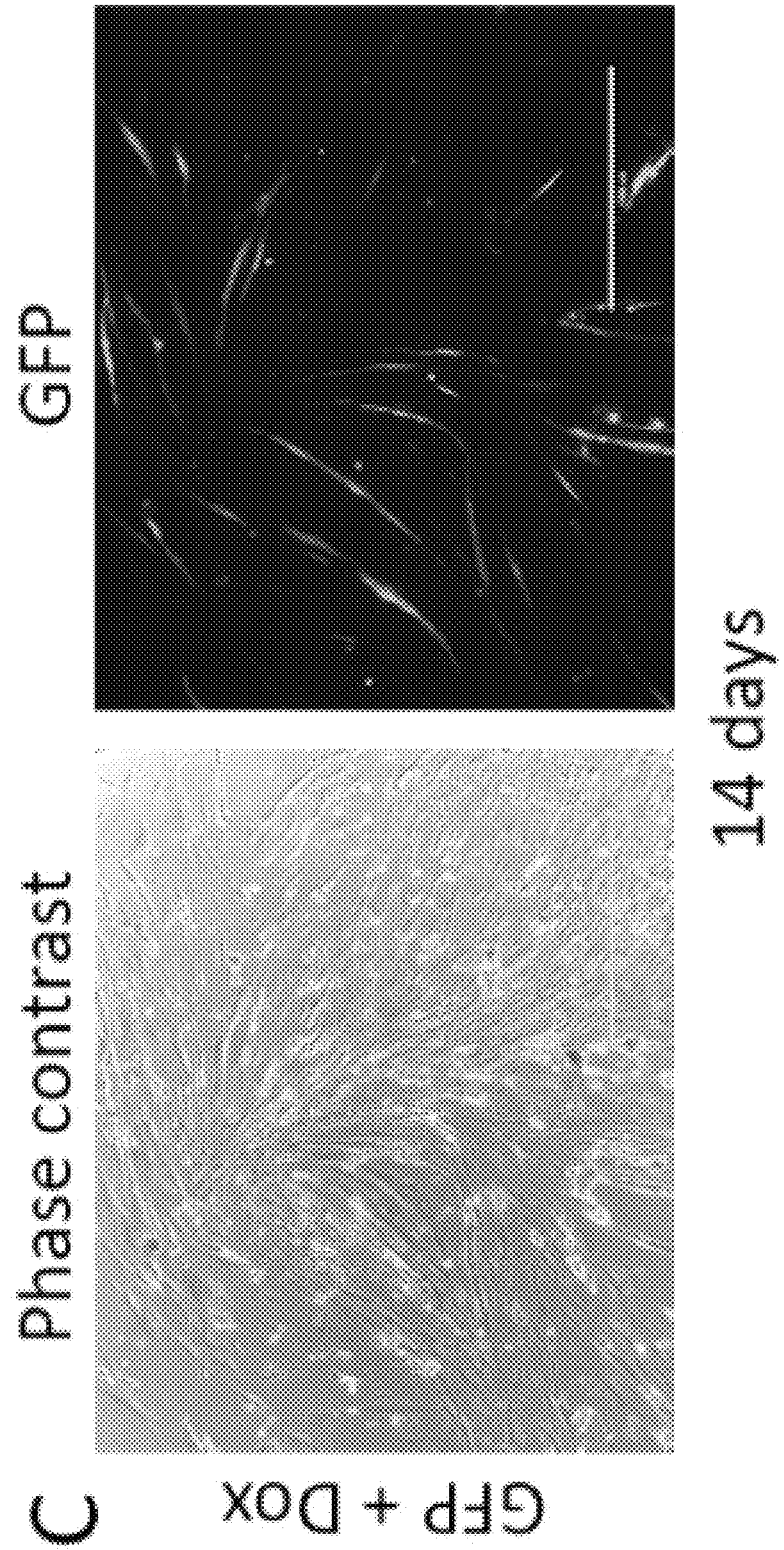
FIG. 11, CONTINUED

FIG. 11, CONTINUED
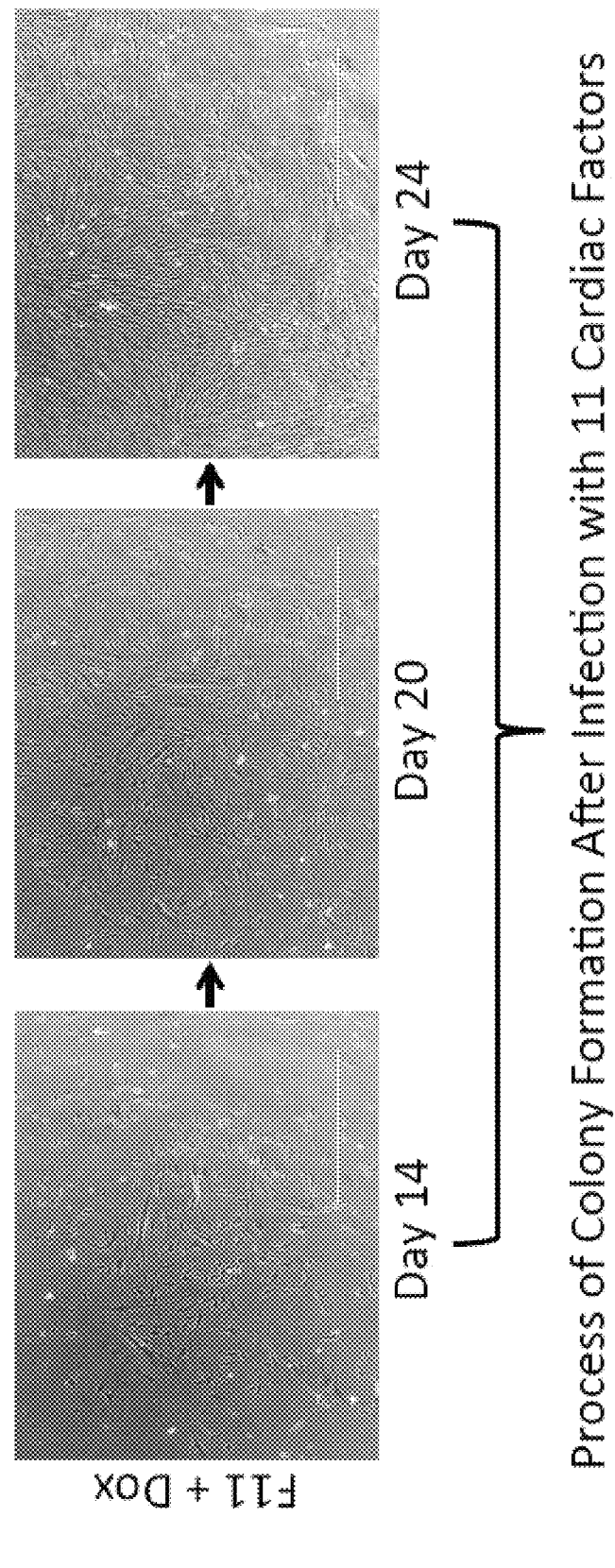

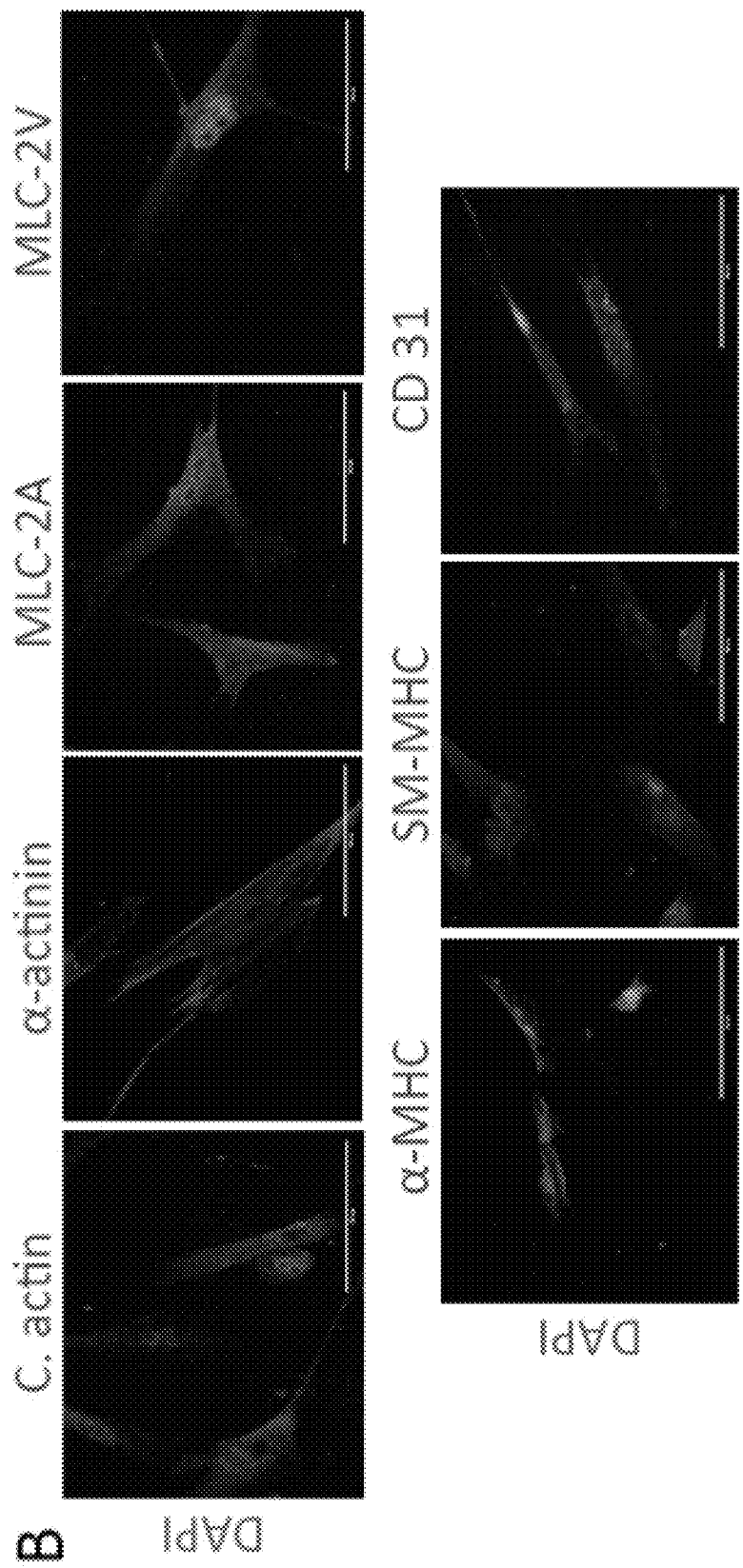
FIG. 12, CONTINUED

FIG. 13

| Early Cardiac TFs (E7.75) | | Late Cardiac TFs (E8.5-12) | | Cardiac Chromatin Remodeling Factors | | iPSC Factors | |
|---|---|---|---|---|---|---|---|
| Mesp1 | Gata6 | Tbx18 | | Tip60 | | Klf4 | |
| Mesp2 | Islet1 | Mef2c | | Baf60c | | L-myc | |
| Nkx2.5 | Srf | Hand1 | | | | Oct4 | |
| Tbx5 | T | Hand2 | | | | Sox2 | |
| Tbx20 | Gata4 | Hey2 | | | | | |
| Irx4 | | | | | | | |

SEQUENCE LISTING

<160> NUMBER OF SEQ ID NOS: 22

<210> SEQ ID NO 1
<211> LENGTH: 1842
<212> TYPE: DNA
<213> ORGANISM: Mus musculus

<400> SEQUENCE: 1

| | | | | | | |
|---|---|---|---|---|---|---|
| atggcggaga | agcggagggg | ctcaccgtgc | agcatgctaa | gcctcaaggc | gcacgccttc | 60 |
| tctgtggagg | cactgatcgg | cgccgagaag | cagcaacagc | ttcaaaagaa | gcggagaaag | 120 |
| ctggccacgg | aagaggcggc | gggggcggtg | gaagacgcag | gctgcagccg | tagcggaggc | 180 |
| gcggggagt | acggctgctc | ggaggccgac | gaagaagcgg | ctgccccgcc | gccggcagcc | 240 |
| ggggcggcgt | ccgggccagc | gcggagctgc | gcggacgcg | agcggagctg | tggctcccgc | 300 |
| ggagcggcgg | gcagctgtga | ggatggcttc | ctgcagggcg | cctccccgtt | ggcatccccg | 360 |
| ggaggctccc | cgaaagggtc | tcccgtacct | ggcttggcac | gaccggggac | cccgctgccc | 420 |
| gcgccgcagg | ccccgagagt | agatctgcaa | ggagcggagc | tctggaagcg | ctttcacgaa | 480 |
| ataggcaccg | agatgatcat | caccaaagcc | ggcaggcgca | tgtttccagc | aatgcgggtg | 540 |
| aagatctccg | gattagaccc | tcaccagcaa | tattacattg | ccatggatat | tgtgccggtg | 600 |
| gacaacaaga | gatacaggta | tgtttaccat | agctctaagt | ggatggtggc | aggaaatgct | 660 |
| gattccccgg | tgccacccag | agtatacatt | catccagact | caccggcctc | tggggagact | 720 |
| tggatgagac | aagtcatcag | cttcgacaag | ctgaaactta | ccaacaatga | gctggatgac | 780 |
| caaggccata | tcattcttca | ttctatgcac | aaataccaac | cacgtgtgca | tgtcatccgt | 840 |
| aaagattgcg | gagatgatct | gtcccccatc | aagcctgttc | catcaggaga | gggagtgaag | 900 |
| gcattctcct | ttccagaaac | cgtcttcaca | actgtcactg | cctatcagaa | tcagcagatt | 960 |
| actcgcctta | agatagacag | gaatccattt | gccaaaggtt | ccgagactc | tgggaggaac | 1020 |
| agaatgggtt | tggaagctct | ggtggagtca | tacgcattct | ggaggccatc | actacggact | 1080 |
| ctcacctttg | aagatatccc | tggaatccca | aagcaaggca | acacaagttc | ttcagctctg | 1140 |
| ctccaaggca | ctgggaatgc | tgtccctgct | acacatcctc | acctgttgtc | tggatcctct | 1200 |
| tgctcctctc | ctgccttcca | tctggggccg | aacaccagcc | agctgtgtag | tctggctcca | 1260 |
| gctgactatt | cggcctgtgc | ccgttcaggc | cttgccctca | atcgatacag | cacatccttg | 1320 |
| gcagagacct | acagcaggct | taccaaccag | agcagtgaga | cctttgcccc | acctaggact | 1380 |
| ccttcctacg | tgagtgtgag | cagcaaccg | tctgtgaaca | tgtccatggg | cggcactgat | 1440 |
| ggggacacct | tcagctgccc | acagaccagc | ctgtccatgc | agatttcagg | aatgtccct | 1500 |
| caacttcagt | acatcatgcc | atcgccgtcc | ggcaatgcct | ttgctgctaa | ccagacccac | 1560 |
| cagagttctt | acaacaccctt | ccgattgcac | agtccctgtg | ccttgtatgg | atataacttc | 1620 |
| tccacatccc | ccaaactggc | tgccagtcct | gagaaaattg | tttcttccca | aggaagtttc | 1680 |
| ttggggtcct | caccaagtgg | gaccatgact | gatcgtcaga | tgttgcccc | tgtggaagga | 1740 |
| gtgcacctgc | tcagcagtgg | gggccagcag | agtttctttg | actccaggac | cctaggaagt | 1800 |
| ttaactctgc | catcttctca | agtgtctgca | catatggtct | ga | | 1842 |

<210> SEQ ID NO 2
<211> LENGTH: 957
<212> TYPE: DNA
<213> ORGANISM: Mus musculus

<400> SEQUENCE: 2

| | |
|---|---:|
| atgttcccca gccctgcgct cacacccacg cctttctcag tcaaagacat cctgaacctg | 60 |
| gagcagcagc agcgtagcct ggcgtctggg gacctgtctg cgcgcctcga ggccaccctg | 120 |
| gcccctgcct cctgcatgct ggccgccttc aagcccgagg cctactctgg ccccgaggcg | 180 |
| gcagcgtccg gcctggcaga gctgcgcgcg agatgggcc ccgcgccttc gccccccaag | 240 |
| tgctctcctg ctttcccagc cgcccccaca ttttacccgg gagcctacgg tgaccctgac | 300 |
| ccagccaaag accctcgggc ggataaaaaa gagctgtgcg cgctgcagaa ggcagtggag | 360 |
| ctggacaaag ccgagacgga tggcgccgag agaccacgcg cacggcggcg acggaagcca | 420 |
| cgcgtgctct tctcgcaggc gcaggtctac gagctggagc ggcgcttcaa gcaacagcgg | 480 |
| tacctgtcgg cgccagagcg cgaccagctg ccagcgtgc tgaagctcac gtccacgcag | 540 |
| gtcaagatct ggttccagaa ccgtcgctac aagtgcaagc gacagcggca ggaccagact | 600 |
| ctggagcttc tggggccgcc gccgccgccc gcgcgcagga tcgcggtgcc cgtgctggtg | 660 |
| cgcgacggga agccctgcct gggggacccc gcggcctacg ctcccgccta cggcgtgggt | 720 |
| ctcaatgcct atggctacaa cgcctacccc taccccagct acggcggcgc ggcctgcagt | 780 |
| cccggctaca gctgcgccgc ctaccccgct gcgccccccg ccgcgcagcc cccgccgcc | 840 |
| tccgccaaca gcaacttcgt gaactttggc gtcggggact tgaacaccgt gcagagtccc | 900 |
| gggatgccgc agggcaattc gggcgtctcc acgctgcacg gcatccgagc ctggtag | 957 |

<210> SEQ ID NO 3
<211> LENGTH: 1311
<212> TYPE: DNA
<213> ORGANISM: Mus musculus

<400> SEQUENCE: 3

| | |
|---|---:|
| atgagctcgc cgggcacaga gagcgcaggg aagagcctgc agtaccgagt ggaccacctg | 60 |
| ctcagcgccg tggagagcga gctgcaggcg ggcagcgaga agggagaccc caccgaacgc | 120 |
| gaactgcgag tgggcctgga ggagagcgag ctgtggctgc gcttcaagga gctaactaac | 180 |
| gagatgattg tgaccaagaa cggcaggagg atgttcccgg tgctgaaggt aaatgtgtca | 240 |
| ggcctggacc ccaatgccat gtactctttc ttgctggact cgtgacggc tgacaaccac | 300 |
| cgctggaaat atgtgaacgg ggagtgggta cctgggggca aaccagagcc tcaggcgccc | 360 |
| agctgcgtct acatccaccc agactcgccc aattttgggg cccactggat gaaggcgcct | 420 |
| gtgtctttca gcaaagtcaa actcaccaac aagctcaatg gaggggaca gatcatgtta | 480 |
| aactccttgc ataagtatga acctcggatt cacatcgtga gagttggggg cccgcaacgc | 540 |
| atgatcacca gccactgctt tcccgagacc cagttcatag ctgtgactgc ctaccagaat | 600 |
| gaggagatta cagcccttaa aattaaatac aacccatttg ctaaagcctt ccttgatgcc | 660 |
| aaagaaagaa acgaccacaa agatgtaatg gaggaaccgg gggactgcca gcagccgggg | 720 |
| tattcccaat gggggtggct tgttcctggt gctggcaccc tctgcccgcc tgccagctcc | 780 |
| caccctcagt ttggaggctc gctctctctc ccctccacac acggctgtga gaggtaccca | 840 |
| gctctaagga ccaccggtc atcgcccctac cccagcccct atgctcatcg aacagctct | 900 |
| ccaacctatg cggacaattc atctgcttgt ctgtccatgc tgcagtccca tgataactgg | 960 |
| tctagcctcg gagtgcctgg ccacaccagc atgctgcctg tgagtcataa cgccagccca | 1020 |
| cctactggct ctagccagta tcccagtctc tggtctgtga gcaatggtac catcaccca | 1080 |
| ggctcccaga cagctggggt gtccaacggg ctgggagctc agttctttcg aggctcccct | 1140 |

| | |
|---|---|
| gcacattaca caccactgac gcacacggtc tcagctgcca cgtcctcgtc ttctggttct | 1200 |
| ccgatgtatg aagggggctgc tacagtcaca gacatttctg acagccagta tgacacggcc | 1260 |
| caaagcctcc tcatagcctc gtggacacct gtgtcacccc catctatgtg a | 1311 |

```
<210> SEQ ID NO 4
<211> LENGTH: 807
<212> TYPE: DNA
<213> ORGANISM: Homo sapiens

<400> SEQUENCE: 4
```

| | |
|---|---|
| atggcccagc cctgtgccc gccgctctcc gagtcctgga tgctctctgc ggcctggggc | 60 |
| ccaactcggc ggccgccgcc ctccgacaag gactgcggcc gctccctcgt ctcgtcccca | 120 |
| gactcatggg gcagcacccc agccgacagc cccgtggcga gccccgcgcg gccaggcacc | 180 |
| ctccgggacc cccgcgcccc ctccgtaggt aggcgcggcg cgcgcagcag ccgcctgggc | 240 |
| agcgggcaga ggcagagcgc cagtgagcgg gagaaactgc gcatgcgcac gctggcccgc | 300 |
| gccctgcacg agctgcgccg ctttctaccg ccgtccgtgg cgcccgcggg ccagagcctg | 360 |
| accaagatcg agacgctgcg cctggctatc cgctatatcg ccacctgtc ggccgtgcta | 420 |
| ggcctcagcg aggagagtct ccagcgccgg tgccggcagc gcggtgacgc ggggtcccct | 480 |
| cggggctgcc cgctgtgccc cgacgactgc cccgcgcaga tgcagacacg gacgcaggct | 540 |
| gaggggcagg ggcaggggcg cgggctgggc ctggtatccg ccgtccgcgc cggggcgtcc | 600 |
| tggggatccc cgcctgcctg ccccggagcc cgagctgcac ccgagccgcg cgacccgcct | 660 |
| gcgctgttcg ccgaggcggc gtgccctgaa gggcaggcga tggagccaag cccaccgtcc | 720 |
| ccgctccttc cgggcgacgt gctggctctg ttggagacct ggatgcccct ctcgcctctg | 780 |
| gagtggctgc ctgaggagcc caagtga | 807 |

```
<210> SEQ ID NO 5
<211> LENGTH: 1113
<212> TYPE: DNA
<213> ORGANISM: Mus musculus

<400> SEQUENCE: 5
```

| | |
|---|---|
| atggcccagt cgcctcctcc tcagagcctc cagggtctcg accactgggt cttctcccag | 60 |
| ggctggggct gggctcagca atcggactcc acgtctccgg cctcgtcctc agattcgtcc | 120 |
| ggttcctgcc cttgctacgc caccgtcgg ccctcgcagc ccgccggccc ggcccgtagc | 180 |
| acgcgcacta cccaggcgac ggcgccccga cgaacgcgcc cagcgcccgc aggcggacag | 240 |
| cggcagagcg ccagcgagcg cgagaagctg cgcatgcgca cactcgcccg cgcgctgcaa | 300 |
| gaactgcgcc gcttcctgcc gccgtcggtg gcacctgcag gccagagcct gaccaagatc | 360 |
| gagacgctgc gcctggccat ccgctacatc ggccacctgt cagccctgct gggcctcagc | 420 |
| gaggacagtc tgcggcgcag gcgccgacgg agtgcggacg cggcgttctc tcaccgatgc | 480 |
| cctcaatgcc ccgacggtgg cagccctca caggctcaga tgcttggtcc tagcctggga | 540 |
| tcagccatga gtagtggggt gtcctggggg tgcccgcctg cttgtcctgg acctctgatc | 600 |
| tcacctgaaa accttgggaa caggatctcc aacgtggatc cctgggtgac acctccttat | 660 |
| tgtccccaaa tacagtcacc cttacaccag tccctagaaa gagccgctga ctcctctccc | 720 |
| tgggcaccac ctcaagcatg tcctggcatg cagatgtccc cagagcctag gaacaagact | 780 |
| ggacactgga cacaatccac tgaacctgca gagctgacta aagtgtatca gagtcttttct | 840 |
| gtgtctccag aaccctgcct gtccctggga agcccacttc tcctgccccg cccatcatgc | 900 |

| | |
|---|---|
| cagagactac agcctcagcc tcagcctcag cctcagtggg gctgctgggg ccacgatgca | 960 |
| gaggtgctct ccacctctga ggatcagggt tccagccctg ccctccagct tcctgtggcc | 1020 |
| agccccaccc ccagctcagg cctgcagctc agtggctgtc ctgaactttg caggaagac | 1080 |
| ctggaaggac ccccactgaa tattttctac taa | 1113 |

<210> SEQ ID NO 6
<211> LENGTH: 1557
<212> TYPE: DNA
<213> ORGANISM: Mus musculus

<400> SEQUENCE: 6

| | |
|---|---|
| atggccgata cagatgaggg cttttggcctg gcgcgcacgc tctggagcc tgattccaaa | 60 |
| gacaggtctt gcgattcgaa acctgagagt gctctggggg ctcccagcaa gtctccatca | 120 |
| tccccgcagg ctgccttcac ccagcagggc atggaaggaa tcaaggtgtt tcttcatgaa | 180 |
| cgtgaactgt ggctgaagtt ccacgaagtg gcacagaga tgatcatcac caaggcaggg | 240 |
| aggagaatgt ttcctagtta caaagtgaag gtgactggcc ttaatcccaa acgaagtat | 300 |
| attcttctca tggatattgt tcccgcagac gaccacagat ataaatttgc tgataacaaa | 360 |
| tggtccgtaa ctggcaaagc agagcctgcc atgccggggc gcctttacgt gcacccggac | 420 |
| tccccagcaa ccggagccca ctggatgcga caacttgtct ccttccagaa gctcaaactc | 480 |
| accaacaacc acctggaccc gtttggacac attatcctga actccatgca caaataccag | 540 |
| ccccgattac acatcgtgaa agcagacgaa aataatgggt tcggttcaaa gaacactgcg | 600 |
| ttttgcaccc acgtcttccc ggagacagct tttatcgctg tgacttcgta ccagaatcac | 660 |
| aagatcacac agctgaaaat tgagaacaac cccttcgcca aaggctttcg ggcagtgat | 720 |
| gacctggagt tacacaggat gtctcggatg caaagtaaag agtatcctgt ggttcccagg | 780 |
| agcacagtga ggcacaaagt cacctccaac cacagcccct tcagcagcga gacccgagct | 840 |
| ctctccacct catccaattt agggtcccag taccagtgtg agaatggtgt ctctggcccc | 900 |
| tcccaggacc ttctgccccc acctaaccca tacccactgg cccaggagca cagccaaatt | 960 |
| taccactgta ccaagaggaa agatgaggaa tgttccagca cggagcaccc ctataagaag | 1020 |
| ccgtacatgg agacatcccc cagcgaggaa gacaccttct atcgctcggg ctaccccag | 1080 |
| cagcagggcc tgagtacctc ttacaggaca gagtcggccc agcggcaggc ctgcatgtat | 1140 |
| gccagctccg ctcccccag cgagcccgtg cctagcctgg aggacatcag ctgtaacaca | 1200 |
| tggcccagca tgcctccta tagcagctgt accgtcacca ccgtgcagcc catgaccgt | 1260 |
| cttccctacc agcacttctc cgctcatttc acctcggggc ccctggtccc tcggttggct | 1320 |
| ggcatggcca accatggttc tccccagctc ggcgaaggga tgtttcagca ccagacctca | 1380 |
| gtggcccatc agcctgtggt caggcagtgc gggcctcaga ctggccttca gtctccgggc | 1440 |
| ggcctccagc cccagagtt tctctacact acgcgcgtgc ccaggaccct gtcccccat | 1500 |
| cagtatcact cggtacacgg cgtcggcatg gtgccagagt ggagtgagaa tagctaa | 1557 |

<210> SEQ ID NO 7
<211> LENGTH: 1050
<212> TYPE: DNA
<213> ORGANISM: Mus musculus

<400> SEQUENCE: 7

| | |
|---|---|
| atgggagaca tgggcgatcc accaaaaaaa aaacgtctga tttccctgtg tgttggttgc | 60 |

| | |
|---|---|
| ggcaatcaaa ttcacgacca gtatattctg agggtttctc cggatttgga gtggcatgca | 120 |
| gcatgtttga atgtgcgga gtgtaatcag tatttggacg aaagctgtac gtgctttgtt | 180 |
| agggatggga aaacctactg taaaagagat tatatcaggt tgtacgggat caaatgcgcc | 240 |
| aagtgcagca taggcttcag caagaacgac ttcgtgatgc gtgcccgctc taaggtgtac | 300 |
| cacatcgagt gttccgctg tgtagcctgc agccgacagc tcatcccggg agacgaattc | 360 |
| gccctgcggg aggatgggct tttctgccgt gcagaccacg atgtggtgga gagagccagc | 420 |
| ctgggagctg agaccctct cagtcccttg catccagcgc ggcctctgca atggcagcc | 480 |
| gaacccatct cggctaggca gccagctctg cggccgcacg tccacaagca gccggagaag | 540 |
| accacccgag tgcggactgt gctcaacgag aagcagctgc acaccttgcg gacctgctat | 600 |
| gccgccaacc ctcggccaga tgcgctcatg aaggagcaac tagtggagat gacgggcctc | 660 |
| agtcccagag tcatccgagt gtggtttcaa acaagcggt gcaaggacaa gaaacgcagc | 720 |
| atcatgatga agcagctcca gcagcagcaa cccaacgaca aaactaatat ccaggggatg | 780 |
| acaggaactc ccatggtggc tgctagtccg gagagacatg atggtggttt acaggctaac | 840 |
| ccagtagagg tgcaaagtta ccagccgccc tggaaagtac tgagtgactt cgccttgcaa | 900 |
| agcgacatag atcagcctgc ttttcagcaa ctggtcaatt tttcagaagg aggaccaggc | 960 |
| tctaattcta ctggcagtga agtagcatcg atgtcctcgc agctcccaga tacacccaac | 1020 |
| agcatggtag ccagtcctat tgaggcatga | 1050 |

<210> SEQ ID NO 8
<211> LENGTH: 1326
<212> TYPE: DNA
<213> ORGANISM: Mus musculus

<400> SEQUENCE: 8

| | |
|---|---|
| atgtaccaaa gcctggccat ggccgccaac cacggccccc cgcccggcgc ctacgaagca | 60 |
| ggtggccctg cgccttcat gcacagcgcg ggcgccgcgt cctcgcccgt ctacgtgccc | 120 |
| actccgcggg tgccgtcctc tgtgctgggc ctgtcctacc tgcagggcgg tggcagtgcc | 180 |
| gctgcagctg gaaccacctc gggtggcagc tccggggccg gccgtcggg tgcagggcct | 240 |
| gggacccagc agggtagccc tggctggagc caagctggag ccgagggagc cgcctacacc | 300 |
| ccgccgcccg tgtccccgcg cttctctttc ccggggacta ctgggtccct ggcggccgct | 360 |
| gccgccgctg ccgcagcccg ggaagctgca gcctacggca gtgcggcgg ggcggcgggc | 420 |
| gctggtctgg ctggccgaga gcagtacggg cgtccgggct cgccggctc ctactccagc | 480 |
| ccctacccag cctacatggc cgacgtggga gcatcctggg ccgcagccgc tgccgcctct | 540 |
| gccgcccct cgacagccc agtcctgcac agcctgcctg acgggccaa ccctggaaga | 600 |
| cacccaatc tcgatatgtt tgatgacttc tcagaaggca gagagtgtgt caattgtggg | 660 |
| gccatgtcca ccccactctg gaggcgagat gggacgggac actacctgtg caatgcctgt | 720 |
| ggcctctatc acaagatgaa cggcatcaac cggcccctca ttaagcctca gcgccgcctg | 780 |
| tccgcttccc gccgggtagg cctctcctgt gccaactgcc agactaccac caccacgctg | 840 |
| tggcgtcgta atgccgaggg tgagcctgta tgtaatgcct gcggcctcta catgaagctc | 900 |
| catggggttc ccaggcctct tgcaatgcgg aaggagggga ttcaaaccag aaaacggaag | 960 |
| cccaagaacc tgaataaatc taagacgcca gcaggtcctg ctggtgagac cctccctccc | 1020 |
| tccagtggtg cctccagcgg taactccagc aatgccacta gcagcagcag cagcagtgaa | 1080 |
| gagatgcgcc ccatcaagac agagcccggg ctgtcatctc actatgggca cagcagctcc | 1140 |

```
atgtcccaga cattcagtac tgtgtccggc cacgggccct ccatccatcc agtgctgtct   1200
gctctgaagc tgtccccaca aggctatgca tctcctgtca ctcagacatc gcaggccagc   1260
tccaagcagg actcttggaa cagcctggtc ctggctgaca gtcatgggga cataatcacc   1320
gcgtaa                                                              1326

<210> SEQ ID NO 9
<211> LENGTH: 1770
<212> TYPE: DNA
<213> ORGANISM: Mus musculus

<400> SEQUENCE: 9
atggccttga ctgacggcgg ctggtgcctg ccaaagcgtt tcgggctgc tgctgcggac      60 gccggcgact ccgggccctt ccagcgcgg gagccctcct cgccgctttc ccccatctcg     120
tcttcgtcct cctcctgctc ccggggcggg atcgcggtc cctgcggcgc agcaactgc      180 aggacgccgc agctcgacgc cgaggcgtg gcgggacctc cgggccgctc gctcttgctc    240
agcccctacg cctcgcatcc cttcgccgct gcccacggag ccgcggcgcc cggggtcgca    300 ggcccccggga gcgccctgtc gacttgggag gacctgttgc tcttcactga cctcgatcag   360
gccgcgaccg ccagcaagct gttgtggtcc agccggggcg ccaaactgag ccccttcgcg    420
gccgagcagc cggaggaaat gtaccagacc ctcgccgccc tgtccagcca ggggcccgcc    480
gcttacgacg gcgcgcccgg cggcttcgtg cactccgcag cggcggcggc cgctgccgcc    540
gcggcagcca gctccccggt ctacgtgccc accacgcgcg tgggctccat gctgtccggc    600
ctgccctacc ttcaaggggc gggcagcggg cccagcaatc acgcgggcgg agcgggtgcc    660
cacccaggct ggtcccaggc ctccgccgac agccccccgt atggcggggg tggcgcagcc    720
ggcggcggcg cggccggacc tggaggtgcg ggatcggcta cggcccacgc ctctgcacgc    780
tttccctact cgcccagccc gcccatggcc aacggcgccg cgcgagaccc cggggggctac    840 gtggctgcgg gcggcacggg cgcaggcagt gtgagtggag gtggcggcag cctggcggcc    900
atgggtggcc gggagcacca gtacagctcg ctgtccgcag ctcggccgct gaacggaacg    960
taccaccacc accatcacca tcacccgacc tactcgccct acatggccgc accgctgact   1020
cctgcctggc cagcaggacc cttcgaaacg ccggtgctcc acagcttaca gggccgcgcg   1080
ggagctccac tccggtgcc acggggcccc agcacagacc tgttggagga cctgtcggag   1140
agccgcgagt gcgtgaactg cggctccatc cagacgccac tgtggagacg agacggcacc   1200
ggtcattacc tgtgcaatgc atgcggtctc tacagcaaga tgaatggcct cagcaggccc   1260
ctcatcaagc cacagaagcg cgtgccttca tcacggcggc ttggactgtc ctgtgccaac   1320
tgtcacacca caaccactac cttatggcgt agaaatgctg agggtgagcc tgtgtgcaat   1380
gcttgcgggc tctatatgaa actccatggg gtgcctcgac cacttgctat gaaaaaagaa   1440
ggaattcaaa ccaggaaacg aaaacctaaa aatataaata agtcaaaagc ttgctccggt   1500
aacagcagtg gctctgtccc tatgactcct acttcctctt cttctaattc agatgactgc   1560
accaaaaata cttctccttc tacacaagcg accacctcag gggtaggggc atcagtgatg   1620
tctgcagtgg gagaaaacgc caaccccgag aacagtgacc tcaagtattc aggtcaagac   1680
ggcctctaca taggtgtcag tctgtcctcc cctgccgaag tcacatcctc cgtgcgacag   1740
gattcttggt gtgctctggc cctggcctga                                    1770

<210> SEQ ID NO 10
```

```
<211> LENGTH: 1560
<212> TYPE: DNA
<213> ORGANISM: Homo sapiens

<400> SEQUENCE: 10
atgtcctacc cgcagtttgg ataccectac tcctcggctc cccagttctt gatggccacc      60
aactccctga gcacgtgctg cgagtccgga ggccgcacgc tggcggactc cgggcccgcc     120
gcctcggccc aggcgccggt ctactgcccg gtctacgaga gccggctgct ggccaccgcg     180
cgccacgagc tcaactcggc cgcggcgctg ggcgtctatg ggggtcccta tggcggatcg     240
cagggctatg caactacgt gacctacggc tcggaggcgt ccgccttcta ctcgctgaac      300
agctttgatt ccaaggatgg ttcgggatct gcgcatgggg gcctggcacc agccactgcc     360
gcctactacc cttacgagcc agctctgggc cagtacccct atgacaggta tggaaccatg     420
gacagcggca cgcggcgcaa gaacgccacg cgcgagacca ccagcacgct caaggcctgg     480
ctgcaggagc accgcaagaa cccctacccc accaagggcg agaagatcat gctggccatc     540
atcaccaaga tgaccctcac acaggtctcc acctggttcg ccaacgcgcg ccggcgcctc     600
aagaaggaga caagatgac gtggccgccg cggaacaagt gcgcagacga gaagcggccc      660
tacgcggagg gcgaggagga ggaggggggc gaggaggagg cgcgggagga gccccctcaag   720 agctccaaga acgcagagcc cgtgggcaaa gaggagaagg agctggagct tagtgacttg     780
gacgacttcg acccgctgga agcagagccg ccggcgtgcg agctgaagcc gcccttccac     840
tccctggacg gcggtctgga gcgcgtcccc gccgcgcccg acggcccggt caaggaggcc     900
tcaggcgcgc tccggatgtc tctggccgcg ggtggcggag ctgctctgga cgaggacctg     960
gagagggccc ggagctgtct ccgcagcgcg gcggccgggc cggagccact gccgggcgca    1020
gagggcggcc ctcaggtctg cgaggccaag ctggggtttg tgccggcggg ggcgtcggca    1080
ggcctggagg ctaagccgcg catctggtcc ctggcccaca cagccaccgc cgccgccgcc    1140
gccgccacct ccctgagcca gactgagttt ccgtcgtgca tgctcaagcg ccaaggtccc    1200
gcggcccctg cggctgtgtc ctccgcgccc gccacgtccc cgtctgtggc ccttccccac    1260
tctggcgccc tggacaggca ccaggactcc ccggtaacca gtctcagaaa ctgggtggac    1320
ggggtcttcc acgaccccat cctcaggcac agcactttga accaggcctg gccaccgcc     1380 aagggcgccc tcctggaccc cgggcctctg gacgctcgc tggggcgggg cgcgaacgtg     1440
ctgactgcac ccctggcccg cgcctttccg cctgccgtgc cccaggacgc cccagctgca    1500
ggcgccgcca gggagctgct cgccctgccc aaggccggcg gcaaacccct ctgcgcctga    1560

<210> SEQ ID NO 11
<211> LENGTH: 1338
<212> TYPE: DNA
<213> ORGANISM: Mus musculus

<400> SEQUENCE: 11
atggagttca cggcgtcgcc caagccccag ctctcctctc gagccaatgc cttctccatc      60
gccgcgctta tgtccagcgg cggccccaag gagaaggagg cagcagagaa caccatcaaa     120
cccctggaac aatttgtgga gaaatcatca tgtgcccagc cactgggtga gctgacgagt     180
ctggatgctc acgcggagtt tggcggcggg ggcggcagcc atcctcatc ctctctgtgc      240 acagagccac tgatacccac caccccatc atccccagcg aagagatggc taaaatcgcc     300
tgcagcctgg aaacgaagga gctctgggac aaattccatg aactgggcac ggagatgata     360
atcaccaagt ctggcaggag gatgttcccc accatccgcg tgtcatttc tggagtggat     420
```

```
cctgagtcca agtatatagt cctgatggac atcgtcccgg tggacaacaa gagataccgc      480
tatgcctacc accggtcatc ctggctggtg gctggcaaag ctgatccccc gctgccagcc      540
aggctctacg tgcacccaga ctccccctt actggcgagc agctcctcaa acagatggtg       600
tcttttgaaa aggtgaagct caccaacaat gaactggatc aacacggcca tataattttg      660
aattcaatgc ataagtacca gccacgggtg cacatcataa agaagaaaga ccacacggcc      720
tccttgctca atctgaagtc agaagaattc aggacgttca tctttccaga dacagttttc     780
acagcagtca cagcctacca gaaccaactg ataaccaagc tgaaaataga cagcaatccg      840
tttgccaaag gattccggga ctcctccagg ctcactgaca ttgagaggga gagtgtggag     900
agcctgatcc agaagcattc ctatgcccgg tcacccatcc gcacctatgg ggaagaggat      960
gttctggggg aggagagtca gacaactcag agtcgaggat cagcctttac aacatctgac     1020
aatttgtctc tcagttcctg ggtatcatca tcttccagtt ttcctggatt tcagcatcca     1080
cagcccctga ctgctcttgg taccagtaca gcatccatag cgacaccgat tcctcaccct     1140
atacagggtt ctctgccacc atatagccgc ctgggaatgc ctctgacccc atctgcaata    1200
gccagctcca tgcagggaag tggtcccacg ttcccttcat tccacatgcc tagataccat    1260
cactacttcc agcaggggcc ctacgctgcc atccaaggac ttcgccactc ctccgctgtg    1320
atgacaccat ttgtatga                                                  1338

<210> SEQ ID NO 12
<211> LENGTH: 651
<212> TYPE: DNA
<213> ORGANISM: Mus musculus

<400> SEQUENCE: 12
atgaacctcg tgggcagcta cgcacatcat caccatcatc accactcaca cccgacgcac       60
cccatgctcc acgaacccct cctgtttggc ccggcctcgc gttgccacca ggagcggcct      120
tacttccaga gctggctgct gagcccggct gatgctgccc cagatttccc tgccggcggg      180
ccaccaccta ccaccgcagt agcagcggct gcctatggtc ccgatgccag gccgagtcag      240
agcccaggtc ggctggaggc tcttggaagc cgcctgccca acgaaaaggc tcaggaccc       300 aagaaggaga ggagacgcac agagagcatt aacagcgcgt cgcggagct gcgtgagtgc       360 atccccaatg tgcccgccga caccaagctc tccaagatca agactctgcg cctggctacc      420
agttacatcg cctacttgat ggacgtgctg gccaaggatg cacaagcagg tgaccccgag      480
gccttcaagg ctgaactcaa aaagacggat ggcggtcgcg aaagcaagcg gaaaggggag      540
ttgcctcagc agcccgaaag cttccctcct gcctcggggc cggcgagaa gaggattaaa      600 gggcgcaccg gctggcctca gcaagtctgg gcgctggagc taaaccagtg a              651

<210> SEQ ID NO 13
<211> LENGTH: 651
<212> TYPE: DNA
<213> ORGANISM: Mus musculus

<400> SEQUENCE: 13
atgaacctcg tgggcagcta cgcacatcat caccatcatc accactcaca cccgacgcac       60
cccatgctcc acgaacccct cctgtttggc ccggcctcgc gttgccacca ggagcggcct      120
tacttccaga gctggctgct gagcccggct gatgctgccc cagatttccc tgccggcggg      180
ccaccaccta ccaccgcagt agcagcggct gcctatggtc ccgatgccag gccgagtcag      240
```

```
agcccaggtc ggctggaggc tcttggaagc cgcctgccca acgaaaagg ctcaggaccc    300 aagaaggaga ggagacgcac agagagcatt aacagcgcgt tcgcggagct gcgtgagtgc    360
atccccaatg tgcccgccga caccaagctc tccaagatca agactctgcg cctggctacc    420
agttacatcg cctacttgat ggacgtgctg gccaaggatg cacaagcagg tgaccccgag    480
gccttcaagg ctgaactcaa aaagacggat ggcggtcgcg aaagcaagcg gaaaagggag    540
ttgcctcagc agcccgaaag cttccctcct gcctcggggc ccggcgagaa gaggattaaa    600
gggcgcaccg gctggcctca gcaagtctgg gcgctggagc taaaccagtg a             651

<210> SEQ ID NO 14
<211> LENGTH: 1422
<212> TYPE: DNA
<213> ORGANISM: Homo sapiens

<400> SEQUENCE: 14
atggggagaa aaaagattca gattacgagg attatggatg aacgtaacag acaggtgaca    60
tttacaaaga ggaaatttgg gttgatgaag aaggcttatg agctgagcgt gctgtgtgac    120
tgtgagattg cgctgatcat cttcaacagc accaacaagc tgttccagta tgccagcacc    180
gacatggaca aagtgcttct caagtacacg gagtacaacg agccgcatga gagccggaca    240
aactcagaca tcgtggagac gttgagaaag aagggcctta atggctgtga cagcccagac    300
cccgatgcgg acgattccgt aggtcacagc cctgagtctg aggacaagta caggaaaatt    360
aacgaagata ttgatctaat gatcagcagg caaagattgt gtgctgttcc acctcccaac    420
ttcgagatgc cagtctccat cccagtgtcc agccacaaca gtttggtgta cagcaaccct    480
gtcagctcac tgggaaaccc caacctattg ccactggctc acccttctct gcagaggaat    540
agtatgtctc ctggtgtaac acatcgacct ccaagtgcag gtaacacagg tggtctgatg    600
ggtggagacc tcacgtctgg tgcaggcacc agtgcaggga acgggtatgg caatccccga    660
aactcaccag gtctgctggt ctcacctggt aacttgaaca agaatatgca agcaaaatct    720 cctccccaa tgaatttagg aatgaataac cgtaaaccag atctccgagt tcttattcca    780
ccaggcagca gaatacgat gccatcagtg tctgaggatg tcgacctgct tttgaatcaa    840
aggataaata actcccagtc ggctcagtca ttggctaccc cagtggtttc cgtagcaact    900
cctactttac caggacaagg aatgggagga tatccatcag ccatttcaac aacatatggt    960
accgagtact ctctgagtag tgcagacctg tcatctctgt ctgggtttaa caccgccagc    1020
gctcttcacc ttggttcagt aactggctgg caacagcaac acctacataa catgccacca    1080
tctgccctca gtcagttggg agcttgcact agcactcatt tatctcagag ttcaaatctc    1140
tccctgcctt ctactcaaag cctcaacatc aagtcagaac ctgtttctcc tcctagagac    1200
cgtaccacca cccttcgag atacccacaa cacacgcgcc acgaggcggg gagatctcct    1260
gttgacagct tgagcagctg tagcagttcg tacgacggga gcgaccgaga ggatcaccgg    1320
aacgaattcc actcccccat ggactcacc agaccttcgc cggacgaaag ggaaagtccc    1380
tcagtcaagc gcatgcgact ttctgaagga tgggcaacat ga                       1422

<210> SEQ ID NO 15
<211> LENGTH: 1413
<212> TYPE: DNA
<213> ORGANISM: Homo sapiens

<400> SEQUENCE: 15
atgactccag gtcttcagca cccacccacc gtggtacagc gccccgggat gccgtctgga    60
```

```
gcccggatgc cccaccaggg ggcgcccatg ggccccccgg gctcccgta catgggcagc      120 cccgccgtgc gacccggcct ggcccccgcg ggcatggagc ccgcccgcaa gcagcagcg      180 cccccgcccg ggcagagcca ggcacagagc cagggccagc cggtgcccac cgccccgcg      240 cggagccgca gtgccaagag gaggaagatg gctgacaaaa tcctccctca aaggattcgg    300
gagctggtcc ccgagtccca ggcttacatg gacctcttgg catttgagag gaaactggat    360
caaaccatca tgcggaagcg ggtggacatc caggaggctc tgaagaggcc catgaagcaa    420
aagcggaagc tgcgactcta tatctccaac acttttaacc ctgcgaagcc tgatgctgag    480
gattccgacg gcagcattgc ctcctgggag ctacgggtgg aggggaagct cctggatgat    540
cccagcaaac agaagcggaa gttctcttct ttcttcaaga gtttggtcat cgagctggac    600
aaagatcttt atggccctga caaccacctc gttgagtggc atcggacacc cacgacccag    660
gagacggacg gcttccaggt gaaacggcct ggggacctga gtgtgcgctg cacgctgctc    720
ctcatgctgg actaccagcc tccccagttc aaactggatc cccgcctagc ccggctgctg    780
gggctgcaca cacagagccg ctcagccatt gtccaggccc tgtggcagta tgtgaagacc    840
aacaggctgc aggactccca tgacaaggaa tacatcaatg gggacaagta tttccagcag    900
atttttgatt gtccccggct gaagtttttct gagattcccc agcgcctcac agccctgcta    960 ttgcccctg acccaattgt catcaaccat gtcatcagcg tggacccttc agaccagaag    1020
aagacggcgt gctatgacat tgacgtggag gtggaggagc cattaaaggg gcagatgagc    1080
agcttcctcc tatccacggc caaccagcag gagatcagtg ctctggacag taagatccat    1140
gagacgattg agtccataaa ccagctcaag atccagaggg acttcatgct aagcttctcc    1200
agagacccca aaggctatgt ccaagacctg ctccgctccc agagccggga cctcaaggtg    1260
atgacagatg tagccggcaa ccctgaagag gagcgccggg ctgagttcta ccaccagccc    1320
tggtcccagg aggccgtcag tcgctacttc tactgcaaga tccagcagcg caggcaggag    1380
ctggagcagt cgctggttgt gcgcaacacc tag                                 1413
```

<210> SEQ ID NO 16
<211> LENGTH: 1020
<212> TYPE: DNA
<213> ORGANISM: Mus musculus

<400> SEQUENCE: 16

```
atgaagcgcc cttgtgagga acgacctcc gaaagcgacc tggacgagac catcgacgtg       60
gggagcgaga acaattaccc tgggcacgct acaagctcag tgatgaggtc caattcaccg    120
acaactacct ctcagattat ggcaagaaag aaaaggagag ggatcataga aaaaaggcgt    180
cgggatcgaa taataacag tttatctgaa ttgagaagac tagtgccaac agcttttgaa    240
aaacaaggat ctgccaagtt agaaaaggct gaaatattgc aaatgacagt ggatcatttg    300
aagatgctcc aggctacagg gggtaaaggc tactttgatg cccatgctct tgccacagac    360
ttcatgagca ttggattccg agagtgcttg acagaagtgg ctaggtacct aagctcagtg    420
gaaggccttg acccgtcgga cccactacgc gtgcgccttg tctctcatct cagcacctgt    480
gcctcccagc gggaggcagc agtgatgaca tcctccatgg cccaccacca tcacccttg    540 caccctcacc actgggcagc tgctttccac catctcccca cagccctgct ccagcccaat    600
ggactccaca catcagagtc aaccccatgt cgcctatcca catcttcaga agtgccttct    660
gctcatggct ctgctctcct cacagcaacg tttgcccatg cagattctgc tcttcggatg    720
```

| | |
|---|---|
| ccatcagggg gcaccgttgc accctgcgtg ccacctctct ccacctctct tctgtctctt | 780 |
| tcggccactg tgcatgccgc agctgcagca gccactgcag ctgcacacag cttccctctg | 840 |
| tccttcgcag gggcttttcc catgctcccg tccaatgcag cggcagcagc cgctgttgct | 900 |
| gctgcaacag caatcagccc acccttgtcg gtatccgcag cctccagtcc tcagcagaca | 960 |
| agcactggga caaacaataa accttaccaa ccctggggga cagaagttgg agccttttaa | 1020 |

<210> SEQ ID NO 17
<211> LENGTH: 1527
<212> TYPE: DNA
<213> ORGANISM: Homo sapiens

<400> SEQUENCE: 17

| | |
|---|---|
| atgttaccga cccaagctgg ggccgcggcg gctctgggcc ggggctcggc cctgggggc | 60 |
| agcctgaacc ggaccccgac ggggcggccg ggcggcggcg gcgggacacg cggggctaac | 120 |
| gggggccggg tccccgggaa tggcgcgggg ctcgggcccg ccgcctgga gcggaggct | 180 |
| gcggcagcgg cggcaaccac cccggcgccc accgcggggg ccctctacag cggcagcgag | 240 |
| ggcgactcgg agtcgggcga ggaggaggag ctgggcgccg agcggcgcgg cctgaagcgg | 300 |
| agcctgagcg agatggagat cggtatggtg gtcggtgggc ccgaggcgtc ggcagcggcc | 360 |
| accgggggct acgggccggt gagcggcgcg gtgagcgggg ccaagccggg taagaagacc | 420 |
| cggggccgcg tgaagatcaa gatggagttc atcgacaaca gctgcgcgcg ctacacgacc | 480 |
| ttcagcaaga ggaagacggg catcatgaag aaggcctatg agctgtccac gctgacaggg | 540 |
| acacaggtgc tgttgctggt ggccagtgag acaggccatg tgtataccct tgccacccga | 600 |
| aaactgcagc ccatgatcac cagtgagacc ggcaaggcac tgattcagac ctgcctcaac | 660 |
| tcgccagact ctccaccccg ttcagacccc acaacagacc agagaatgag tgccactggc | 720 |
| tttgaagaga cagatctcac ctaccaggtg tcggagtctg acagcagtgg ggagaccaag | 780 |
| gacacactga agccggcgtt cacagtcacc aacctgccgg gtacaacctc caccatccaa | 840 |
| acagcaccta gcacctctac caccatgcaa gtcagcagcg cccctccctt tcccatcacc | 900 |
| aactacctgg caccagtgtc tgctagtgtc agccccagtg ctgtcagcag tgccaatggg | 960 |
| actgtgctga gagtacagg cagcggccct gtctcctctg ggggccttat gcagctgcct | 1020 |
| accagcttca ccctcatgcc tggtgggca gtggcccagc aggtcccagt gcaggccatt | 1080 |
| caagtgcacc aggccccaca gcaagcgtct ccctcccgtg acagcagcac agacctcacg | 1140 |
| cagacctcct ccagcgggac agtgacgctg cccgccacca tcatgacgtc atccgtgccc | 1200 |
| acaactgtgg gtggccacat gatgtaccct agcccgcatg cggtgatgta tgcccccacc | 1260 |
| tcgggcctgg gtgatggcag cctcaccgtg ctgaatgcct tctcccaggc accatccacc | 1320 |
| atgcaggtgt cacacagcca ggtccaggag ccaggtggcg tcccccaggt gttcctgaca | 1380 |
| gcatcatctg ggacagtgca gatccctgtt tcagcagttc agctccacca gatggctgtg | 1440 |
| atagggcagc aggccgggag cagcagcaac ctcaccgagc tacaggtggt gaacctggac | 1500 |
| accgcccaca gcaccaagag tgaatga | 1527 |

<210> SEQ ID NO 18
<211> LENGTH: 1542
<212> TYPE: DNA
<213> ORGANISM: Mus musculus

<400> SEQUENCE: 18

| | |
|---|---|
| atggcggagg tgggggagat aatcgagggc tgccgcctgc ccgtgctgcg gcgcaaccag | 60 |

```
gacaacgaag atgagtggcc cctggctgag atcctgagcg tgaaggacat cagtggccga      120
aagcttttct atgtccatta cattgacttc aacaaacgtc tggatgaatg ggtgactcac      180
gagcggctgg acttaaagaa gatccaattt cccaagaaag aggccaagac acctaccaag      240
aacggacttc ctgggtcccg ccccggctct cccgaaagag aggtgccggc ctccgcccag      300
gccagcggga agaccttgcc aatcccggtc cagatcacac tccgcttcaa cctgcccaag      360
gagcgggagg ccatcccagg tggcgagcct gaccagccgc tctcctccag ctcctgcctg      420
caacccaacc accgctcaac gaaacggaag gtggaggtgg tttcaccagc aaccccagtg      480
cccagcgaga cagccccagc ctcggttttc cctcagaatg ggtcagcccg tagggcagtg      540
gcagcccagc ctggacggaa gcggaaatct aattgcttgg cactgatga ggattctcag      600 gacagctcag atggaatacc gtcagcacca cgaatgactg gcagtctggt gtctgaccgg      660
agccacgacg acattgtcac ccggatgaag aacattgagt gtattgagct tggccggcac      720
cgcctcaagc gtggtacttt ctccccgtac ccacaagagc ttaccacgct acccgtcctc      780
tacctgtgcg aattttgcct caaatatggc cgtagcctca gtgtctgca cgccacttg      840 accaaatgtg atcttcggca ccctccaggc aatgaaattt accgcaaggg caccatctcc      900
ttttttgaga ttgatggacg gaaaaacaag agttactcac aaaacctgtg tcttctggcc      960
aagtgtttcc tggaccacaa aacactgtac tatgacactg accccttcct cttctacgta     1020
atgacggagt atgactgcaa aggtttccac atcgtgggct acttctccaa ggaaaaggaa     1080
tccacagaag attacaatgt ggcctgcatc ttgactctgc ctccctacca cgccggggc     1140 tatggcaagc tgcttattga gttcagctat gaactctcga agtagaagg gaagaccgga     1200 actcctgaga aaccccctgtc agatcttggc ctcctatcct accgaagtta ctggtcccaa     1260
accatcttgg agatcctgat ggggctgaag tcggagagcg gggagaggcc acagatcacc     1320
atcaatgaga tcagtgaaat cactagtatc aagaaagaag atgtcatctc cacactgcag     1380
tatctcaacc tcatcaatta ctacaagggc cagtatatcc taactctgtc agaagacatc     1440
gtggatgggc atgagcgggc tatgctcaag cggctccttc ggattgactc caagtgtctg     1500
cacttcactc ccaaagactg gagcaagaga ggaaagtggt ga                       1542

<210> SEQ ID NO 19
<211> LENGTH: 1059
<212> TYPE: DNA
<213> ORGANISM: Mus musculus

<400> SEQUENCE: 19
atggctggac acctggcttc agacttcgcc ttctcacccc caccaggtgg gggtgatggg       60 tcagcaggg tggagccggg ctgggtggat cctcgaacct ggctaagctt ccaagggcct      120
ccaggtgggc ctggaatcgg accaggctca gaggtattgg ggatctcccc atgtccgccc      180
gcatacgagt tctgcggagg gatggcatac tgtggacctc aggttggact gggcctagtc      240
ccccaagttg gcgtggagac tttgcagcct gagggccagg caggagcacg agtggaaagc      300
aactcagagg gaacctcctc tgagccctgt gccgaccgcc caatgccgt gaagttggag      360 aaggtggaac caactcccga ggagtcccag gacatgaaag ccctgcagaa ggagctagaa      420
cagtttgcca agctgctgaa gcagaagagg atcaccttgg ggtacaccca ggccgacgtg      480
gggctcaccc tgggcgttct ctttggaaag gtgttcagcc agaccaccat ctgtcgcttc      540
gaggccttgc agctcagcct taagaacatg tgtaagctgc ggcccctgct ggagaagtgg      600
```

```
gtggaggaag ccgacaacaa tgagaacctt caggagatat gcaaatcgga gaccctggtg      660
caggcccgga agagaaagcg aactagcatt gagaaccgtg tgaggtggag tctggagacc      720
atgtttctga agtgcccgaa gccctcccta cagcagatca ctcacatcgc caatcagctt      780
gggctagaga aggatgtggt tcgagtatgg ttctgtaacc ggcgccagaa gggcaaaaga      840
tcaagtattg agtattccca acgagaagag tatgaggcta cagggacacc tttcccaggg      900
ggggctgtat cctttcctct gcccccaggt ccccactttg gcaccccagg ctatggaagc      960
ccccacttca ccacactcta ctcagtccct tttcctgagg gcgaggcctt tccctctgtt     1020
cccgtcactg ctctgggctc tcccatgcat tcaaactga                            1059
```

<210> SEQ ID NO 20
<211> LENGTH: 1425
<212> TYPE: DNA
<213> ORGANISM: Mus musculus

<400> SEQUENCE: 20

```
atggctgtca gcgacgctct gctcccgtcc ttctccacgt tcgcgtccgg cccggcggga       60
agggagaaga cactgcgtcc agcaggtgcc ccgactaacc gttggcgtga ggaactctct      120
cacatgaagc gacttccccc acttcccggc cgccctacg acctggcggc gacggtggcc       180
acagacctgg agagtggcgg agctggtgca gcttgcagca gtaacaaccc ggccctccta      240
gcccggaggg agaccgagga gttcaacgac ctcctggacc tagactttat cctttccaac      300
tcgctaaccc accaggaatc ggtggccgcc accgtgacca cctcggcgtc agcttcatcc      360
tcgtcttccc cagcgagcag cggccctgcc agcgcgccct ccacctgcag cttcagctat      420
ccgatccggg ccggggtga cccgggcgtg gctgccagca acacaggtgg agggctcctc      480
tacagccgag aatctgcgcc acctcccacg gccccttca acctggcgga catcaatgac      540
gtgagcccct cgggcggctt cgtggctgag ctcctgcggc ggagttgga cccagtatac      600 attccgccac agcagcctca gccgccaggt ggcgggctga tgggcaagtt tgtgctgaag      660
gcgtctctga ccacccctgg cagcgagtac agcagccctt cggtcatcag tgttagcaaa      720
ggaagcccag acggcagcca ccccgtggta gtggcgccct acagcggtgg cccgccgcgc      780
atgtgcccca agattaagca agaggcggtc ccgtcctgca cggtcagccg gtccctagag      840 gcccattttga gcgctggacc ccagctcagc aacggccacc ggcccaacac acacgacttc      900
cccctggggc ggcagctccc caccaggact accctacac tgagtcccga ggaactgctg      960
aacagcaggg actgtcaccc tggcctgcct cttcccccag gattccatcc catccgggg     1020 cccaactacc ctcctttcct gccagaccag atgcagtcac aagtcccctc tctccattat     1080
caagagctca tgccaccggg ttcctgcctg ccagaggagc ccaagccaaa gaggggaaga     1140
aggtcgtggc cccggaaaag aacagccacc cacacttgtg actatgcagg ctgtggcaaa     1200
acctatacca agagttctca tctcaaggca cacctgcgaa ctcacacagg cgagaaacct     1260
taccactgtg actgggacgg ctgtgggtgg aaattcgccc gctcggatga actgaccagg     1320
cactaccgca aacacacagg gcaccggccc tttcagtgcc agaagtgcga cagggccttt     1380
tccaggtcgg accaccttgc cttacacatg aagaggcact tttaa                    1425
```

<210> SEQ ID NO 21
<211> LENGTH: 1107
<212> TYPE: DNA
<213> ORGANISM: Mus musculus

<400> SEQUENCE: 21

-continued

| | |
|---|---|
| atggacttcg actcgtatca gcactatttc tacgactatg actgcggaga ggatttctac | 60 |
| cgctccacgg cgcccagcga ggacatctgg aagaaattcg agctggtgcc gtcgcccccc | 120 |
| acgtcgccgc cctggggctc cggtcccggc gccgtggacc cagcctctgg gattaatccc | 180 |
| ggggagccgt ggcctggagg gggtgccggg gacgaggcgg aatctcgggg ccattcgaaa | 240 |
| gcctggggca ggaattatgc ttccatcatt cgccgtgact gcatgtggag cggcttctcc | 300 |
| gcccgagaac ggctggagag agtggtgagc gacaggctgg ccccaggcgc gccccggggg | 360 |
| aacccgccca agcgcccgc taccccggac ggcactccta gtctggaagc cagtaacccg | 420 |
| gcgcccgcca cccaatgtca gctgggcgag cccaagactc aggcctgctc cgggtccgag | 480 |
| agccccagcg attctgaagg tgaagagatt gacgtggtga ccgtggagaa gaggcgatct | 540 |
| ctggacatcc gaaagccagt caccatcacg gtgcgagcag accccctgga ccccctgcatg | 600 |
| aagcacttcc atatctctat ccaccaacag cagcataact atgctgcccg ttttcctcca | 660 |
| gaaagttgct ctcaagaggg ggatcctgag ccaggtcccc aggaagaggc tccggagata | 720 |
| gaagctccca aggagaaaga ggaggaggaa gaggaagagg aggaagaaga gattgtgagc | 780 |
| cccccacctg tcggaagtga ggctccccag tcctgccacc ccaaacctgt cagttctgac | 840 |
| actgaggacg tgaccaagag gaagaaccat aacttcttgg aacgaaaaag gaggaatgac | 900 |
| ctccgctccc ggttcctagc cctgcggac caggttccca ccctggccag ctgctctaag | 960 |
| gccccccaaag tcgtgatcct cagcaaggcg ttagaatact tgcaggcttt ggtgggggct | 1020 |
| gaaaagaaaa tggctacaga gaaaaggcag ctccggtgtc ggcaacagca actgcaaaag | 1080 |
| agaatcgcgt acctcagtgg ctactaa | 1107 |

<210> SEQ ID NO 22
<211> LENGTH: 960
<212> TYPE: DNA
<213> ORGANISM: Mus musculus

<400> SEQUENCE: 22

| | |
|---|---|
| atgtataaca tgatggagac ggagctgaag ccgccgggcc cgcagcaagc ttcgggggggc | 60 |
| ggcggcggag gaggcaacgc cacggcggcg gcgaccggcg gcaaccagaa gaacagcccg | 120 |
| gaccgcgtca agaggcccat gaacgccttc atggtatggt cccgggggca gcggcgtaag | 180 |
| atggcccagg agaaccccaa gatgcacaac tcggagatca gcaagcgcct gggcgcggag | 240 |
| tggaaacttt tgtccgagac cgagaagcgg ccgttcatcg acgaggccaa gcggctgcgc | 300 |
| gctctgcaca tgaaggagca cccggattat aaataccggc gcggcggaa aaccaagacg | 360 |
| ctcatgaaga aggataagta cacgcttccc ggaggcttgc tggccccgg cgggaacagc | 420 |
| atggcgagcg gggttgggggt gggcgccggc ctgggtgcgg gcgtgaacca gcgcatggac | 480 |
| agctacgcgc acatgaacgg ctggagcaac ggcagctaca gcatgatgca ggagcagctg | 540 |
| ggctaccccgc agcacccggg cctcaacgct cacggcgcgg cacagatgca accgatgcac | 600 |
| cgctacgacg tcagcgccct gcagtacaac tccatgacca gctcgcagac ctacatgaac | 660 |
| ggctcgccca cctacagcat gtcctactcg cagcagggca cccccggtat ggcgctgggc | 720 |
| tccatgggct ctgtggtcaa gtccgaggcc agctccagcc ccccgtggt tacctcttcc | 780 |
| tcccactcca gggcgccctg ccaggccggg gacctccggg acatgatcag catgtacctc | 840 |
| cccgcgccg aggtgccgga gcccgctgcg cccagtagac tgcacatggc ccagcactac | 900 |
| cagagcggcc cggtgcccgg cacggccatt aacggcacac tgcccctgtc gcacatgtga | 960 |

LINEAGE REPROGRAMMING TO INDUCED CARDIAC PROGENITOR CELLS (ICPC) BY DEFINED FACTORS

CROSS-REFERENCE TO RELATED APPLICATIONS

This application claims the benefit of U.S. Provisional Patent Application No. 61/904,881, filed Nov. 15, 2013; which is incorporated herein by reference as if set forth in its entirety.

STATEMENT REGARDING FEDERALLY SPONSORED RESEARCH OR DEVELOPMENT

This invention was made with government support under HL099773 awarded by the National Institutes of Health. The government has certain rights in the invention.

BACKGROUND

Several studies have reported reprogramming of animal fibroblasts to induced cardiomyocytes (iCM). However, reprogramming to proliferative and multipotent cardiac progenitor cells (CPC) may be more favorable for cell therapy and research applications for several reasons. iCM have not been shown to be proliferative in culture, thereby limiting the available source of cardiomyocytes (CM) for therapeutic use. Moreover, cardiac cells other than CM might be therapeutically important, but these are not present when iCM are used.

Human pluripotent cells, including human embryonic stem cells (ESC) and human induced pluripotent cells (iPSC), have been differentiated in culture with three soluble factors to produce induced cardiac progenitor cells (iCPC). Cao, et al., "Highly efficient induction and long-term maintenance of multipotent cardiovascular progenitors from human pluripotent stem cells under defined conditions," *Cell Res.* 23:1119 (2013). It may be impractical to routinely employ such pluripotent cells as starting material for making therapeutic quantities of iCPC, either because of ethical considerations of using embryonic stem cells, or because of the considerable time and effort required to obtain suitable iPSC. Islas et al, *PNAS USA* 109:13016-21 (Aug. 7, 2012) (and U.S. Pat. No. 8,486,701) was said to have produced iCPC from human fibroblasts, but the isolated cells did not meet the criteria of proliferation and differentiation into cardiac lineage cells that define cardiac progenitor cells.

Additional approaches are still needed for obtaining proliferative and multipotent iCPC for research or therapeutic use.

BRIEF SUMMARY

A method for producing induced cardiac progenitor cells (iCPC) from mammalian somatic cells includes the steps of:
expressing in the somatic cells a set of factors sufficient to induce reprogramming of the cells to iCPC; and
separating the iCPC from non-reprogrammed somatic cells.

In certain embodiments, the mammalian somatic cells are obtained from a human or from a rodent.

In certain embodiments, the set of factors includes a plurality of early cardiac transcription factors. In some embodiments, the plurality of early cardiac transcription factors includes some or all of Mesp1, Baf60c, Nkx2.5, Gata4, and Tbx5. In other embodiments, the plurality includes some or all of Mesp1, Mesp2, Gata4, Gata6, Baf60c, SRF, Isl1, Nkx2.5, Irx4, Tbx5, and Tbx20. Other pluralities include some or all of T, Mesp1, Mesp2, Tbx5, Tbx20, Isl1, Gata4, Gata6, Irx4, Nkx2.5, Hand1, Hand2, Tbx20, Tbx18, Tip60, Baf60c, SRF, and Hey2. In some embodiments, the factors are encoded by nucleic acid obtained from at least one of a human animal and a non-human animal.

The set of factors can be provided on vectors in an expression library. In some embodiments the vectors are viral (e.g., lentiviral, retroviral, adenoviral, baculoviral) vectors. In other embodiments, the vectors are non-viral vectors such as non-viral episomal vectors, cationic liposomes, neutral liposomes, polymer-nucleic acid complexes (e.g., polymer nanoparticles, dendrimers), and peptide-nucleic acid complexes.

In some embodiments, the expressing step includes the step of exposing the somatic cells to an expression library configured to encode the set of factors. In other embodiments, direct exposure of the cells to the factors per se, and interaction between the cells and the factors may suffice to achieve reprogramming to iCPC. Exposure to every member of the set of factors may not be essential to achieving reprogramming to iCPC.

In some embodiments, the exposing step includes the step of introducing the set of factors into the somatic cells by transfection or other known methods for introduction of genetic material into mammalian somatic cells.

In some embodiments, expression of the set of factors can require induction of expression by exposure of the somatic cells into which the factors were introduced to an inducing agent such as doxycycline in the expression system described herein. The inducing agent can be provided in the culture medium or by any other operable delivery route.

In some embodiments, additional components are advantageously employed in the method to facilitate proliferation of the iCPC. In some embodiments, a suitable component is an activator of canonical Wnt signaling such as 6-bromoindirubin-3'-oxime (BIO). In other embodiments, suitable components include an activator of canonical Wnt signaling and an activator of Jak/Stat signaling such as Leukemia Inhibitory Factor (LIF). In each case the additional component or components are provided in amounts, or at concentrations, sufficient to facilitate proliferation of the iCPC.

In some embodiments, somatic cells to be reprogrammed can be provided with a marker that is selectively expressed only in cells of the desired state, here cells characterized as CPC. In certain embodiments, the somatic cells can contain a stable marker-encoding transgene under control of a CPC-specific regulatory sequence where the transgene produces a detectable product only when the cells are CPC, or in this case induced CPC. A suitable marker-encoding transgene can encode fluorescent protein such as, but not limited to eYFP or eGFP.

In some embodiments, the iCPC can be separated from non-reprogrammed cells by cell sorting on the basis of a cell surface marker characteristic of one cell type or the other, or by another known method for separating cells having distinguishable attributes, including by splitting the cultures such that non-reprogrammed cells, which do not proliferate, are outcompeted by the proliferative, reprogrammed cells. Alternatively, reprogrammed cells can be manually dissected from non-reprogrammed cells on the basis of fluorescence and other morphological differences.

Nucleic acids encoding sets of factors sufficient to reprogram somatic cells to iCPC by direct lineage reprogramming can be provided as kits, as can libraries that include viral or non-viral nucleic acid vectors engineered to express some or all of the encoded factors upon transfer into the somatic mammalian cells.

In another aspect, provided herein is an in vitro population of induced cardiac progenitor cells produced according to a method provided herein.

In a further aspect, provided herein is a culture comprising an in vitro population of induced cardiac progenitor cells produced according to a method provided herein.

These and other features, aspects, and advantages described herein will become better understood upon consideration of the following detailed description, drawings, and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the descriptions of the drawings and the Examples section below, all work was done with mouse cells unless human is specified.

FIG. 4 presents gene ontology analysis performed for upregulated and downregulated genes in late passage iCPCs as compared to AC Fibs.

FIG. 13 presents defined factors used for iCPC reprogramming screen.

DETAILED DESCRIPTION

Figure 1:
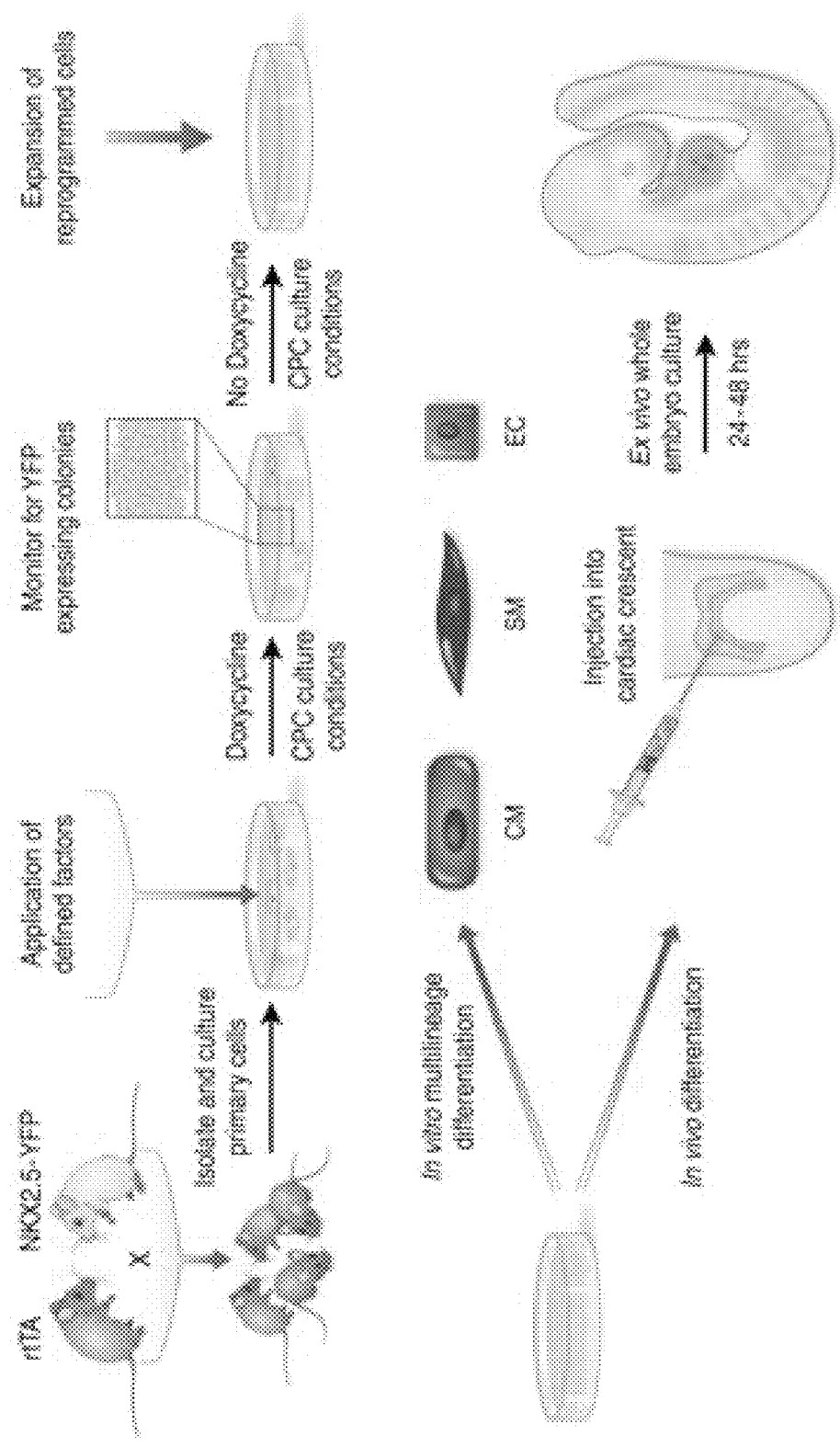
FIG. 1 depicts a screen for identifying iCPC inducing factors and optimal culture conditions. (A) Schematic representation of experimental design depicting direct reprogramming of iCPCs by defined factors and culture conditions, expansion of iCPCs, and in vitro as well as in vivo differentiation of iCPCs into cardiac-lineage cells. (B) Infection with a combination of 11 cardiac factors induced Nkx2.5-EYFP expression in adult cardiac fibroblasts (AC Fibs) only after dox induction. (C) 11-factor infected AC Fibs developed into two dimensional, proliferative colonies of EYFP+ cells. Images taken 3 weeks after dox treatment show a colony of reprogrammed EYFP+ cells, surrounded by EYFP− fibroblasts. (D) Images show the striking morphological difference between EYFP+ reprogrammed cells and EYFP− fibroblasts (indicated by *). Reprogrammed cells lost parental fibroblast morphology and exhibited a high nuclear-cytoplasmic ratio. (E) Strategy to test impact of culture conditions on F11 reprogramming efficiency as well as the ability of EYFP+ reprogrammed cells to maintain a proliferative state. (F) Number of EYFP+ colonies formed (per 50,000 starting cells) in the respective culture conditions (**p<0.01, *p<0.05). (G) Impact of culture conditions on EYFP+ colonies expanded up to 5 passages scoring for EYFP+ expression and proliferative ability (Dox only: n=8, Dox+LIF: n=3, Dox+BIO: n=4, Dox+LIF+BIO: n=9). (L=LIF, B=BIO). Data presented as mean. Error bars=SEM. Scale bar=100 μm in B, 500 μm in C and D.

All publications, patents, and patent applications mentioned in this specification are herein incorporated by reference in their entirety as if each individual publication, patent, and patent application was specifically and individually indicated to be incorporated by reference.

Several studies have reported reprogramming of fibroblasts to induced cardiomyocytes. However, reprogramming to proliferative induced cardiac progenitor cells (iCPCs), which are favorable for cardiac repair because of their expandability and multipotency, had not been accomplished prior to the Inventors' discovery. Described for the first time, therefore, are methods for producing a scalable source of clinically relevant cardiac lineage progenitor cells useful for numerous applications including cardiac regenerative therapy, drug discovery, and disease modeling. Lineage reprogramming of adult somatic cells into iCPCs provides a scalable cell source for cardiac regenerative therapy, drug discovery, and disease modeling. Accordingly, the present invention is based at least in part on the Inventors' discovery of defined factors capable of stably reprogramming somatic cells to cardiac lineage-restricted progenitors that can be extensively passaged and expanded in culture and that show multipotency toward cardiovascular lineages. Also provided herein are novel methods for reprogramming differentiated somatic cells into expandable populations of multipotent cardiac progenitor cells.

In a first aspect, provided herein are methods for producing induced cardiac progenitor cells (iCPCs) from somatic cells. In exemplary embodiments the method includes expressing in the somatic cells a set of factors sufficient to induce reprogramming of the cells to produce iCPC; and separating the iCPC from non-reprogrammed cells. As used herein, the terms "induced cardiac progenitor cell" and "iCPC" refer to proliferative and expandable progenitor cells that maintain multipotency to differentiate into cardiomyocytes, smooth muscle cells, and endothelial cells. As used herein, the term "proliferative" refers to the capacity of a iCPC to increase in cell number in culture and give rise to more progenitor cells having the ability to generate a large number of mother cells. Proliferative cardiac progenitor cells are identifiable based on some or all of the following properties: actively cycling; capable of self-renewal; premitotic arrest; able to differentiate into terminally derived cardiac cell types (e.g., functional cardiomyocytes); express markers (e.g., biomarkers) characteristic of cardiac progenitor cells such as, without limitation, transcription factors Mesp1, Nkx2.5, GATA4, Mef2C, Irx4, TBX5, TBX20, Isl1, SRF as well cell surface markers CXCR4, PDGFRα, c-Kit, Flk-1, and Sca-1. iCPCs can be obtained by reprogramming various differentiated (i.e., non-pluripotent and multipotent) somatic cells. Apart from genetic material introduced to encode the factors, the reprogrammed (i.e., converted) cells are substantially genetically identical to the somatic cells from which they were derived. Preferably, the differentiated somatic cell is a mammalian somatic cell. More preferably, a mammalian somatic cell is from a human or a rodent.

As used herein, the term "reprogramming" refers to a genetic process whereby differentiated somatic cells are converted into multipotent cells having a greater multipotency potential than the cells from which they were derived. Likewise, the term "reprogramming factor" refers to a factor, such as a gene or other nucleic acid, or a functional fragment thereof, as well as an encoded factor or functional fragment thereof, which have the capacity to reprogram, transform, or enhance the potency of a somatic cell, so that it becomes a proliferative and expandable multipotent progenitor cell. In exemplary embodiments, a method as described herein results in direct lineage reprogramming which, as used herein, means that an iCPC is obtained from a differentiated somatic cell without the somatic cells into which reprogramming factors are introduced passing through a pluripotent cell stage.

In some cases, the reprogramming factors are early cardiac transcription factors. The factors can include, without limitation, Mesp1, Baf60c, Nkx2.5, Gata4, and Tbx5. In some cases, factors are introduced as a set of factors comprising a plurality of early cardiac transcription factors (TFs). The plurality can comprise some of all of Mesp1, Baf60c, Nkx2.5, Gata4, and Tbx5. In some cases, the plurality of early cardiac transcription factors includes some or all of Mesp1, Mesp2, Gata4, Gata6, Baf60c, SRF, Isl1, Nkx2.5, Irx4, Tbx5, and Tbx20. In other cases, the plurality includes some or all of T, Mesp1, Mesp2, Tbx5, Tbx20, Isl1, Gata4, Gata6, Irx4, Nkx2.5, Hand1, Hand2, Tbx20, Tbx18, Tip60, Baf60c, SRF, and Hey2. In some cases, the set of factors further comprises at least one chromatin remodeling factor. In some embodiments, as few as five factors are sufficient. For example, a set of factors can comprise Mesp1, Baf60c, Nkx2.5, Gata4, and Tbx5.

In some cases, the plurality of factors comprises one or more artificial transcription factors (ATFs). ATFs resemble naturally occurring transcription factors and generally comprise a DNA-binding domain that can recognize a specific DNA sequence (typically near the transcription start site of a targeted gene) and an effector domain that mediates transcriptional activation or repression. In some cases, the effector domain is an activator of transcription such as, for example, herpes simplex virus VP16, VP64, or nuclear factor-κB subunit p65.

Reprogramming factors optionally can be present only transiently in the reprogrammed cells or can be maintained in a transcriptionally active or inactive state in the genome of the reprogrammed cells. Likewise, the reprogramming factors can be present in more than one copy in the induced cardiac progenitor cells, where the factor can be integrated in the cell's genome, can be extra-chromosomal, or both. Preferably, the factors are encoded by nucleic acid obtained from a human animal or a non-human animal.

Suitable somatic cells can be any somatic cell such as a non-embryonic cell obtained from a fetal, newborn, juvenile or adult mammal, including a human. Differentiated somatic cells, including cells from a fetal, newborn, juvenile or adult mammal, including human, individual, are suitable starting cells in the methods. Suitable somatic cells include, but are not limited to, bone marrow cells, epithelial cells, endothelial cells, fibroblast cells, hematopoietic cells, keratinocytes, hepatic cells, intestinal cells, mesenchymal cells, myeloid precursor cells and spleen cells. Suitable somatic cells are receptive, or can be made receptive using methods generally known in the scientific literature, to uptake of reprogramming factors including genetic material encoding the factors. Uptake-enhancing methods can vary depending on the cell type and expression system. Exemplary conditions used to prepare receptive somatic cells having suitable transduction efficiency are well-known by those of ordinary skill in the art. The starting somatic cells can have a doubling time of about twenty-four hours.

A method for producing a proliferative and expandable cardiac progenitor cell as described herein includes a introducing step in which a set of factors are introduced into somatic cells by transfection or other known methods for introduction of genetic material into mammalian somatic cells. In some cases, a set of factors is introduced into a mammalian somatic cell as a vector or construct encoding the set of factors. As used herein, the terms "construct" and "vector" refer to a recombinant nucleotide sequence, generally a recombinant DNA molecule, that has been generated for the purpose of the expression of a specific nucleotide sequence(s), or is used in the construction of other recombinant nucleotide sequences. In general, the terms "vector" and "construct" are used herein to refer to a recombinant DNA molecule or, in some cases, a nucleic acid/polymer complex or nucleic acid/peptide complex. The terms "plasmid" and "vector" as used herein include autonomously replicating nucleotide sequences as well as genome integrating nucleotide sequences.

In exemplary embodiments, a set of factors is introduced using a vector, where the vector includes an expression construct comprising a promoter operably linked to a nucleotide sequence encoding inducing factor under the transcriptional control of the regulatable promoter. As used herein, the term "operably linked" refers to a DNA sequence and a regulatory sequence(s) are connected in such a way as to permit gene expression when the appropriate molecules (e.g., transcriptional activator proteins) are bound to the regulatory sequence(s). In preferred cases, the operably linked promoter is not natively associated with the coding sequence of a reprogramming factor. In some cases, introducing comprises direct exposure of a somatic cell to the factors per se, whereby an interaction between the cells and the factors is sufficient to achieve reprogramming of the somatic cell to iCPC. Exposure to every member of the set of factors may not be essential to achieving reprogramming to iCPC.

Vectors suitable for use according to the methods described herein include, without limitation, non-viral vectors such as non-viral episomal vectors. As used herein, the terms "non-viral vector" and "non-viral construct" are used interchangably and mean that the vector or construct cannot encode an infectious virus. Episomal vectors include structural components that permit the vector to self-replicate in the somatic starting cells. For example, the known Epstein Barr oriP/Nuclear Antigen-1 (EBNA-I) combination (see, e.g., Linder et al., *Plasmid* 58:1 (2007), incorporated by reference as if set forth herein in its entirety) is sufficient to support vector self-replication and other combinations known to function in mammalian, particularly primate, cells can also be employed. Preferably, vectors suitable for use according to the methods described herein can be propagated and expressed episomally in human cells. Standard techniques for the construction of non-viral vectors suitable for use in the present invention are well-known to one of ordinary skill in the art and can be found in publications such as Sambrook J, et al., "Molecular cloning: a laboratory manual," (3rd ed. Cold Spring harbor Press, Cold Spring Harbor, N. Y. 2001), incorporated herein by reference as if set forth in its entirety. In exemplary embodiments, suitable expression cassettes structures are created using conventional methods by direct polymerase chain reaction (PCR) amplification of open reading frames (ORFs) from some or all of a set of reprogramming factors. Other non-viral vectors suitable for use according to the methods provided herein include, without limitation, In other embodiments, the vectors are non-viral vectors such as non-viral episomal vectors, cationic liposomes, neutral liposomes, polymer-nucleic acid complexes (e.g., polymer nanoparticles, dendrimers), and peptide-nucleic acid complexes.

In some cases, vectors useful for the methods provided herein include viral vectors, most commonly adenoviral and retroviral vectors. Exemplary viral-based vectors include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200, 651; EP 0 345 242; and WO 91/02805); alphavirus-based vectors (e.g., Sindbis virus vectors, Semliki forest virus (ATCC VR-67; ATCC VR-1247); and adeno-associated virus (AAV) vectors (see, e.g., WO 94/12649, WO 93/03769; WO 93/19191; WO 94/28938; WO 95/11984 and WO 95/00655).

Suitable reprogramming vectors are episomal vectors, such as plasmids, that do not encode all or part of a viral genome sufficient to give rise to an infectious or replication-competent virus, although the vectors can contain structural elements obtained from one or more virus.

One or a plurality of reprogramming vectors can be introduced into a single somatic cell. One or more transgenes can be provided on a single reprogramming vector. One strong, constitutive transcriptional promoter can provide transcriptional control for a plurality of transgenes, which can be provided as an expression cassette. Separate expression cassettes on a vector can be under the transcriptional control of separate strong, constitutive promoters, which can be copies of the same promoter or can be distinct promoters. Various heterologous promoters are known in the art and can be used depending on factors such as the desired expression level of the potency-determining factor. It can be advantageous to control transcription of separate expression cassettes using distinct promoters having distinct strengths in the target somatic cells. In human somatic cells, both the human EF 1α elongation factor promoter (EF 1α) and CMV are strong promoters, but the cytomegalovirus (CMV) immediate early promoter is silenced more efficiently than the EF1α promoter such that expression of transgenes under control of the former is turned off sooner than that of transgenes under control of the latter. Preferably, where a plurality of transgenes is encoded on a single transcript, an internal ribosome entry site is provided upstream of transgene(s) distal from the transcriptional promoter. Although the relative ratio of factors can vary depending upon the factors delivered, one of ordinary skill in possession of this disclosure can determine an optimal ratio of factors.

The skilled artisan will appreciate that the advantageous efficiency of introducing all factors via a single vector rather than via a plurality of vectors, but that as total vector size increases, it becomes increasingly difficult to introduce the vector. The skilled artisan will also appreciate that position of a factor on a vector can affect its temporal expression, and the resulting reprogramming efficiency. After introduction of the reprogramming vectors, and while the somatic cells are being reprogrammed, the vectors can persist in target cells while the introduced transgenes are transcribed and translated. Transgene expression can be advantageously down-regulated or turned off in cells that have been reprogrammed to a pluripotent state. The reprogramming vector(s) can remain extra-chromosomal.

In an exemplary embodiment, an expression construct or vector suitable for use according to the methods provided herein comprise at least one regulatory sequence or control sequence. As used herein, a "regulatory sequence" or "control sequence" is a nucleotide sequence involved in an interaction of molecules that contributes to the functional regulation of a polynucleotide, such as replication, duplication, transcription, splicing, polyadenylation, translation, or degradation of the polynucleotide. Transcriptional control elements include promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. In some cases, an expression vector comprises a regulatable (e.g., inducible) promoter. Control of expression of reprogramming factors can be achieved by contacting a somatic cell having at least one reprogramming factor under the control of an inducible promoter with a regulatory agent or other inducing agent. In such cases, a set of factors is introduced to a somatic cell using an expression construct comprising a regulatable promoter operably linked to at least one polynucleotide sequence encoding one or more reprogramming factors. Inducible gene expression is obtained by virtue of the presence or absence of an inducer. Several inducible promoter systems have been described including those controlled by hormones (e.g., estrogen), RU-486 (a progesterone antagonist) (Wang et al. 1994 Proc. Natl. Acad. Sci. USA 91:8180-8184), steroids (Mader and White, 1993 Proc. Natl. Acad. Sci. USA 90:5603-5607), and tetracycline (Gossen and Bujard 1992 Proc. Natl. Acad. Sci. USA 89:5547-5551; U.S. Pat. No. 5,464,758). In exemplary embodiments, expression of the set of factors is induced in the presence or absence of a tetracycline or doxycycline (dox) inducing agent. Dox is a derivative of the antibiotic tetracycline. When a tetracyline-controlled inducible system is used, transcription is reversibly turned on or off in the presence of tetracycline or dox. A "Tet-Off" inducible system activates expression in the absence of tetracycline and its derivatives (e.g., Dox), whereas a "Tet-On" system activates in the presence of tetracycline and its derivatives. In exemplary embodiments, a method provided herein comprises contacting a somatic cell to an iCPC induction medium that comprises an inducing agent.

In exemplary embodiments, the methods provided herein further comprise a step in which iCPCs produced according to a method provided herein are maintained in a proliferative state. In some cases, an iCPC maintenance medium comprises an iCPC induction medium lacking an inducing agent (e.g., dox). In other cases, iCPCs produced according to a method provided herein are maintained in a proliferative state by culturing the cells in a medium that comprises an activator of canonical Wnt signaling and, optionally, an activator of Jak/Stat signaling, each in an amount sufficient to maintain proliferating iCPC. For example, a culture medium for maintaining proliferative iCPCs comprises an activator of canonical Wnt signaling and an activator of Jak/Stat signaling. Appropriate activators of canonical Wnt signaling include, without limitation, 6-bromoindirubin-3'-oxime (BIO), CHIR 99021, CHIR 98014, and BIO-acetoxime, LiCl, SB 216763, SB415286, AR A014418, 1-Azakenpaullone, and Bis-7-indolylmaleimide. Activators of Jak/Stat signaling useful for the methods described herein include Interleukin (IL)-6-related cytokines such as Leukemia Inhibitory Factor (LIF), IL-2, IL-6, IL-11, leptin, and ciliary neurotrophic factor (CNTF). In some cases, a culture medium for maintaining proliferative iCPCs comprises BIO as the activator of canonical Wnt signaling and LIF as the activator of Jak/Stat signaling. In exemplary embodiments, maintained iCPCs are separated from non-reprogrammed cells by cell sorting, splitting, manual dissection, or a combination thereof.

A somatic cell can have a heterologous sequence for inducing expression of nucleic acids encoding the set of factors, whereby the step of expressing a set of factors comprises inducing gene expression by virtue of the presence or absence of an inducer.

In some cases, a somatic cell alternatively or additionally comprises a heterologous sequence encoding a non-lethal marker that is expressed only in cells at a developmental stage characteristic of a cardiac progenitor cell. Non-lethal markers include, without limitation, fluorescent markers such as Green Fluorescent Protein (GFP), Enhanced Green Fluorescent Protein (EGFP), and luciferase. A selectable marker gene can be used to identify the reprogrammed cells expressing the marker through visible cell selection techniques, such as fluorescent cell sorting techniques. In such cases, the expressing step comprises inducing the expression such that the cell is reprogrammed to produce the iCPC, such that the non-lethal, selectable marker indicates the presence of a cell at the developmental stage characteristic of cardiac progenitor cells. It is not intended that all cells in the reprogrammed cell culture have the desired level of potency. Given the inefficiencies of cell sorting technology, the variations in levels of gene expression and other biological effects, some cells in the enriched population may not be multipotent induced cardiac progenitor cells. However, at a practical level, the reprogrammed cell population derived from somatic cells is enriched for induced cardiac progenitor cells having multipotency to differentiate into cardiomyocytes, smooth muscle cells, and endothelial cells.

Induced CPCs can be identified using any appropriate method such as, for example, detecting nuclear localization of cardiac progenitor cell transcription factors (TFs) (e.g., Irx4, Gata4, Nkx2.5) or detecting expression of CPC-associated cell surface markers (e.g., Cxcr4, Flk1, Pdgfr-α, cKit). Importantly, iCPCs also can be identified under these culture conditions based on morphology and in the absence of a detectable reporter (i.e., for use in vivo).

It can be advantageous to separate iCPCs from non-reprogrammed cells. Any appropriate cell separating or cell sorting method can be used according to a method provided herein. Procedures for separation of iCPCs can include magnetic separation, using antibody coated magnetic beads, affinity chromatography, and "panning" with antibody attached to a solid matrix, e.g., plate, or other convenient technique. Techniques providing accurate separation include fluorescence activated cell sorting, which can have varying degrees of sophistication, e.g., a plurality of color channels, low angle and obtuse light scattering detecting channels, impedance channels, etc. Cells can be sorted on the basis of a cell surface marker characteristic of cardiac progenitor cells or other cell type. Other methods for separating cells based on the distinguishable attribute(s) of the target cell include separating non-proliferative reprogrammed cells by splitting the cultures such that non-reprogrammed cells, which do not proliferate, are outcompeted by the proliferative, reprogrammed cells. Alternatively, reprogrammed cells can be manually or mechanically dissected from non-reprogrammed cells on the basis of fluorescence or other morphological differences.

Induced cardiac progenitor cells obtained according to a method provided herein can be cultured in any medium used to support growth of cardiac progenitor cells. For example, a culture medium can include DMEM, 10% FBS 1% NEAA, 1% L-glutamine, and 1% Pen/strep. Other appropriate culture media include, without limitation, a defined medium, such as TeSR™ (StemCell Technologies, Inc.; Vancouver, Canada), mTeSR™ (StemCell Technologies, Inc.) and StemLine® serum-free medium (Sigma; St. Louis, Mo.), as well as conditioned medium. As used herein, a "defined medium" refers to a biochemically defined formulation comprised solely of biochemically-defined constituents. A defined medium may also include solely constituents having known chemical compositions. A defined medium may further include constituents derived from known sources. As used herein, "conditioned medium" refers to a growth medium that is further supplemented with soluble factors from cells cultured in the medium.

Induced cardiac progenitor cells obtained according to the methods described herein are advantageous for a variety of biomedical and clinical applications including, without limitation, basic biomedical research (e.g., cardiac development, cardiac cell biology and physiology), modeling cardiac diseases, drug discovery and toxicology, and cardiac regenerative therapies. With respect to regenerative therapies, induced cardiac progenitors as described herein are less tumorigenic than pluripotent stem cell derivatives, provide a scalable cell source, and differentiation can be directed to obtain cardiomyocytes, smooth muscle cells, and endothelial cells.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

EXAMPLES

Example 1—Defined Factor Libraries

Figure 2:
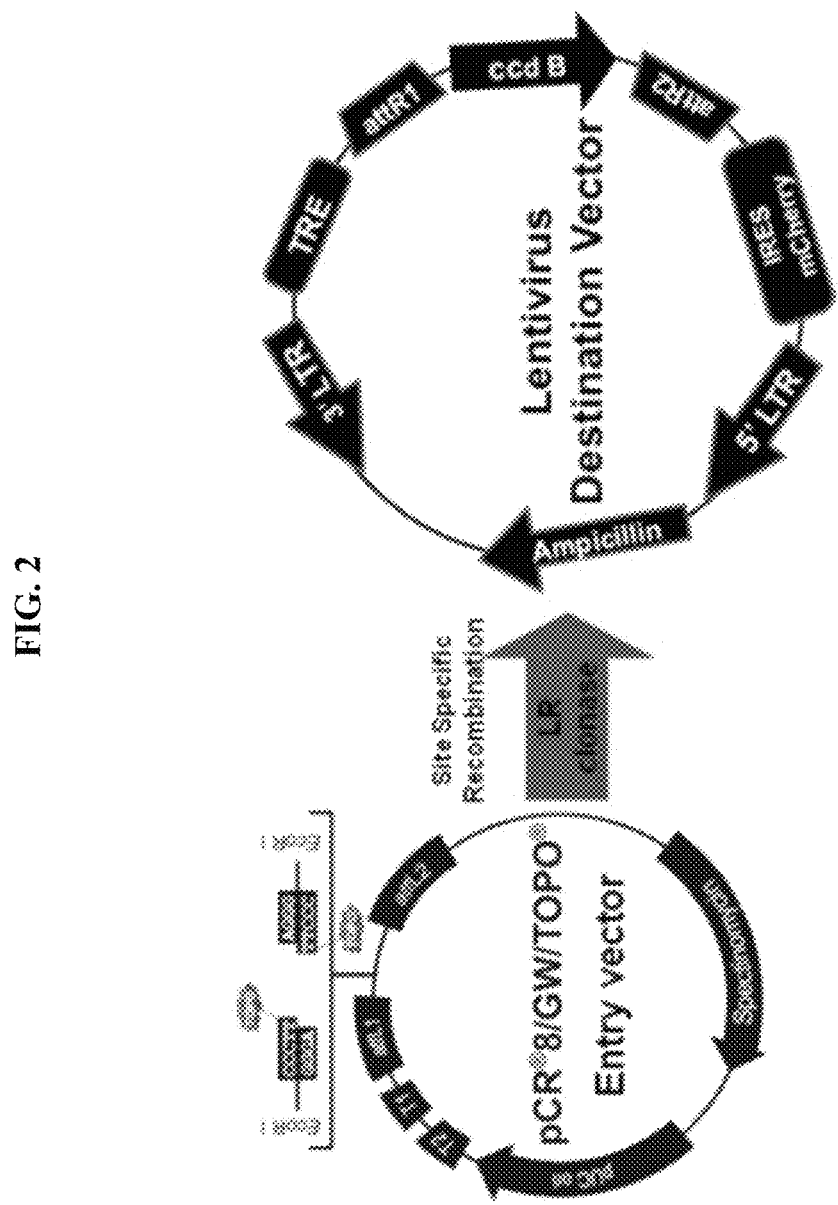
FIG. 2 depicts the vectors used in creation of a lentiviral expression library that includes various agents and factors associated with cardiogenesis.

A nucleic acid Gateway entry library encoding transcription factors and chromatin remodeling agents involved in normal cardiogenesis as well as factors involved in reprogramming of somatic cells to pluripotency was generated by individually cloning the nucleic acid coding sequence of each gene into Gateway entry vector pCR™8/GW/TOPO® (Invitrogen) to produce a Gateway entry library. A minimal Kozak sequence (ACC) was added upstream of ATG whenever possible. The Gateway entry library was then transferred into a doxycycline-inducible, Gateway-adapted lentivirus destination vector (pSAM, see, U.S. Patent Publication Number 2007/0243608, incorporated herein by reference as if set forth in its entirety) using site specific recombination mediated by LR Clonase II™ (Invitrogen) to create a lentivirus destination vector (FIG. 2) that was sequence verified.

In various iterations, subsets of such lentivirus destination vectors separately encoding various combinatorial sets of factors were combined and were included in the various lentivirus expression libraries thus produced. The sets of factors represented in the libraries were as follows:

Factor Combinations
Set of 22 Factors: T, Mesp1, Mesp2, Tbx5, Tbx20, Isl1, Gata4, Gata6, Irx4, Nkx2.5, Hand1, Hand2, Tbx20, Tbx18, Tip60, Baf60c, SRF, Hey2, Oct4, Klf4, Sox2, L-myc.
Set of 18 Factors: T, Mesp1, Mesp2, Tbx5, Tbx20, Isl1, Gata4, Gata6, Irx4, Nkx2.5, Hand1, Hand2, Tbx20, Tbx18, Tip60, Baf60c, SRF, Hey2.

Set of 11 Factors: Mesp1, Mesp2, Gata4, Gata6, Baf60c, SRF, Isl1, Nkx2.5, Irx4, Tbx5, Tbx20.

Set of 6 Factors: Mesp1, Baf60c, Nkx2.5, Gata4, Tbx5, Oct4. (In addition to being an iPSC reprogramming factor, Oct4 has a role in development of CPC as well, so it was included in this set)

Set of 5 Factors: Mesp1, Baf60c, Nkx2.5, Gata4, Tbx5

Instead of preparing a lentivirus destination vector for use in preparation of the factor-encoding libraries, genes cloned into the pCR™8/GW/TOPO® Gateway entry vector were alternatively transferred using site specific recombination mediated by LR Clonase II (Invitrogen) into a piggyBAC destination vector.

The factors represented in the libraries (and their source organism) are shown in Table 1. Full-length coding sequences for each factor are provided in the Sequence Listing. Nucleic acids encoding Tbx5 (SEQ ID NO:6), Gata4 (SEQ ID NO:8), T (SEQ ID NO:3), Gata6 (SEQ ID NO:9), Mesp2 (SEQ ID NO:5), Nkx2.5 (SEQ ID NO:2), Isl1 (SEQ ID NO:7), Tbx20 (SEQ ID NO:11), Hand1 (SEQ ID NO:12), Hand2 (SEQ ID NO:13), Hey2 (SEQ ID NO:16), Tbx18 (SEQ ID NO:1), Tip60 (SEQ ID NO:18), Oct4 (SEQ ID NO:19), Klf4 (SEQ ID NO:20), L-myc (SEQ ID NO:21), Sox2 (SEQ ID NO:22) were obtained from a mouse embryoid body cDNA library. Human Baf60c DNA (SEQ ID NO:15) was obtained from Addgene Plasmid #21036. Human Mesp1 DNA (SEQ ID NO:4) was obtained in a vector from Michael Kyba at University of Minnesota. Human Mef2c (SEQ ID NO:14) and SRF DNA (SEQ ID NO:17) was obtained in vectors from Youngsook Lee at University of Wisconsin-Madison. Human Irx4 (SEQ ID NO:10) was obtained in a vector from Dr Gary Lyons at University of Wisconsin-Madison.

Production of Lentivirus Particles

The lentiviral expression library vectors were transfected into HEK 293 TN cells (SBI). Briefly, one day before transfection, $4.5 \times 10^6$ cells were plated in a 10 cm dish. Transfections included 7 μg of lentiviral library vectors, 10 μg psPAX2 (Addgene plasmid #12260—packaging), 5 μg pMD2.G (Addgene plasmid #12259—envelope) and Lipofectamine 2000 (Invitrogen) (1:2 ratio). The transfected cells were incubated for 15-16 hours in transfection medium (Lipofectamine-DNA complexes in 2 ml OPTI-MEM medium and 3 ml fibroblast medium (DMEM, 10% FBS, 1% NEAA, 1% L-glutamine and 1% Pen/strep)), which was then replaced with 5 ml of fibroblast medium. After 48-52 hours in fibroblast medium, supernatant containing lentivirus particles was collected, filtered (Millipore 0.45 μM) and frozen at −80° C.

Isolation of Primary Fibroblasts

Adult cardiac- and lung fibroblasts were separately obtained for use in subsequent studies from 1-3 month-old Nkx2.5-EYFP/rtTA double transgenic mice by explant culture. Heart and lung explants were washed with PBS to remove blood cells and were then minced in fibroblast medium (DMEM, 10% FBS, 1% NEAA/L-glutamine/Pen/ strep) to about 1 mm³. The minced explants were trypsinized (0.25% trypsin-EDTA) for 10 minutes and were then plated on 0.1% gelatin-coated dishes in fibroblast medium for 10-12 days. Primary fibroblasts that migrated from the explants were harvested, filtered through a 40 μM cell strainers (BD), passaged 1-2 times, and, when not used for experiments right away, frozen in freeze medium (DMEM, 20% FBS, 20% DMSO). No contaminating cTnT⁺ cardiomyocytes were present in the explant culture and the isolated fibroblasts did not express eYFP.

The fibroblasts thus obtained are particularly useful in that doxycycline induces expression of nucleic acid that encodes factors and agents introduced using the lentiviral vectors. Moreover, yellow fluorescent protein (YFP) reporter is expressed only in cells generated in the methods that correspond to cells present in a developing mouse heart at between E7.75-E10.5 during embryogenesis. The developmentally restricted Nkx2.5-EYFP reporter identifies early CPCs, but it is inactive during later stages of cardiac development (E11 onwards) and in the adult heart. The Nkx2.5-eYFP/rtTA mice were obtained by mating male Nkx2.5-eYFP transgenic mice (provided by Dr. Daniel Garry, University of Minnesota and described in Masino et al., *Circulation Research* 95(4):389-397 (2004), incorporated herein by reference as if set forth in its entirety) with female B6.Cg-Gt(ROSA)26Sortm1(rtTA*M2)Jae/J mice (Jackson Labs) that are homozygous for reverse tetracycline-controlled transactivator rtTA. The male parent Nkx2.5-eYFP mice contain a transgenic 6.6 kb enhancer fragment upstream of Nkx 2.5.

Lentiviral Infection of Primary Fibroblasts and Differentiation to iCPC

One or two days before infection, the primary fibroblasts were seeded in a gelatinized 12 well plate at density of 50,000 cells/well. Immediately before infection, lentivirus supernatants obtained after transfection with vectors of a lentivirus expression library were thawed in 37° C. water bath. The seeded cells were then fed with lentivirus infection media (lentivirus-vector-containing supernatant supplemented with 8 μg/ml Polybrene (Sigma)) to infect the fibroblasts. Lentivirus infection was continued for 48 hours, after which the medium was changed to iCPC induction medium (DMEM, 10% FBS, 1% NEAA, 1% L-glutamine, 1% Pen/strep, 4 μg/ml doxycycline (Sigma), 2.5 μM BIO (Cayman Chemical), $10^3$ units/ml LIF (Millipore), until cells were reprogrammed by direct lineage reprogramming (i.e., without passing through a pluripotent cell stage). Reprogrammed cells might not take up copies of, or express, every factor in each set and different subsets of factors in a set might independently support reprogramming.

After reprogramming was achieved, and after one passage in iCPC induction medium, iCPC were maintained in iCPC maintenance medium (iCPC induction medium without doxycycline). iCPC were differentiated into cardiac lineage cells, by aggregating the iCPC in 24-well, low attachment plates (Corning) for 2-6 days in cardiac differentiation medium (fibroblast medium, 5 μM IWP4 (Stemgent), 50 ng/ml BMP4 (RD Systems), 10 ng/ml VEGF (RD Systems), 30 ng/ml bFGF (RD Systems) and then plating the aggregates in cardiac differentiation medium. After 2-3 more days, the aggregates where then plated on gelatin-coated dishes and cultured in fibroblast medium containing 1% serum for 10-50 days.

Immunocytochemistry for Detecting Cardiac-Related Markers

Cells were fixed in methanol free formaldehyde (4%) for 12 minutes at room temperature and then permeabilized with 0.1% Triton X for 6 minutes at room temperature and blocked in 2% serum (Goat or Donkey), 5% BSA in PBS for 1 hour at room temperature. Primary antibodies were incubated in blocking buffer containing 0.1% Triton X at 4° C. overnight. Secondary antibodies were incubated in blocking buffer containing 0.1% Triton X for 2 hours at room temperature.

Primary antibodies used and their respective dilutions were—cTnT (Thermo Scientific—1:200), MF20 (Iowa hybridoma bank—1:10), Alpha actinin (Sigma—1:250), Cardiac actin (Sigma—1:400), CD31 (BD Pharmingen—1:400), Smooth Muscle-Myosin Heavy Chain (SM-MHC, Biomedical Technologies—1:250), Nkx2.5 (RD Systems—1:100), Isl1 (RD Systems—1:100), Gata4 (Santa Cruz—1:200), Irx4 (Abgent—undiluted supernatant).

Quantitative RT-PCR

Total RNA was isolated from cells using RNAqueous® Kit (Invitrogen). Reverse transcription was performed using iScript™ Reverse Transcription Supermix (Bio-Rad). qRT-PCR was performed using CFX96™ Real Time PCR Detection System (Bio-Rad) using SsoFast™ EvaGreen Supermix (Bio-Rad). MIQE guidelines were followed in designing qPCR experiments. mRNA levels were normalized by comparison to β-actin (Δ CT) and data are presented as fold change with respect to expression in control fibroblasts (ΔΔ CT).

RNA-Seq and Bioinformatics Analysis

RNA was extracted as above from AC Fibs derived iCPCs either at low passage (1-3) or high passage (8-10). Uninfected AC Fibs were used as control. RNAseq was performed using HiSeq 2500 (Illumina) in duplicates from independent biological samples. Sequencer outputs were processed using CASAVA-1.8.2 (Illumina), and each sample's reads were processed using RSEM version 1.2.3 to obtain expression measures for genes. The percentage of reads that mapped to the RefSeq mm09 reference transcriptome ranged from 79% to 86%. Differential analysis was done using EBSeq version 1.5.3. The EBSeq input dataset contained un-normalized expected count values for all genes as output from RSEM for each sample paired with another (sequence-independent) with condition strings as represented in Table 1 below along with the size factors calculated by median normalization (MedianNorm function within the EBSeq package). Additional input parameters to EBSeq (specifically the EBTest function) specified five total iterations were to be run (maxround=5), genes with similar means were to be grouped into 1000 bins (NumBin=1000), no pooling was to be used (Pool=F), transcript variances with mean less than a variance cutoff of 10-10 (ApproxVal=10^-10) were approximated as the mean divided by (1-10-10), all model parameters (Alpha, Beta, PInput, RInput) were null so that all probabilities were estimated from the data, initial candidate genes for differential expression were taken from the 25%-75% quantile (PoolLower=0.25, PoolUpper=0.75), and transcripts with all zero were to be removed from the dataset (Qtrm=0.99, QtrmCut=0). The targeted false discovery rate for each run was 0.05. Transcripts per million values were used for all calculations. STRING database was used for GO analysis (Franceschini et al., 2013). The targeted false discovery rate (FDR) used for each run of EBSeq was 0.05. Transcripts per million (TPM) values were used for calculations throughout this study.

TABLE 1

EBSeq Input Dataset

| EBSeq Run | Samples | Condition String (Same Order as in 'Samples') | Size Factors (Same Order) |
|---|---|---|---|
| 1 | 1 and 4 | "Control, Psg1" | 1, 1 |
| 2 | 4 and 6 | "Psg1, Psg5" | 0.973, 1.028 |
| 3 | 1 and 6 | "Control, Psg5" | 0.960, 1.042 |

$Ca^{2+}$ Imaging

Cells were loaded with Rhod-2, AM (Invitrogen) for 20 mins at 37° C. in fibroblast medium, then washed and incubated for additional 30 mins at 37° C. to allow for deesterification of the dye. Rhod-2 loaded cells were analyzed by Nikon epifluorescence microscope with NIS elements software.

Embryo Injections, Immunostaining, and Imaging

Cardiac crescent stage mouse embryos were obtained by timed matings. iCPCs were infected with a GFP lentivirus (Addgene #17448) to trace cells in vivo. Approximately 200-500 iCPCs were introduced into the cardiac crescent of dissected mouse embryos in dissection medium via a mouth-held glass capillary (~20 μm opening). Operated and stage-matched unoperated embryo samples were then placed into whole embryo culture medium (Downs, *Methods in Molecular Medicine* 121:241-272 (2006)), and cultured for 24 or 48 hours, with a change to fresh gas- and temperature-equilibrated culture medium at the end of 24 hours for those embryos continuing on for 48 hours. At the end of the culture period, embryos were scored for a variety of parameters, including heartbeat, yolk sac circulation, morphology, and imaged using a Nikon epifluorescence microscope to determine the location of injected GFP+ cells. Embryos were then fixed with 4% PFA. Immunofluorescence of whole mount embryos was done as previously described by (Nelson et al., *Developmental Dynamics* 243:381-92 (2014)) and imaging was performed using a custom built multi-photon microscope. Imaris software (Bitplane) was used to make 3D reconstructions.

Statistical Analysis

Differences between groups were tested for statistical significance using ANOVA or for comparison of two groups, Student's t-test. p values of <0.05 were regarded as significant.

Results

Generating and Testing Defined Factor Libraries

A first defined factor library prepared as described above encoded 22 factors (T, Mesp1, Mesp2, Tbx5, Tbx20, Isl1, Gata4, Gata6, Irx4, Nkx2.5, Hand1, Hand2, Tbx20, Tbx18, Tip60, Baf60c, SRF, Hey2, Oct4, Klf4, Sox2, L-myc), including early cardiac transcription factors (expressed during late primitive streak to cardiac crescent stage), late cardiac transcription factors (expressed during heart tube to chamber formation stage), cardiac chromatin remodeling agents, and reprogramming factors employed in reprogramming somatic cells to induced pluripotent cells (iPSC).

Screening for Cardiac Progenitor Cell Inducing Factors

At the outset, the operability, transcription/translation efficiency, and doxycycline regulation of the lentivirus expression system after delivery into fibroblasts was tested and confirmed. Fibroblast cells were infected with a lentiviral vector containing the Green Fluorescent Protein (GFP) gene. In the absence of induction with doxycycline, no GFP expression (evidenced by fluorescence) was observed. In contrast, 24 hours after exposure to doxycycline, 90-95% of cells showed bright GFP fluorescence. One week after doxycycline was withdrawn, no GFP expression was observed. After infection of fibroblasts with individual factors provided in lentiviral vectors, efficient transcription was confirmed by RT-PCR and translation was confirmed by immunocytochemistry.

Figure 3:
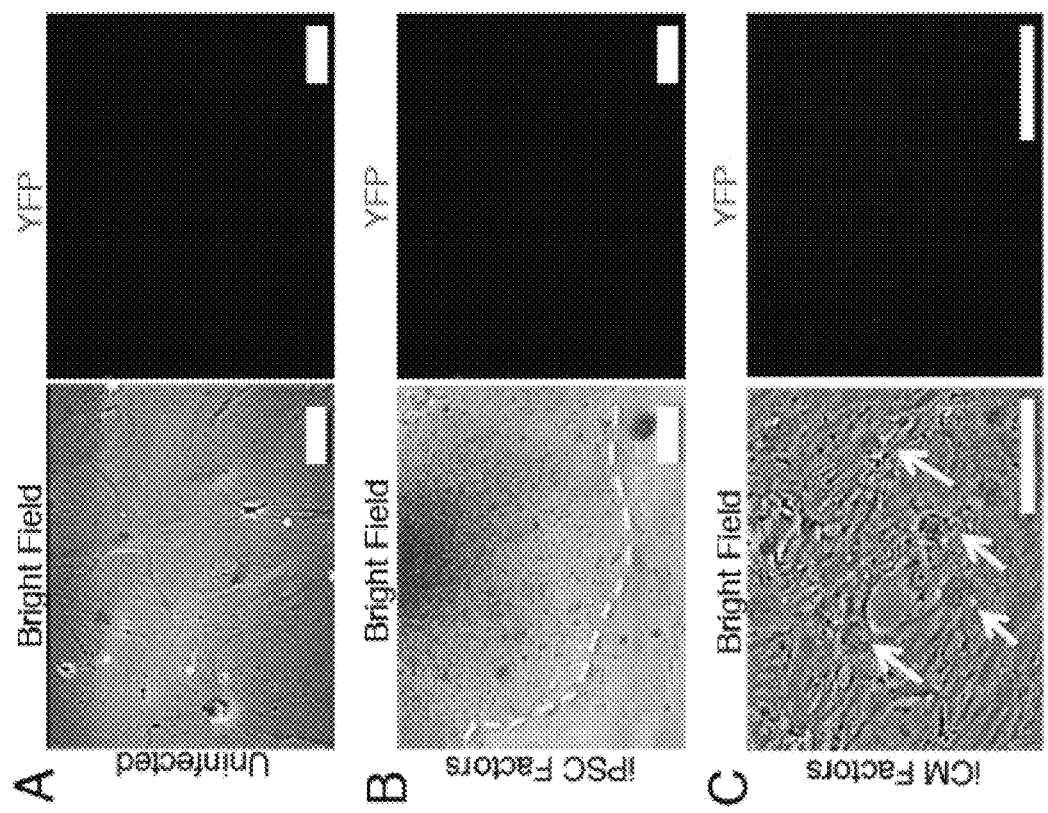
FIG. 3 depicts a screen for iCPC inducing factors and culture conditions. (A) Uninfected AC Fibs showed no EYFP expression. (B) AC Fibs infected with iPS factors (Klf4, Oct4, L-myc, Sox2) showed proliferative cells that formed iPS-like colonies which were EYFP− (3 weeks after adding dox). (C) Neonatal cardiac fibroblasts infected with Gata4, Mef2c, Tbx5 (iCM factors) showed spontaneous beating 25 days after dox treatment. Arrows indicate induced cardiomyocytes (iCMs). iCMs did not show EYFP expression. (D) AC Fibs infected with combinations of either 22 factors or 18 factors developed into EYFP+ cells 3 weeks after dox induction. (E) AC Fibs infected with an eleven-factor set and induced by exposure to dox develop proliferative EYFP+ colonies; however, upon expansion in dox only culture condition these cells lost EYFP expression and senesced within 3-5 passages. (F) Addition of BIO resulted in expandable EYFP+ cells. However, they became spindle-shaped and were not highly proliferative. (G) Addition of both LIF and BIO produced the brightest EYFP+ cells which were robustly expandable. Scale bar represents 100 μm in A-D and 200 μm in E-G.

Uninfected adult cardiac fibroblasts (AC Fibs) did not express Enhanced Yellow Fluorescent Protein (EYFP) and senesced after 3-4 passages (FIG. 3A). As a first test of the dox-inducible library for reprogramming, AC Fibs were infected with iPSC factors. Following these infections, dox treatment produced proliferative cells that formed EYFP-iPSC colonies (FIG. 3B).

Uninfected adult cardiac fibroblasts (AC Fibs) were then infected with iCM factors Gata4 (G), Mesp1 (M), and Tbx5 (T). Even after extended dox induction (6 weeks), we did not observe contracting cells or EYFP+ cells. However, neonatal cardiac fibroblasts infected with iCM factors reprogrammed into spontaneously contracting EYFP- iCMs after 4 weeks of dox treatment (FIG. 3C). These results demonstrate dox-inducible reprogramming with the described vector system. Furthermore, the Nkx2.5-EYFP reporter is not activated during iPSC or iCM reprogramming.

Next, AC Fibs were infected with a library of lentiviruses containing all 22 factors, or GFP only, or iPSC factors only (negative control) and were then induced with doxycycline. After induction via dox treatment, cultures were monitored for appearance of EYFP$^+$ cells. Infection of AC Fibs with a mixture of lentiviruses containing all 22 factors resulted in a small number of EYFP$^+$ proliferative colonies only after dox treatment (FIG. 3D).

When iPSC factors were subtracted from the 22-factor expression library (leaving 18 cardiac factors), proliferative EYFP+ cells were observed three weeks after dox treatment (FIG. 3D). Reasoning that factors expressed early in cardiac development might have the highest potential to reprogram fibroblasts into iCPCs, 11 early cardiac factors (Mesp1, Mesp2, Gata4, Gata6, Baf60c, SRF, Isl1, Nkx2.5, Irx4, Tbx5, Tbx20) were selected for AC Fibs infection. Infection with the 11-factor expression library gave rise to proliferative EYFP$^+$ cells (FIG. 1B).

The time course of appearance of EYFP$^+$ cells upon infection with 11 factors was analyzed. Single EYFP$^+$ cells were detected as early as day 4 after dox treatment. By 3 weeks after dox treatment, these EYFP$^+$ cells developed into two-dimensional, highly proliferative colonies of EYFP$^+$ cells that lost their parental fibroblast morphology and exhibited a high nuclear-cytoplasmic ratio (FIGS. 1C-D). Infection with 11 factors reproducibly gave rise to EYFP$^+$ proliferative colonies (4 colonies/50,000 cells; efficiency 0.008%) (FIGS. 1E-F). We manually isolated these EYFP$^+$ colonies and tried to expand them by splitting. However, cells lost EYFP expression and senesced after 3-5 passages in the 'dox only' culture condition (FIG. 1G).

Wnt and JAK/STAT Signaling Promotes Proliferative Reprogrammed Cells

The overexpression of cardiac factors alone, even though sufficient to produce EYFP+ colonies, was insufficient for maintaining EYFP+ cells in a proliferative, reprogrammed state, suggest that additional signaling cues might be necessary for maintenance of iCPCs. Canonical Wnt signaling is critical for proliferation of CPCs (Cao et al., Cell Res. 23:1119-32 (2013); Kwon et al., *PNAS* 104:10894-10899 (2007); Qyang et al., Cell Stem Cell 1:165-79 (2007)) and JAK/STAT signaling is important for normal cardiogenesis (Foshay et al., *Stem Cells* 23:530-543 (2005); Snyder et al., *J. Biol. Chem.* 285: 23639-23646 (2010)). The effect of supplementing reprogramming medium with BIO (canonical Wnt activator) and/or LIF (JAK/STAT activator) on reprogramming efficiency and the ability of EYFP+ cells to maintain a proliferative state was tested. Surprisingly, addition of LIF alone inhibited the generation of EYFP+ cells and colony formation. Addition of BIO alone resulted in a similar reprogramming efficiency as dox only; however, the EYFP+ cells became spindle-like upon passaging and were not highly proliferative. The LIF+BIO combination produced the brightest EYFP+ cells and the EYFP+ cells were robustly expandable (FIGS. 3E-G). Hence, both LIF and BIO are included in our iCPC maintenance culture medium—"iCPC induction medium." Infection of the 11-factor library followed by culture in iCPC induction medium produced 6-9 EYFP+ colonies (per 50,000 starting cells) that were continuously expanded on splitting (0.013% reprogramming efficiency). To determine whether LIF+BIO was necessary for initial reprogramming, we tested whether EYFP+ colonies generated by the dox only condition could be expanded by addition of LIF+BIO later during passaging. We observed that addition of LIF+BIO starting at passage 1 allowed for robust expansion of dox only EYFP+ cells, indicating that the impact of LIF+BIO was more on the maintenance of the reprogrammed state than on initiation of reprogramming.

Figure 5:
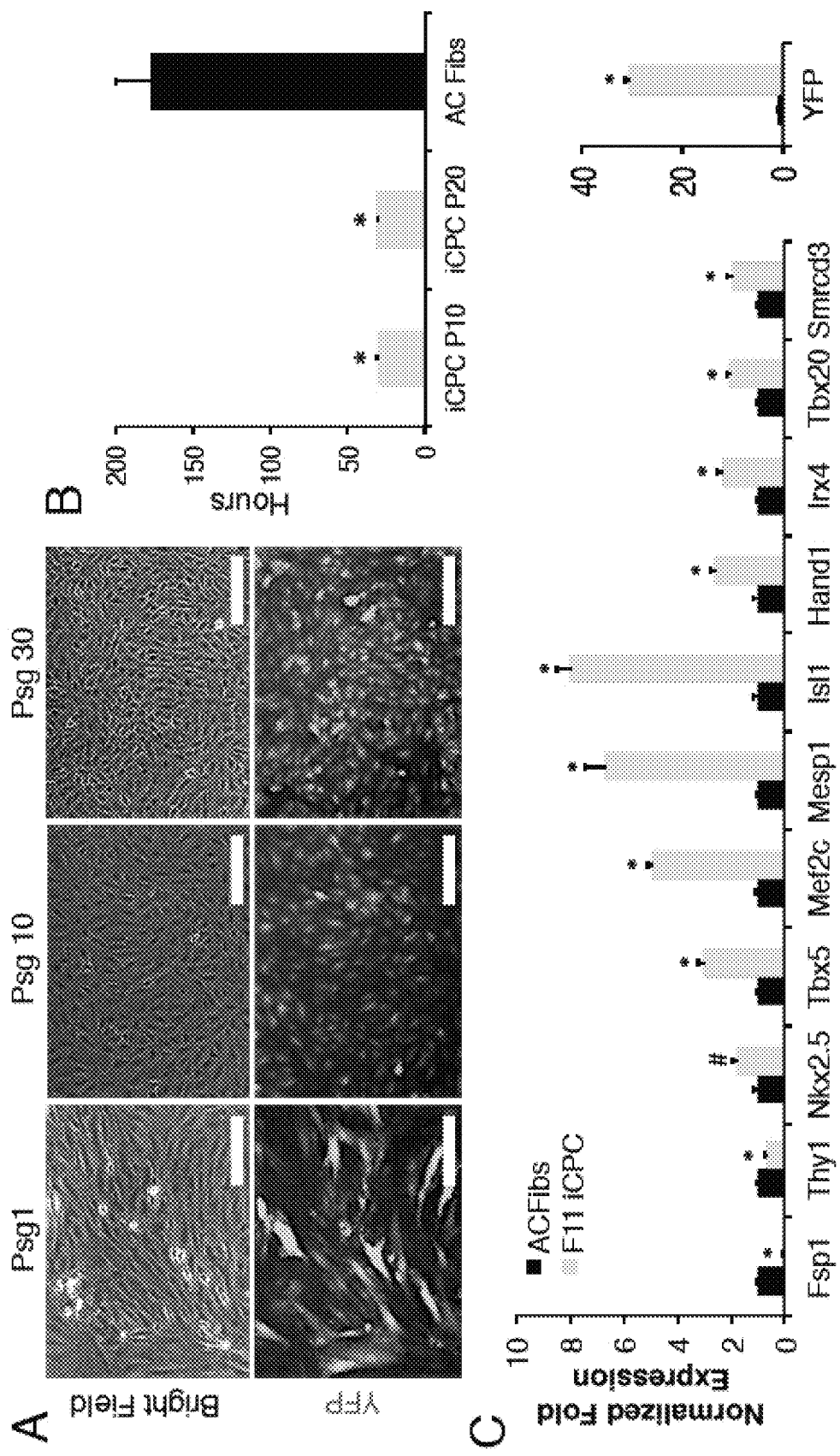
FIG. 5 depicts eleven factors that in combination stably reprogram adult cardiac fibroblasts into proliferative iCPCs. (A) iCPCs maintained EYFP expression and proliferative ability for at least 30 passages after dox withdrawal. (B) Population doubling time for passage 10 (P10) and passage 20 (P20) iCPCs as compared to uninfected AC Fibs. Data represented as mean (n=3). (C) qPCR analysis showed upregulation of CPC markers and downregulation of fibroblast markers. Data represent normalized fold expression relative to uninfected AC Fibs (*p<0.01, #p<0.05). (D) Immunofluorescence labeling of iCPCs showed nuclear localization of TFs Nkx2.5, Gata4, and Irx4 and flow cytometry analysis revealed that almost all of iCPCs expressed these TFs (E). (F) Flow cytometry analyses showed that iCPCs expressed cell surface makers such as Cxcr4, Flk1, Pdgfr-α, cKit that are associated with CPCs (n=3). Error bars=SEM. Scale bars=200 μm.
Figure 5:
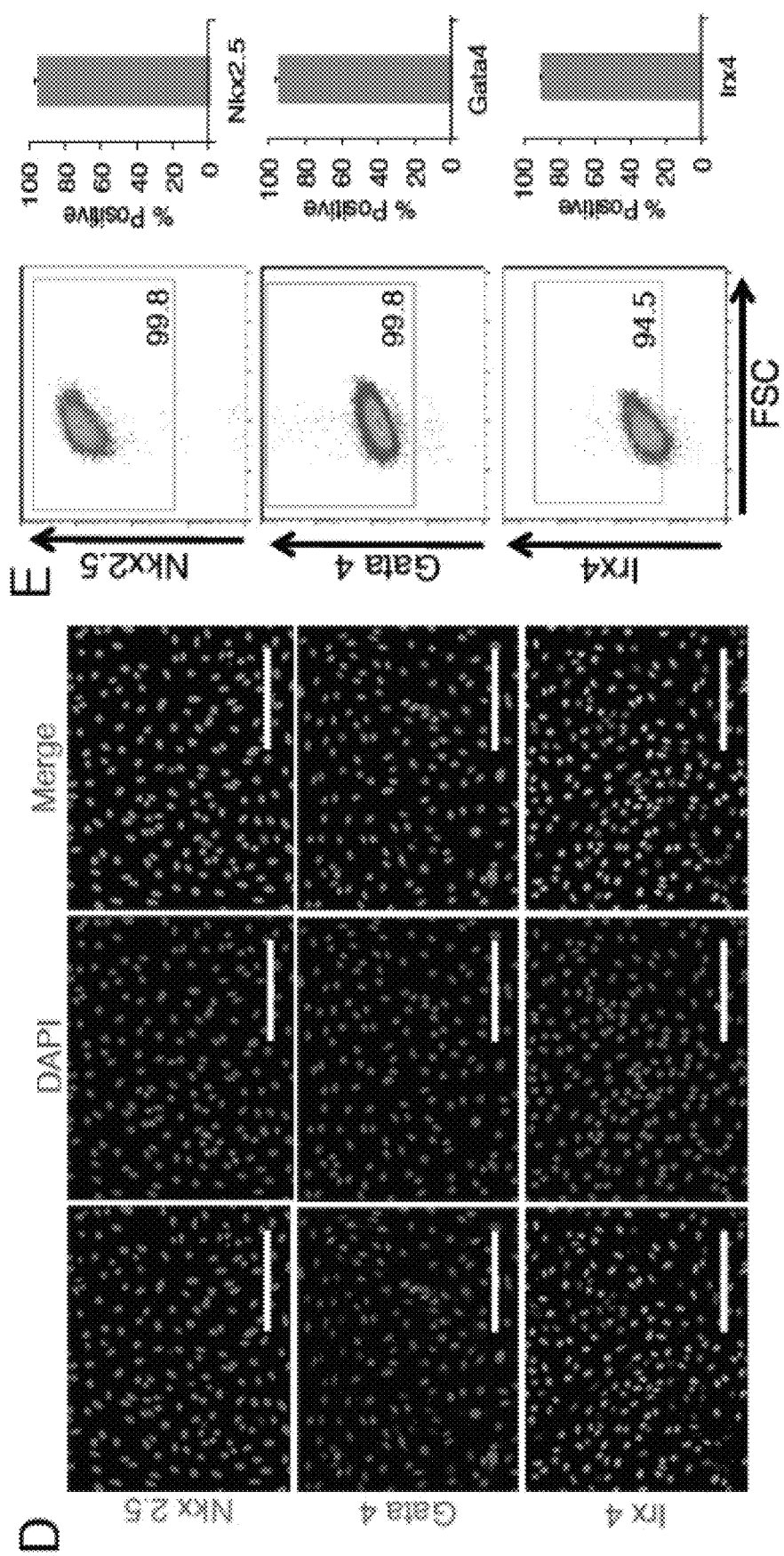
Figure 5:
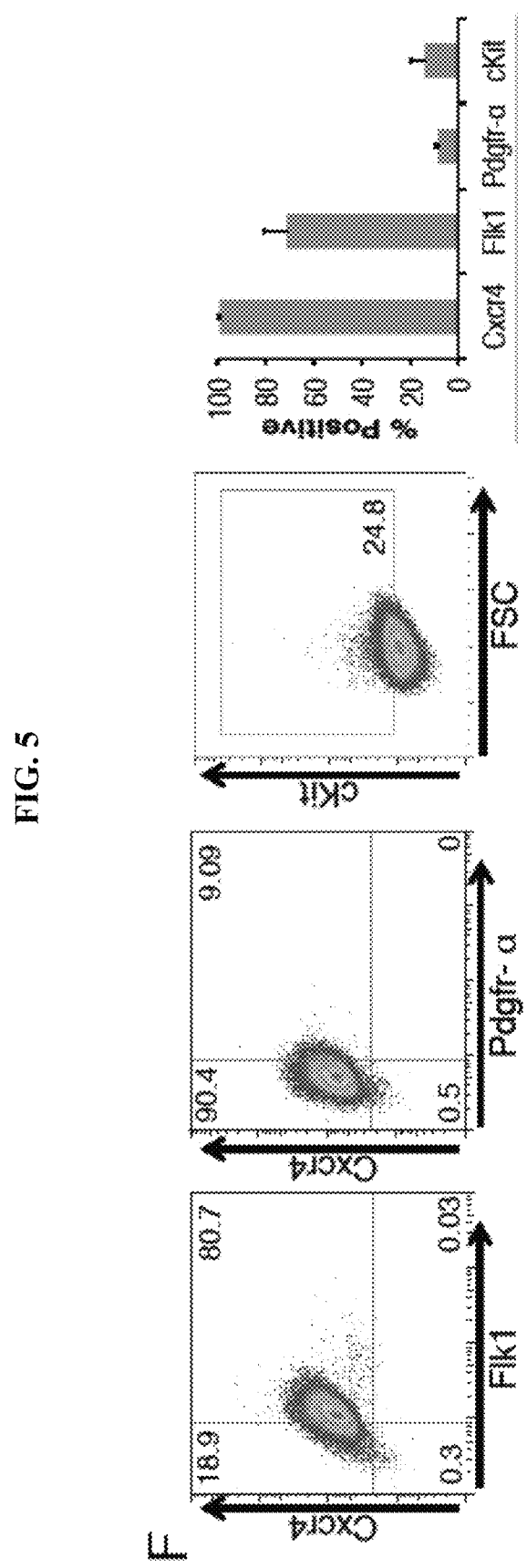

11-Factors Stably Reprogram Adult Cardiac Fibroblasts into Cardiac Mesodermrestricted iCPCs To determine whether continued forced expression of 11-factors (Mesp1, Mesp2, Gata4, Gata6, Baf60c, SRF, Isl1, Nkx2.5, Irx4, Tbx5, Tbx20) was required to maintain the iCPC state, we withdrew dox from the iCPC induction medium (iCPC maintenance medium) after 2 passages and assessed whether EYFP+ cells remained proliferative. Cells maintained EYFP expression as well as their proliferative ability for over 30 passages (FIG. 5A). The EYFP+ cells continued to reduce in size during the initial passage until passages 2-3, at which point they reached a steady state after which their morphology remained unchanged during further passaging. The population doubling time of iCPCs that had been passaged in iCPC maintenance medium for 10 and 20 passages was determined. Both passage 10 and passage 20 iCPCs had similar population doubling time of about 30 hours, which was significantly less than AC Fibs (FIG. 5B). These results suggest that iCPCs were stably reprogrammed and maintained their epigenetic state in the presence of LIF+BIO and without exogenous induction of cardiac factors by dox.

Quantitative PCR (qPCR) analysis of iCPCs revealed upregulation of key CPC transcription factors including Nkx2.5, Tbx5, Mef2c, Mesp1, Tbx20, and Irx4 accompanied by down regulation of the fibroblast-specific gene Fsp1 (FIG. 4C). These data indicate that iCPCs initiated the cardiac epigenetic program at the expense of the fibroblast program, a hallmark of lineage reprogramming. Next, we performed immunostaining for CPC transcription factors (TFs). In contrast to AC Fibs, which did not immunolabel for Nkx2.5, Gata4 or Irx4 (data not shown), iCPCs exhibited nuclear localization of these TFs that remained constant across passages 5-25 (FIG. 5D). Flow cytometry demonstrated that greater than 95% of the iCPCs expressed Nkx2.5, Gata4, and Irx4 (FIG. 5E). Further, we assessed whether iCPCs expressed cell surface markers associated with CPCs (Kattman et al., *Cell Stem Cell* 8:228-240 (2011); Nelson et al., *Dev. Dynamics* 243:381-92 (2008)). Flow cytometry analysis revealed that iCPCs homogenously expressed Cxcr4; however, only a fraction of iCPCs expressed Flk1, Pdgfr-α, or cKit (FIG. 5F). We found no protein expression for pluripotency (Oct4) or cardiac lineage differentiation markers (α-MHC, SM-MHC, CD31) even after extensive passaging (data not shown).

Figure 6:
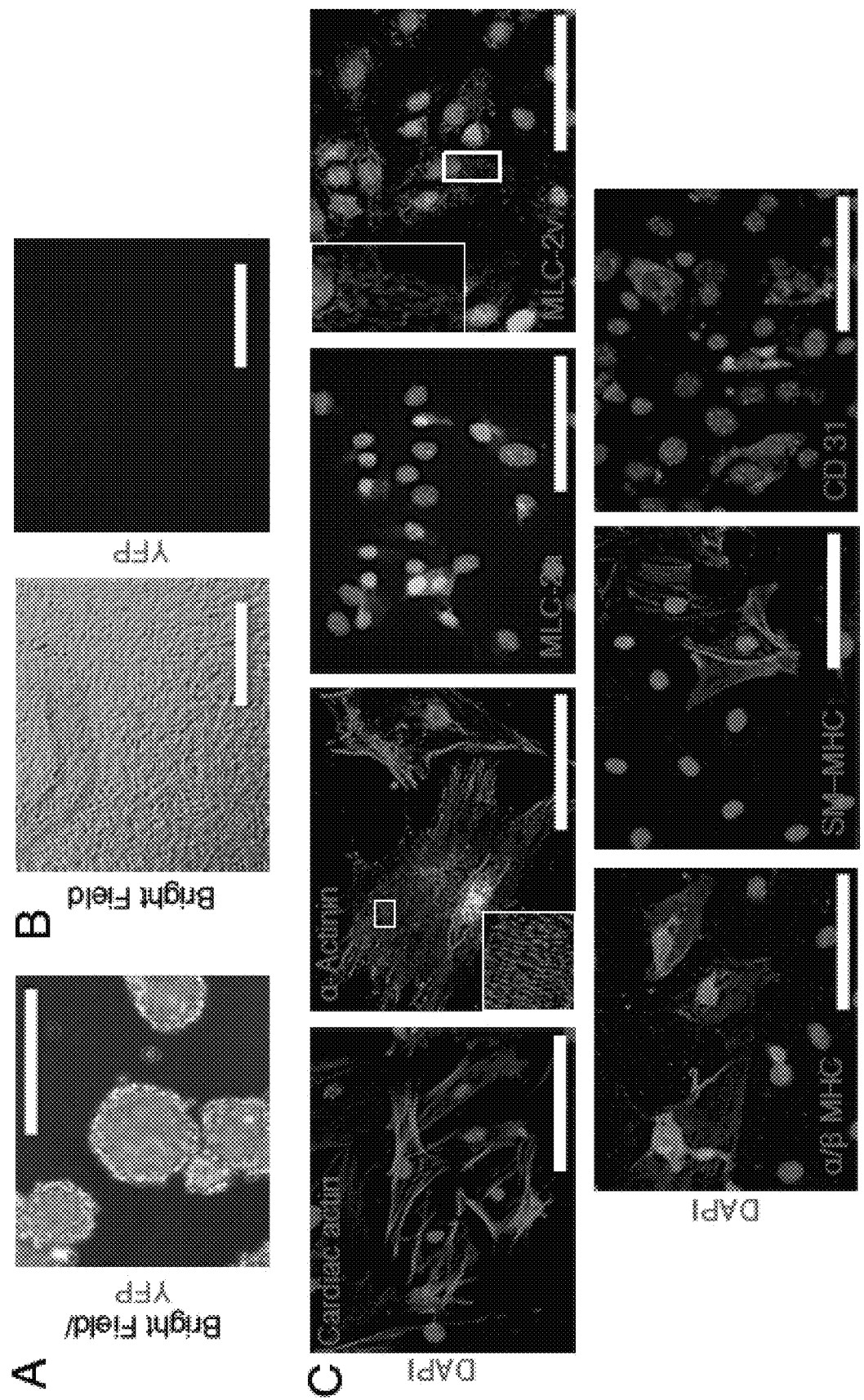
FIG. 6 demonstrates that iCPCs are multipotent and differentiate into contracting cardiomyocytes, smooth muscle cells, and endothelial cells in vitro. (A) iCPCs aggregated in cardiac differentiation medium were YFP+ at day 2 (B) iCPC aggregates were plated and cultured in low serum conditions and lost Nkx2.5-EYFP expression by day 20. (C) Immunocytochemistry on plated cells revealed expression of CM markers such as cardiac actin, α-actinin (note highly organized sarcomere staining), MLC-2a, MLC-2v, α/β MHC, a SM marker SM-MHC and EC marker CD31. (D) iCPC-CMs infected with a GFP expressing lentivirus co-cultured with mESC-CMs that expressed td-tomato. No cell fusion was detected. (E) Cx43 immunolabeling showed that iCPC CMs developed gap junctions with mESC-CMs and other iCPC-CMs. (F) iCPC-CMs showed synchronous calcium transients with mESC-CMs 3 weeks after co-culture. White arrow=iCPC-CM, yellow arrow=mESC-CM. (G) Quantification of calcium transients. Scale bars=400 μm in A & B, 100 μm in C, 200 μm in D, 50 μm in E, 10 μm in F, 1 second in G.

To characterize the transcriptome of iCPCs, we performed RNA-seq analysis on early passage (1-3) as well as late passage (8-10) iCPCs and compared with uninfected AC Fibs. We found that genes involved in cardiovascular development including TFs (Tbx3, Hes1, Prrx1, Foxa2, Gata4/6, Meis1, Gli2), signaling molecules (LIF, Vegfc, Grem1, Fgf2), cell surface markers (cKit, Pdgfr-α, Notch1, Gpc3) and chromatin remodeling genes (Smarcd3, Hdac 2/5/7/10, Jarid2) were increasingly upregulated as iCPCs were passaged. In contrast, fibroblast-specific genes (Postn, Twist2, Thy1) were increasingly downregulated with passaging. Furthermore, CM differentiation markers (Actc1, Myh6, Myl2, Myl7) were not expressed in iCPCs. Interestingly, genes associated with smooth muscle (SM) (Cnn1, Myh11) and endothelial cells (EC) (Pecam1) were upregulated in one early passage replicate. However, these genes were downregulated in late passage iCPCs. Primitive streak genes (Gsc, Mixl1, T) were not detected. Likewise, progenitor genes for endoderm, ectoderm and non-cardiac mesoderm were not expressed. Additionally, Bone Morphogenetic Protein (BMP) (4/6/7) genes that induce cardiac differentiation were also downregulated. Importantly, iCPCs did not express markers of pluripotent stem cells (Pou5f1, Esrrb, Dppa2/3, Lin28a, Sox2); however, we did observe upregulation of Nanog. These data demonstrate that iCPCs are cardiac mesoderm-restricted precursors. Gene Ontology (GO) terms associated with upregulated genes in iCPCs include categories such as "positive regulation of cell proliferation," "negative regulation of cell differentiation," and "cardiovascular system development," whereas terms associated with the downregulated genes include categories such as "cell adhesion," "cell differentiation," and "apoptosis" (FIG. 4).

iCPCs Differentiate into Cardiomyocytes, Smooth Muscle Cells, and Endothelial Cells To determine whether iCPCs were capable of differentiation into cardiovascular lineages, iCPCs were aggregated in cardiac differentiation medium. iCPCs maintained EYFP expression in aggregates. However, 20 days after plating, cells lost EYFP expression, suggesting that the iCPCs exited the progenitor state and differentiated (FIGS. 6A-B). Immunocytochemistry revealed differentiated cells expressing CM (cardiac actin, α-actinin, MLC-2a, MLC-2v, α/β MHC), SM (SM-MHC) or EC (CD31) markers (FIG. 6C). These results suggest that iCPCs were multipotent, capable of differentiating into three types of cardiovascular lineage cells. We evaluated the differentiation potential of passage 5 and 30 iCPCs and observed that multipotency was maintained across passages (data not shown). Among iCPC-differentiated cells, a majority stained positive for CM-markers (80-90%) and only a fraction stained for SM (5-10%) and EC markers (1-5%). Most MLC-2v positive CMs also labeled for MLC-2a, indicating that they were relatively immature.

Figure 7:
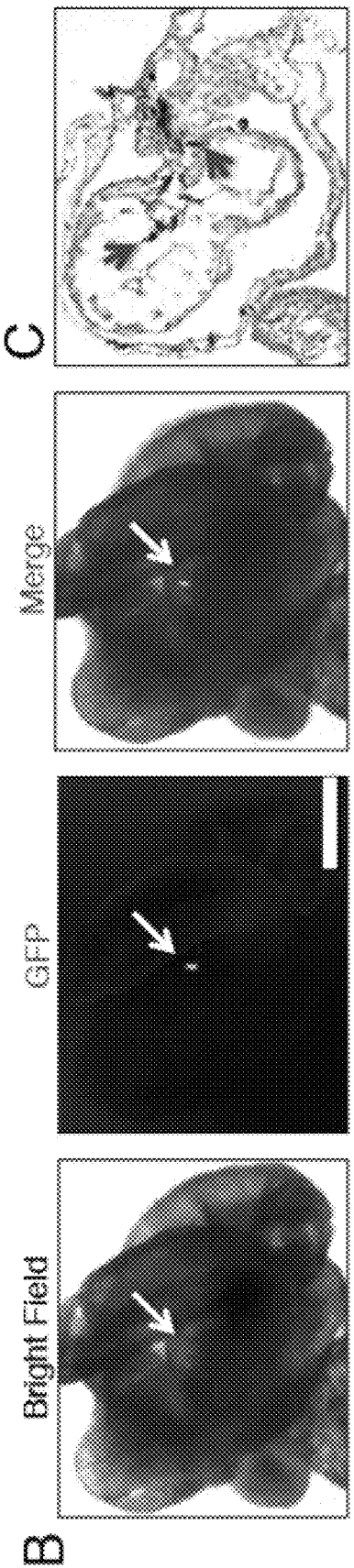
FIG. 7 depicts the differentiation of mouse iCPCs into functional cardiomyocytes ex vivo. (A) Shows the number of embryos injected with iCPCs and the location of iCPC-derived cells 24 or 48 hrs after whole embryo culture. (B) iCPCs (labeled with GFP expressing lentivirus) injected into the cardiac crescent of mouse embryos colonized the developing heart tube as assessed after 24 hrs of whole embryo culture. (C) Histological sections of iCPC injected embryos were stained for GFP antibody (dark brown color). iCPC-derived cells (brown arrows) integrated with host cell in the developing heart tube. (D) 24-hr cultured embryos were immunostained in whole mount preparations for CM markers and GFP. 3D reconstruction images show iCPCs differentiated into CMs, as indicated by co-expression of CM markers and GFP. (E) iCPC-CMs matured ex vivo after extended culture period (48 hours) and attained shape/size similar to native CMs.

Even after attaining highly organized sarcomeres following extended culture periods under low serum conditions, the iCPC-derived CMs did not exhibit spontaneous contractions. We reasoned that co-culturing iCPC-CMs with mESC-derived CMs may provide additional mechanical, electrical and paracrine stimulation to induce further maturation and contraction. Co-culturing with rat CMs has been previously shown to induce contraction in iCMs (Wada et al., 2013). Hence, we infected iCPC-CMs with a constitutive GFP expressing lentivirus to identify reprogrammed cells and co-cultured them with mESC-derived CMs expressing td-tomato. We did not detect cells that coexpressed both GFP and td-tomato (FIG. 6D), suggesting that cell fusion between iCPC-CMs and mESC-CMs was unlikely. We immunostained the co-cultured cells for CM markers as well as GFP and noticed that GFP$^+$ iCPC-CMs and GFP-mESC-CMs both stained positive for CM markers and grew side by side as monolayers (data not shown). Moreover, immunostaining for Cx43 revealed that iCPC-CMs developed abundant gap junctions with both mESC-CMs as well as other iCPC-CMs (FIG. 6E). After 10-14 days of co-culturing, 5-10% of iCPC-CMs started synchronously contracting with mESC-CMs. The contracting iCPC-CMs also showed spontaneous calcium transients that were similar to those in mESC-CMs in frequency and amplitude (FIGS. 6F-G).

iCPCs Differentiate into Cardiomyocytes when Injected into the Cardiac Crescent of Mouse Embryos After demonstrating the cardiovascular potency of iCPCs in vitro, we wanted to assess their potency in vivo. Hence, we injected iCPCs into the cardiac crescent of mouse conceptuses (headfold 4-6 somite pairs stage). The rich cardiogenic signaling environment present in the crescent promotes differentiation of embryonic CPCs (Abu-Issa and Kirby, Annu Rev Cell Dev Biol 23:45-68 (2007)). iCPCs were first infected with a constitutive GFP expressing lentivirus to track their progeny post-injection. We injected 200-500 iCPCs each in a total of 20 embryos in two separate experiments and cultured whole operated and unoperated control conceptuses for 24 or 48 hrs. During this culture period, the cardiac mesoderm undergoes a morphogenic shift to develop into a beating heart tube. We performed live imaging on injected embryos to determine the location of the GFP$^+$ cells. In 3/20 embryos no GFP$^+$ cells were detected, possibly due to leakage of cells out of the injection site during the injection. In 15/17 of the remaining embryos (88%), GFP$^+$ cells localized exclusively to the developing heart and appeared to beat along with the endogenous CMs (FIGS. 7A-B). The presence of GFP$^+$ cells in the heart tube suggests that iCPCs were able to respond to cardiac-morphogenetic signaling in the developing embryo and localize/differentiate along with host CPCs to the beating heart tube. To assess whether the iCPC-derived cells could integrate with host cells, some of the injected embryos were sectioned and immunostained with a GFP antibody. We observed that iCPC-derived cells (brown color) integrated with host cells within the heart tube (FIG. 7C).

To determine if injected iCPCs differentiated into CMs in vivo, whole mount embryos were co-immunostained for GFP and CM markers. Specimens were imaged as optical sections (1 μm) using multi-photon excitation microscopy, and 3D reconstructions of the z-stack images were performed. In the 24-hr cultured embryos, we detected several GFP$^+$ cells in the heart tube that co-stained for CM markers such as MLC-2v and cardiac actin. In 24-hr cultured embryo samples the iCPC-derived CMs had an elongated appearance and looked morphologically distinct from the native CMs (FIG. 7D). However, iCPC-derived CMs in the 48-hr cultured embryos had a rounder morphology and appeared similar in shape and size to the native CMs (FIG. 7E). The morphological change (from elongated to round) suggests that the iCPC-CMs continue to mature in vivo during the extended culture. iCPC-CMs were observed in developing atria, ventricles as well as outflow track, showing no spatial preference within the heart tube.

Although we observed endothelial differentiation from iCPCs in vitro, we were unable to convincingly detect iCPC-derived CD31 cells in vivo. Due to the limited endothelial potency of iCPCs (only 1-5% detected during in vitro differentiation), we may have missed rare CD31$^+$ cells within embryos. A limitation of the whole embryo culture technique used here is that it was specifically designed for early gastrulae (Lawson et al., Development 113:891-911 (1991)), that culture from ~E7.75 to E10.5. The culture period cannot be extended beyond E10.5 as the embryo becomes increasingly dependent upon formation of a chorioallantoic placenta, and interaction with its mother (Cockroft, Postimplantation Mammalian Embryos: A Practical Approach (Eds. A. J. Copp and D. L. Cockroft). IRL Press: Oxford. Pp. 15-40 (1990)). Hence, we were unable to assay embryos for smooth muscle as the onset of smooth muscle differentiation is after E10.5 (Madsen et al., Circ. Res. 82:908-917 (1998); Miano et al., Circ. Res. 75:803-12 (1994)), which exceeded our whole embryo culture duration (E7.75-E9.75).

Five Factors Sufficient to Reprogram Adult Cardiac Fibroblasts to iCPCs

Figure 8:
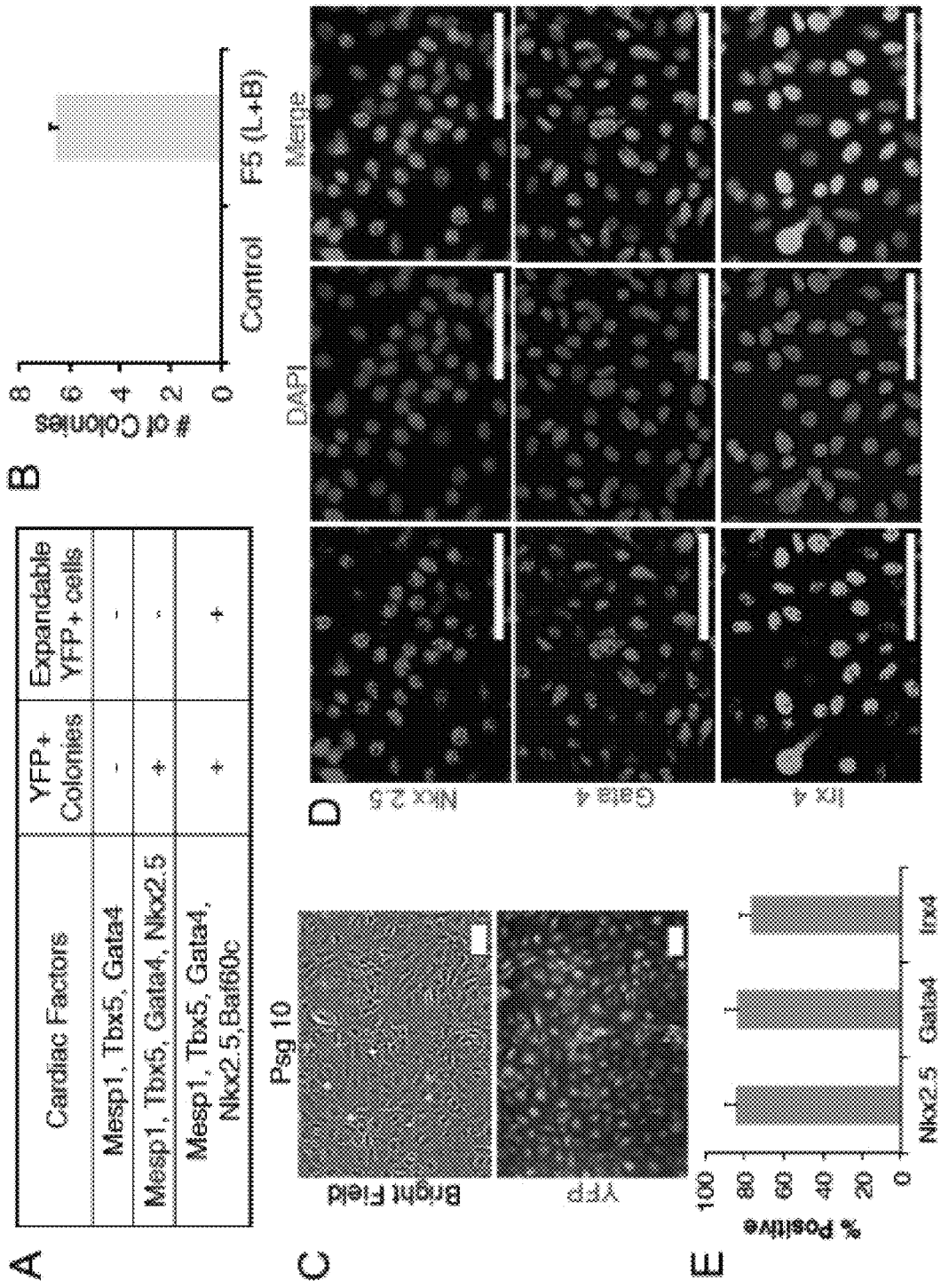
FIG. 8 depicts five factors that in combination stably reprogram adult cardiac fibroblasts into proliferative and multipotent iCPCs. (A) Factor combinations tested both for ability to produce Nkx2.5-EYFP+ colonies and to expand them for at least 5 passages without dox. [MTG (n=3), MTGN (n=5), MTGNB (n=5)] (B) Number of EYFP+ colonies produced after infection with 5 factors and culture in iCPC induction medium for 3 weeks (per 50,000 seeded cells). (L=LIF, B=BIO) (C) EYFP+ cells reprogrammed using 5 factors could be stably expanded without dox. (D) Immunolabeling of 5 factor iCPCs showed nuclear localization of TFs Nkx2.5, Gata4, and Irx4, quantified by flow cytometry analysis in (E). (F) 5 factor iCPCs expressed surface markers associated with CPCs as shown by flow cytometry analysis (n=2). (G) iCPCs reprogrammed with 5 factors were multipotent and could be differentiated into CMs (cardiac actin, α-actinin, MLC-2a, MLC-2v, α/β MHC), SMs (SM-MHC) and ECs (CD 31). Note highly organized sarcomere staining for α-actinin. Data presented as mean, error bars=SEM. Scale bars=100 μm.

We wanted to determine whether iCPCs could be obtained from adult cardiac fibroblasts using a subset of the 11 factors. Initially, we infected AC Fibs with a combination of three cardiac factors, Gata4 (G), Mesp1 (M), and Tbx5 (T), and cultured them in iCPC induction medium, but we did not observe emergence of any EYFP+ colonies for up to 4 weeks. Therefore, we tested whether addition of Nkx2.5 to Gata4 (G), Mesp1 (M), and Tbx5 (T) (MTGN) could induce formation of EYFP+ colonies. The four factors (MTGN) followed by culture in iCPC induction medium, produced EYFP+ colonies after 3 weeks. Although these EYFP+ cells proliferated for the first two passages, their proliferative ability as well as EYFP expression progressively declined with subsequent passaging (FIG. 8A). This indicated that MTGN induced partial reprogramming and was insufficient to epigenetically stabilize cells in the iCPC state. Hence, we tested if the addition of Baf60c, (a chromatin remodeling agent) to MTGN (MTGNB) could facilitate stable reprogramming to iCPCs. Indeed, infection with 5 factors (MTGNB) reproducibly gave rise to EYFP+ colonies (~7 colonies/50,000 cells), which could be stably expanded in iCPC maintenance medium (without dox) for at least 20 passages (FIGS. 8A-C). A majority of 5-factor reprogrammed iCPCs showed nuclear localization of CPC TFs Irx4 (78%), Gata4 (84%) and Nkx2.5 (85%) as well as expressed CPC associated cell surface markers (Cxcr4, Flk1, Pdgfr-α and cKit) (FIGS. 8D-F). Also, upon re-aggregation in cardiac differentiation medium followed by low serum culture, 5-factor iCPCs differentiated into CMs (cardiac actin, α-actinin, MLC-2a, MLC-2v, α/β MHC), SMs (SM-MHC) and ECs (CD31) indicating their multipotency (FIG. 8G). 5-factor iCPCs were comparable to 11-factors iCPCs in morphology, EYFP expression, proliferative ability, staining for CPC markers, as well as cardiac lineage potency.

11/5-Factors Stably Reprogram Adult Lung and Tail-Tip Fibroblasts to iCPCs

Figure 9:
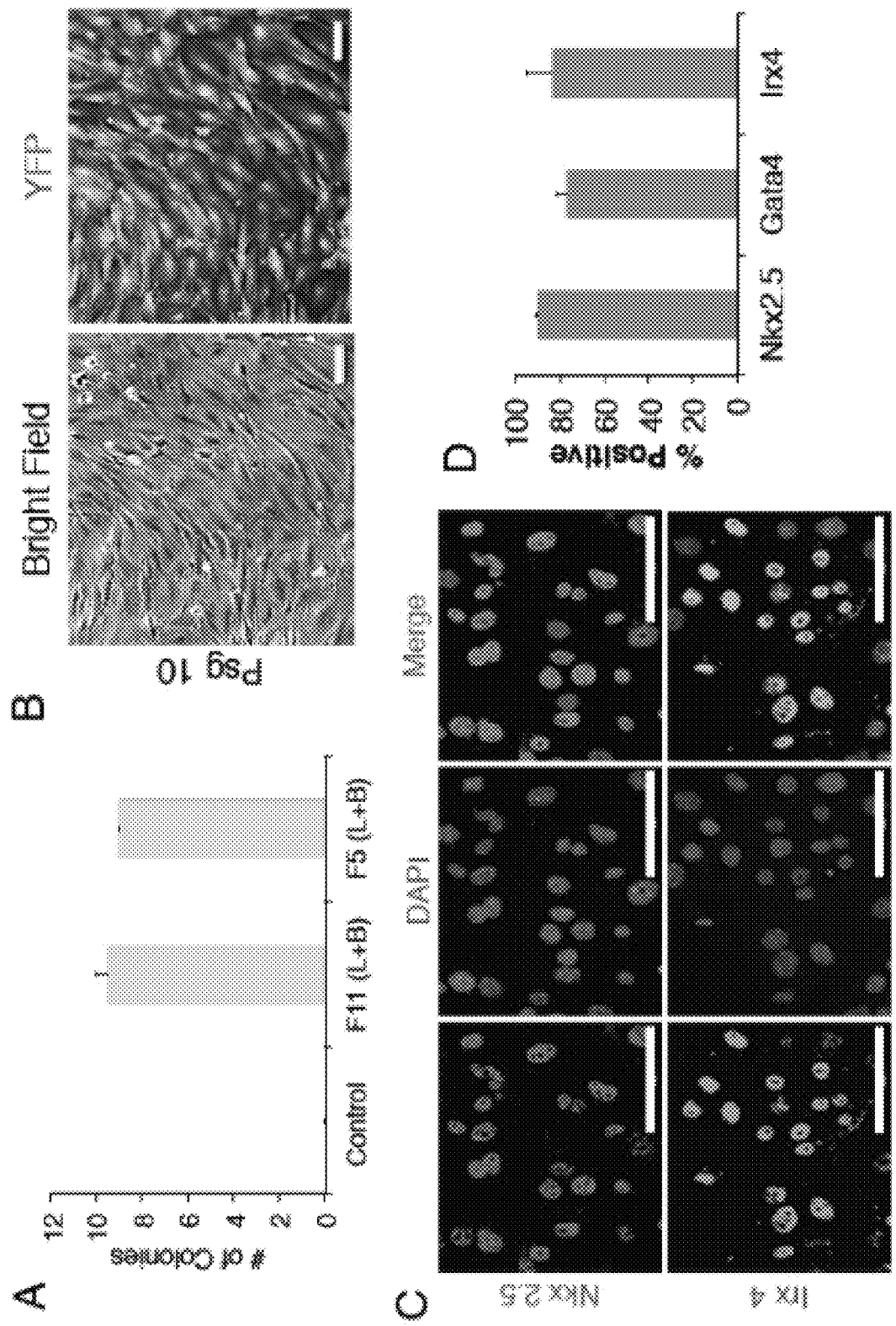
FIG. 9 depicts combinations of cardiac factors that stably reprogram adult mouse lung fibroblasts into proliferative and multipotent iCPCs. (A) Number of Nkx2.5-EYFP+ colonies produced (per 50,000 seeded cells) after infection of adult lung fibroblasts with 11 or 5 factors and culture in iCPC induction medium for 3 weeks (n=4). (L=LIF, B=BIO) (B) EYFP+ cells reprogrammed using a set of 5 factors were stably expanded without dox shown after 10 passages. (C) Immunolabeling revealed lung-iCPCs had nuclear localization of CPC TFs, quantified in (D). (E & F) Flow cytometry analysis revealed that Lung-iCPCs expressed cell surface markers associated with CPCs (n=3). (G) Lung-iPSCs were multipotent and differentiated into CMs (cardiac actin, α-actinin, MLC-2a, MLC-2v, α/β MHC), SMs (SMMHC) and ECs (CD31). Note highly organized sarcomere staining for α-actinin. Data presented as mean, error bars=SEM. Scale bars=100 μm.
Figure 10:
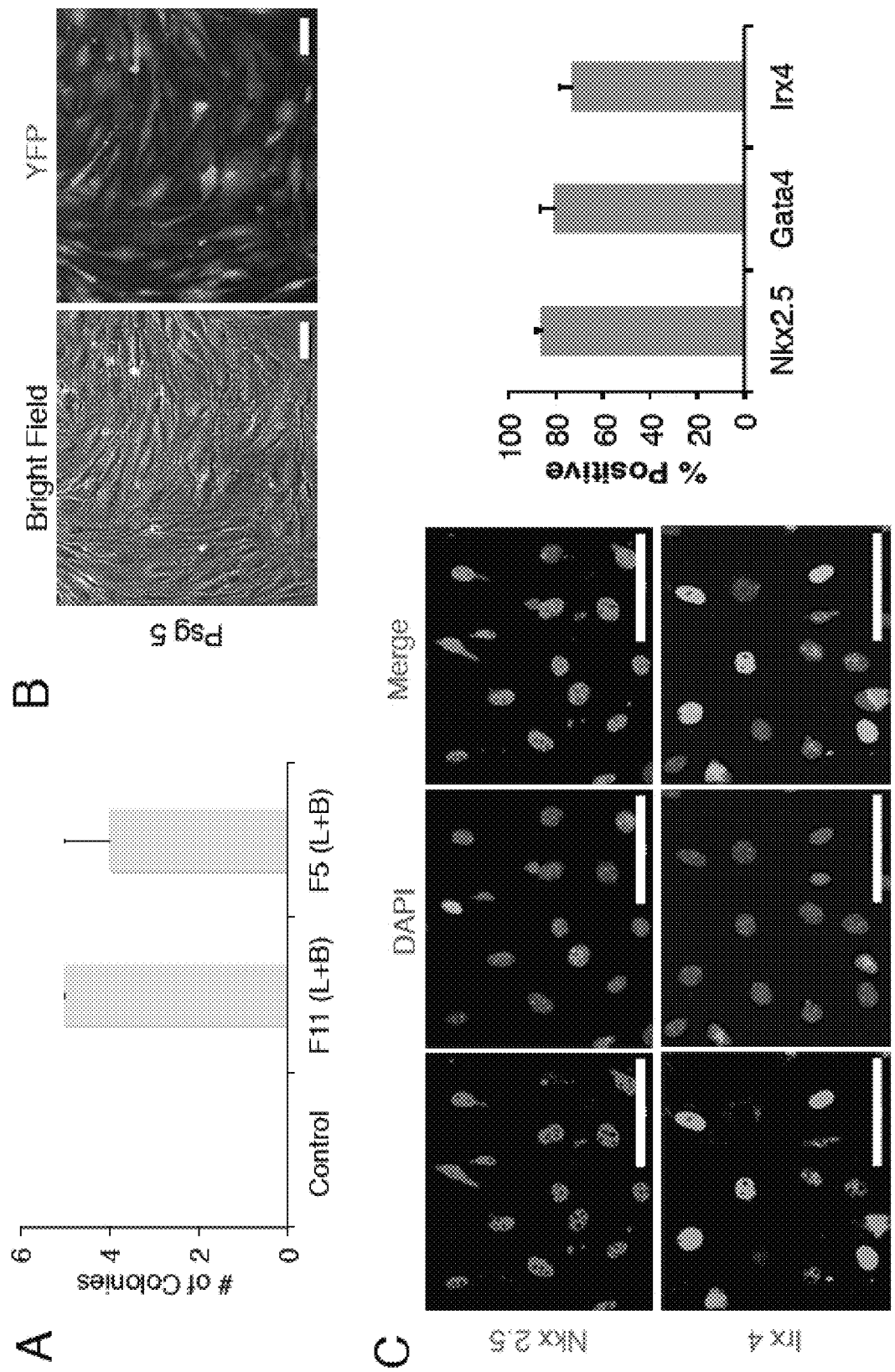
FIG. 10 depicts cardiac factors that stably reprogram adult mouse tail-tip fibroblasts into proliferative and multipotent iCPCs. (A) Number of Nkx2.5-EYFP+ colonies produced after infection of adult tail-tip fibroblasts with 11 or 5 factors (n=4). (B) EYFP+ cells reprogrammed using 5 factors could be stably expanded without dox. (C) Tail-tip-iCPCs expressed TFs associated with CPCs. (D) Tail-tip-iCPCs expressed cell surface markers associated with CPCs (n=3). (E) Tail-tip-iCPCs were multipotent and differentiated into cardiomyocytes (cardiac actin, α-actinin, MLC-2a, MLC-2v, α/β MHC), smooth muscle cells (SM-MHC) and endothelial cells (CD 31). Note highly organized sarcomere staining for α-actinin. Data presented as mean, error bars indicate standard error of mean. Data presented as mean, error bars=SEM. Scale bars represent 100 μm.

To determine whether iCPCs could be reprogrammed from non-cardiac sources of fibroblasts, we isolated adult lung fibroblasts (AL Fibs) and adult tail-tip fibroblasts (AT Fibs) from Nkx2.5-EYFP/rtTA transgenic mice. Both AL Fibs and AT Fibs stained negative for CPC TFs as well as cardiac lineage differentiation markers and had no EYFP expression. We infected AL Fibs and AT Fibs with either 11 or 5 factors and cultured them in iCPC induction medium. AL Fibs infected with 11 factors or 5 factors produced 9 EYFP+ colonies (per 50,000 cells) (FIG. 9A). AT Fibs infected with 11 factors or 5 factors produced 5 or 4 EYFP+ colonies (per 50,000 cells), respectively (FIG. 10A). EYFP+ cells reprogrammed from both lung and tail-tip fibroblasts were stably expanded in iCPC maintenance medium for at least 10- and 7-passages, respectively, stained positive for CPC markers, and differentiated into CMs, SMs and ECs (FIGS. 9B-G and FIGS. 10-B-G) indicating that adult fibroblasts from diverse tissues of origin can be stably reprogrammed into proliferative and multipotent iCPCs.

11-Factor Set Reprograms Genetically Unmodified Human Fibroblasts into Morphologically Distinct and Highly Proliferative iCPCs We wanted to determine whether iCPC reprogramming could be recapitulated using human cells. For the initial experiments we chose human fetal lung fibroblasts cells (IMR 90). IMR 90 fibroblasts were one of the first human cells that were reprogrammed to iPSC state, and their ability to undergo reprogramming is documented. Also, transitioning direct reprogramming technologies, which were first optimized using mouse cells, to human cells has been challenging. Hence, we reasoned that fetal fibroblasts, which are more amenable to transdifferentiation than adult cells, may be suitable for an initial demonstration.

Figure 11:
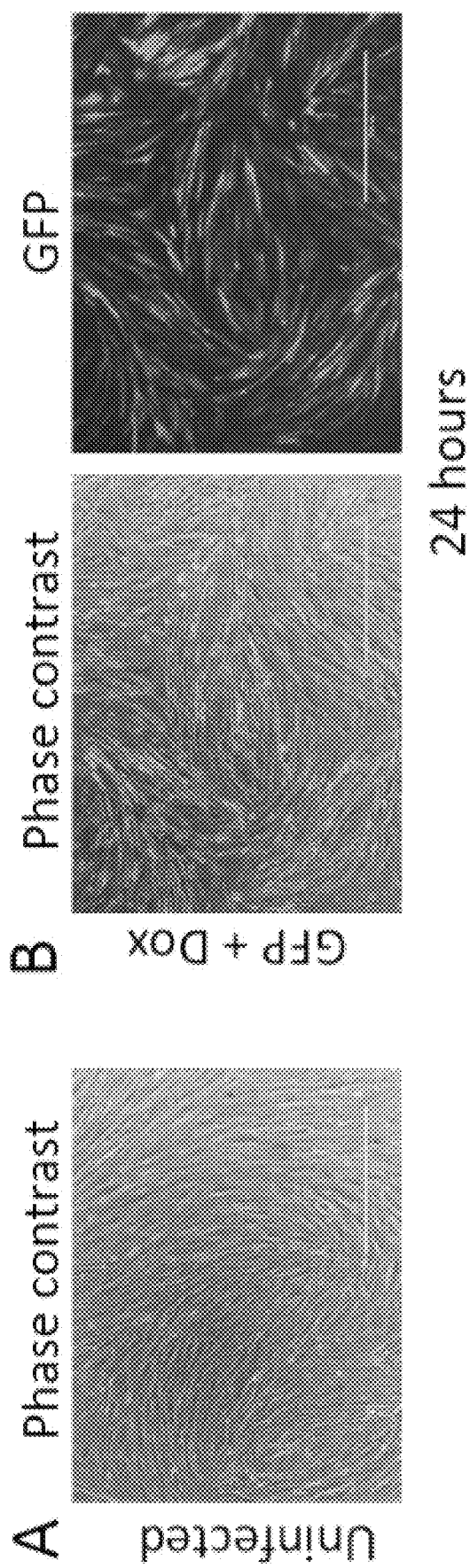
FIG. 11 depicts stable reprogramming of genetically unmodified human fibroblasts into proliferative and multipotent iCPCs by 11 cardiac factors. (A-B) Phase contrast images show human fibroblasts before (A) and 24 hours after (B) dox induction of cells infected with dox-inducible GFP lentivirus+11-factor set. GFP fluorescence was observed only after dox induction. (C) Proliferative and morphologically distinct cells are visible 2 weeks after dox induction. (D) By day 24, these cells developed into colonies of highly proliferative cells.

IMR 90 fibroblasts were cultured in fibroblast medium (described earlier) and showed spindle-like, elongated morphology (FIG. 11A). First, they were infected with a rtTA lentivirus to allow for doxycycline inducible transgene expression (IMR-rtTA). As a control to test dox inducible gene expression, IMR-rtTA cells were infected with a GFP lentivirus and induced with dox. Twenty-four hours after dox induction, 80-90% of the infected cells showed bright GFP expression (FIG. 11B). These cells were cultured in dox containing medium for 2-3 weeks. Even though the cells continued to express GFP, the morphology of the cells remained unchanged following infection with GFP lentivirus and extended culture (FIG. 11C). Next we infected IMR-rtTA cells with 11 cardiac factors and induced with dox. We noticed proliferative and morphologically distinct cells 2 weeks after dox induction. By day 24, these cells developed into colonies of highly proliferative cells (FIG. 11D). Unlike mouse fibroblasts, which had an Nkx 2.5-EYFP cardiac reporter, the IMR 90 cells were not genetically engineered. Hence, we relied on the dramatic morphological change that fibroblasts undergo during iCPC reprogramming as a marker to identify cells undergoing transdifferentiation. Based on the appearance of morphologically distinct, proliferative colonies iCPC reprogramming efficiency was calculated to be 0.02%.

Human iCPCs Express CPC TFs and Differentiate into Cardiomyocytes, Smooth Muscle Cells and Endothelial Cells iCPCs maintained proliferative ability and were expanded for 2-3 passages under dox induction. Next, we performed immunostaining for CPC TFs such as Irx4, Mesp1, Nkx 2.5, and Tbx5 (dox was withdrawn for 1 week prior to immunostaining) A majority of cells exhibited nuclear localization of these TFs (FIG. 12A) indicating that the morphologically distinct, proliferative cells were indeed iCPCs.

Figure 12:
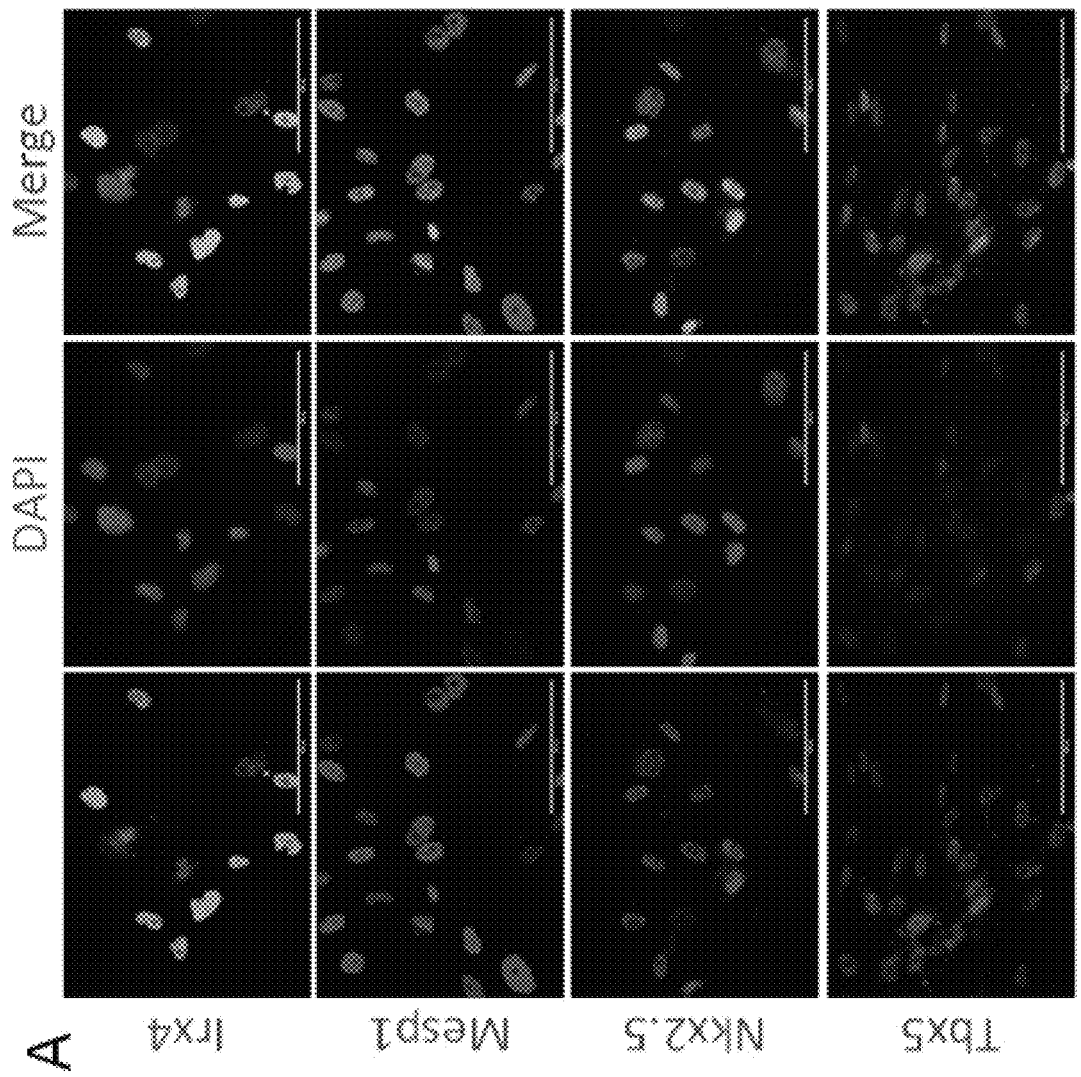
FIG. 12 depicts (A) immunolabeling of 11-factor human iCPCs, showing nuclear localization of TFs Tbx5, Nkx2.5, Mesp1, and Irx4. (B) Immunolabeling of human cardiomyocytes differentiated from human iCPCs, showing expression of cardiac actin, MLC-2a, α-actinin, MLC-2v, α-MHC, SM-MHC (marker of smooth muscle cells), and CD31 (marker of endothelial cells).

To determine whether iCPCs were capable of differentiation into cardiovascular lineages, iCPCs were aggregated in cardiac differentiation medium and differentiated as previously described. Immunocytochemistry revealed differentiated cells expressing CM (cardiac actin, α-actinin, MLC-2a, MLC-2v, α/β MHC), SM (SM-MHC) or EC (CD31) markers (FIG. 12B). These results suggest that human iCPCs were multipotent, capable of differentiating into three types of cardiovascular lineage cells. These data also demonstrate that our iCPC- and cardiomyocyte-differentiation methodologies are successfully recapitulated in human cell types and should be useful for a variety of mammalian species and various somatic cell types.

We claim:

1. An isolated induced cardiac progenitor cell (iCPC) comprising one or more vectors encoding Mesp1, Baf60c, Nkx2.5, Gata4, Tbx5, Mesp2, Gata6, SRF, Isl1, Irx4, and Tbx20, wherein the isolated iCPC is capable of differentiating into cardiomyocytes, SM-MHC+ smooth muscle cells, and CD31+ endothelial cells, wherein the iCPC is capable of proliferating and remaining multipotent for at least 5 passages in a culture medium comprising an activator of canonical Wnt signaling and an activator of Jak/Stat signaling, and wherein the iCPC is NKx2.5+, Gata4+, Irx4+, Cxcr4+, Oct4−, Mlc-2a−, SM-MHC−, and CD31−.

2. An in vitro cell culture comprising:

an NKx2.5+, Gata4+, Irx4+, Cxcr4+, Oct4−, Mlc-2a−, SM-MHC−, and CD31− induced cardiac progenitor cell (iCPC) population capable of differentiating into cardiomyocytes, SM-MHC+ smooth muscle cells, and CD31+ endothelial cells, wherein the iCPC population comprises iCPCs comprising one or more vectors encoding Mesp1, Baf60c, Nkx2.5, Gata4, Tbx5, Mesp2, Gata6, SRF, Isl1, Irx4, and Tbx20; and a cell culture medium comprising an activator of canonical Wnt signaling in an amount sufficient to maintain proliferation and multipotency of the iCPCs in the iCPC population for at least 5 passages.

3. The isolated induced cardiac progenitor cell of claim 1, wherein the one or more vectors further encode factors T, Hand1, Hand2, Tbx18, Tip60, SRF, Hey2, Oct4, Klf4, Sox2, and L-myc.

4. The in vitro cell culture of claim 2, wherein the activator of canonical Wnt signaling is BIO.

5. The in vitro cell culture of claim 2, wherein the cell culture medium further comprises an activator of Jak/Stat signaling.

6. The in vitro cell culture of claim 5, wherein the activator of Jak/Stat signaling is selected from the group consisting of Leukemia Inhibitory Factor (LIF), IL-2, IL-6, IL-11, leptin, and ciliary neurotrophic factor (CNTF).

7. The isolated induced cardiac progenitor cell population of claim 1, wherein the one or more vectors are selected from the group consisting of a viral vector, a non-viral episomal vector, a liposome, a polymer-nucleic acid complex, and a peptide-nucleic acid complex.

\* \* \* \* \*